United States Patent
Iadonato et al.

(10) Patent No.: US 9,884,876 B2
(45) Date of Patent: Feb. 6, 2018

(54) ANTI-VIRAL COMPOUNDS, PHARMACEUTICAL COMPOSITIONS, AND METHODS OF USE THEREOF

(71) Applicant: Kineta, Inc., Seattle, WA (US)

(72) Inventors: Shawn P. Iadonato, Seattle, WA (US); Kristin M. Bedard, Seattle, WA (US); Kerry W. Fowler, Seattle, WA (US); Ikenna Madu, Seattle, WA (US); Shari Kaiser, Seattle, WA (US)

(73) Assignee: Kineta, Inc., Seattle, WA (US)

( * ) Notice: Subject to any disclaimer, the term of this patent is extended or adjusted under 35 U.S.C. 154(b) by 0 days.

(21) Appl. No.: 15/308,058

(22) PCT Filed: May 8, 2015

(86) PCT No.: PCT/US2015/030014
§ 371 (c)(1),
(2) Date: Oct. 31, 2016

(87) PCT Pub. No.: WO2015/172099
PCT Pub. Date: Nov. 12, 2015

(65) Prior Publication Data
US 2017/0057978 A1    Mar. 2, 2017

Related U.S. Application Data

(60) Provisional application No. 61/991,418, filed on May 9, 2014, provisional application No. 62/177,900, filed on Mar. 25, 2015.

(51) Int. Cl.
| | | |
|---|---|---|
| C07D 277/82 | (2006.01) | |
| C07D 417/04 | (2006.01) | |
| C07D 417/06 | (2006.01) | |
| C07D 417/12 | (2006.01) | |
| C07D 513/04 | (2006.01) | |

(52) U.S. Cl.
CPC ......... *C07D 513/04* (2013.01); *C07D 277/82* (2013.01); *C07D 417/04* (2013.01); *C07D 417/06* (2013.01); *C07D 417/12* (2013.01)

(58) Field of Classification Search
None
See application file for complete search history.

(56) References Cited

U.S. PATENT DOCUMENTS

| | | |
|---|---|---|
| 2008/0039629 A1 | 2/2008 | Ramesh et al. |
| 2013/0217699 A1 | 8/2013 | An et al. |

FOREIGN PATENT DOCUMENTS

| | | |
|---|---|---|
| WO | 01/027096 A1 | 4/2001 |
| WO | 2011/106273 A1 | 9/2011 |
| WO | 2013/049407 A2 | 4/2013 |

OTHER PUBLICATIONS

STN Registry database entry for CAS RN 313404-26-1, Entered STN Jan. 10, 2001, Accessed Jun. 28, 2017.*
Schickli et al., Human Vaccines, vol. 5, Issue 9, pp. 582-591, Sep. 2009.*
"CHEMBL2070836—Compound Summary (CID 1160318)," PubChem Chemical Database, <https://pubchem.ncbi.nlm.nih.gov/compound/1160318#section=Top> [retrieved Jul. 18, 2015], 13 pages.
"N-(2-benzamido-1,3-benzothiazol-6-yl)benzamide—Compound Summary (CID 1548136)," PubChem Chemical Database, <https://pubchem.ncbi.nlm.nih.gov/compound/1548136#section=Top> [retrieved Jul. 18, 2015], 12 pages.
"N-(6-piperidin-1-ylsulfonyl-1,3-benzothiazol-2-yl)naphthalene-2-carboxamide (CID 4219163)," PubChem Chemical Database, <https://pubchem.ncbi.nlm.nih.gov/compound/4219163#section=Top> [retrieved Jul. 16, 2015], 10 pages.
International Search Report and Written Opinion dated Aug. 12, 2015, issued in International Application No. PCT/US15/30014, filed May 8, 2015, 9 pages.

* cited by examiner

*Primary Examiner* — Alicia L Otton
(74) *Attorney, Agent, or Firm* — Christensen O'Connor Johnson Kindness PLLC

(57) ABSTRACT

Disclosed herein are compounds, pharmaceutical compositions, and related methods for the treatment of viral infection, including RNA viral infection in subjects. The compounds, pharmaceutical compositions, and methods can modulate the innate immune antiviral response in vertebrate cells, including activating the RIG-I pathway.

14 Claims, 18 Drawing Sheets

| R3 | R1 | R2 | 10 μM | 5 μM | 1 μM |
|---|---|---|---|---|---|
| 3-Br-phenyl | ⊱ | H | ++ | + | - |
| 4-Cl-phenoxyethyl | ⊱ | H | + | - | - |
| 4-(N,N-dimethylsulfamoyl)phenyl | ⊱ | H | - | + | - |
| 3,5-diCl-phenyl | H | H | ++ | + | - |
| benzo[d][1,3]dioxol-5-yl | H | H | ++ | - | - |
| 3-Br-phenyl | ⊱ | ⊥ | + | - | - |
| naphthalen-2-yl | H | H | +++ | ++ | - |
| 2-(dimethylamino)ethylamino | ⊱ | H | +++ | ++ | - |
| 2-morpholinoethylamino | ⊱ | H | ++ | - | - |
| quinolin-3-yl | H | H | +++ | - | - |

Activity against EBOV at 5uM

FIG. 12

ANTI-VIRAL COMPOUNDS, PHARMACEUTICAL COMPOSITIONS, AND METHODS OF USE THEREOF

CROSS REFERENCE TO RELATED APPLICATIONS

This application is a national stage of International Application No. PCT/US2015/030014, filed May 8, 2015, which claims the benefit of U.S. Provisional Application No. 61/991,418 filed on May 9, 2014, and U.S. Provisional Application No. 62/177,900, on Mar. 25, 2015, each of which is incorporated by reference herein in their entirety.

FIELD OF THE DISCLOSURE

Compounds, pharmaceutical compositions, and methods disclosed herein are useful for treating viral infection, including RNA viral infection, in subjects.

BACKGROUND OF THE DISCLOSURE

As a group, RNA viruses represent an enormous public health problem in the U.S. and worldwide. Well-known RNA viruses include influenza virus (including the avian and swine isolates; also referred to herein as flu), Hepatitis C virus (HCV), Dengue virus (DNV), West Nile virus (WNV), SARS-coronavirus (SARS), MERS-coronavirus (MERS), respiratory syncytial virus (RSV), and human immunodeficiency virus (HIV). These viruses are responsible for pandemic outbreaks and threats to public health that have occurred throughout history. Flaviviruses, Henipaviruses, Filoviruses, and Arenaviruses are among emerging RNA viruses that pose significant public health and biodefense threats. These viruses collectively place hundreds of millions of people at risk of infection throughout the world. Many of the emerging RNA viruses cause viral hemorrhagic fever and can result in significant morbidity and mortality. Dengue virus (DNV) and West Nile virus (WNV) are both Flaviviruses (positive strand RNA virus) and Arboviruses, transmitted through mosquitoes; thus these viruses represent a potent potential biological threat through their ability to transmit readily among insects or animals and humans, high infectivity, and their potential to be weaponized in bioterror events.

At least 4 subtypes of Ebola virus (EV) are infectious to humans (Zaire, Sudan, Bundibugyo, and Cote d'lvoire). EV outbreaks have been described in Africa with a fatality rate of up to 90%. Feldmann, H., et al. (2011) Lancet 49, 1-14. Cases of EV infection have been reported in other countries including, very recently, the United States. The natural host for EV is not defined, but nonhuman primates (NHP) are susceptible. EV is a negative-strand RNA virus of the Filoviridae and can be spread effectively from person-to-person.

Seasonal flu infects 5-20% of the population annually, resulting in 200,000 hospitalizations and 36,000 deaths. Influenza can precipitate viral or secondary bacterial pneumonia, and complicated disease in those at the extremes of age or with weakened immune systems. Coronaviruses are common throughout the world and typically cause mild to moderate respiratory illness, although certain coronaviruses cause severe respiratory illness and death. A 2003 multi-country outbreak of SARS-coronavirus infection resulted in approximately 8,000 infections and nearly 800 deaths. Recently there have been reported cases of Middle East Respiratory Syndrome caused by MERS-coronavirus.

More than 170 million people worldwide are infected by HCV, and 130 million of these are chronic carriers at risk of developing chronic liver diseases (cirrhosis, carcinoma, and liver failure). As such, HCV is responsible for two thirds of all liver transplants in the developed world. Recent studies show that the death rate from HCV infection is rising due to the increasing age of chronically infected patients.

DNV is the most prevalent flavivirus in humans, is endemic in most tropical and subtropical countries, and is currently emerging elsewhere including the U.S. and across the Pacific Islands. DNV circulates as 4 serotypes (DNV1-4) and following a first infection, re-infection can lead to fatal hemorrhagic fever and shock syndrome. Infection is believed to provide life-long immunity against reinfection by the same serotype, but not against other serotypes. Epidemic outbreaks have been reported in many countries throughout Latin America, South-East Asia, and the Western Pacific Regions. It is estimated that between 50 and 100 million cases of Dengue fever occur globally each year. Dengue Hemorrhagic Fever and Dengue Shock Syndrome represent severe forms of the disease. Currently there is no specific antiviral therapy to treat DNV infection and no approved vaccine.

WNV is a related flavivirus that is endemic in regions of Africa and Asia, but is now emerging in the Western hemisphere. WNV is neuroinvasive to cause serious encephalitis disease and is lethal in about 6% of cases. Neuroinvasive WNV can present as meningitis, encephalitis or less frequently a flaccid paralysis referred to as poliomyelitis. WNV was largely absent from North America prior to 1999, but reemerged on the continent following an isolated outbreak of encephalitis in New York. In the subsequent 7 years, WNV infection spread throughout the 48 contiguous United States, and current estimates suggest as many as 2-3 million Americans have been infected. Over the past 20 years, outbreaks have been reported in parts of Europe, North Africa, the Middle East, and North America. Currently there is no specific antiviral therapy to treat WNV infection and no approved vaccine.

Among the RNA viruses listed, very few vaccines are currently approved for clinical use. One such vaccine exists for influenza virus, which must be revised and administered annually. Accordingly, drug therapy is essential to mitigate the significant morbidity and mortality associated with these viruses. Unfortunately, the number of antiviral drugs is limited, many are poorly effective, and nearly all are plagued by the rapid evolution of viral resistance and a limited spectrum of action. Ribavirin, a guanine nucleoside analog, has been studied in clinical trials of diverse RNA virus infections and is likely the most broadly acting antiviral agent available. Ribavirin is approved to treat Hepatitis C virus (HCV) and respiratory syncytial virus (RSV) infection, and Lassa virus related mortality was shown to be reduced with intravenous ribavirin treatment. However, it is weakly effective as a single agent and has significant hematologic toxicity. Both classes of acute influenza antivirals, adamantanes and neuraminidase inhibitors, are only effective within the first 48 hours after infection, thereby limiting the window of opportunity for treatment. High resistance to adamantanes already restricts their use, and massive stockpiling of neuraminidase inhibitors will eventually lead to overuse and the emergence of resistant strains of influenza.

Based on the foregoing, there is an immense and unmet need for effective treatments against viral infections. Most drug development efforts against viruses target viral proteins. RNA viruses have small genomes, with many encoding less than a dozen proteins, resulting in a very limited number of viral targets for new drugs. This is a large part of the reason that current drugs are narrow in spectrum and subject to the emergence of viral resistance. However, there is benefit to discovery of new viral targets for inhibition. Alternatively, direct-acting antiviral therapy can work to counteract any infection mechanisms such as viral entry into a host cell.

New antiviral therapy can act directly against viruses. In particular, new antiviral therapy can exploit the fact that these viruses are susceptible to control by innate intracellular immune defenses that function to suppress virus replication and spread. Compounds that act on cellular targets are likely to be more effective, be less susceptible to the emergence of viral resistance, cause fewer side effects, and be effective against a range of different viruses. An effective broad-spectrum antiviral, whether used on its own or in combination with other therapies, would be an enormous benefit to current clinical practice. While interferon is in principal host-mediated and broad spectrum, many viruses have evolved the ability to disrupt interferon signaling downstream of drug action at the receptor. An important criterion is the development of drugs that activate innate immune signaling below specific virus countermeasures and are a unique addition to conventional antiviral compounds in development or on the market. As one such innate immune antiviral response, the RIG-I-like receptor (RLR) pathway of innate antiviral immunity can impose a potent blockade to RNA virus infection through the actions of a variety of antiviral defense genes.

SUMMARY OF THE DISCLOSURE

The compounds, pharmaceutical compositions, and methods disclosed herein shift the focus of viral drug development away from the targeting of viral proteins to the targeting and enhancing of the host's innate antiviral immune response. The present disclosure relates to compounds, pharmaceutical compositions including the compounds, and associated methods of use to treat viral infection, including RNA viral infection. In certain embodiments, the compounds modulate the RIG-I pathway.

Embodiments of the present disclosure can provide compounds represented by the formula

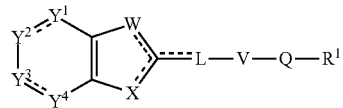

wherein L is $NR^2$, O, S, $C(=O)N$, $CR^2R^3CR^2R^3$, $CR^2R^3NR^2$, $CR^4=CR^4$, $CR^2R^3O$, $CR^2R^3S$, $NR^2CR^2R^3$, $NR^2C(=O)$, $NS(O)_t$, $OCR^2R^3$, $SCR^2R^3$;

V is $(CR^2R^3)_u$, $C(=O)CR^2R^3$, $CR^2R^3O$, $CR^2R^3OCR^2R^3$, $CR^4=CR^4$, $C\equiv C$, $C(=NR^2)$, or $C(=O)$;

Q is $NR^2$, O, $S(O)_t$, or a bond;

t=0, 1, 2; u=0-3;

wherein a dashed line indicates the presence or absence of a bond;

$R^1$ is $R^a$, $OR^2$, or $NR^2R^3$;

each $R^a$ is independently H, optionally substituted hydrocarbyl, optionally substituted aryl, optionally substituted heteroaryl;

$R^2$ and $R^3$ are each independently $R^a$, $C(=O)R^a$, $SO_2R^a$, or $R^2$ and $R^3$ form an optionally substituted carbocyclic, heterocarbocyclic, aryl, or heteroaryl ring;

each $R^4$ is independently $R^2$, $OR^a$, $C(=O)R^a$, $C(=O)NR^2R^3$, $NR^2R^3$, $NR^b(=O)R^a$, $SR^a$, $SOR^a$, $SO_2R^a$, $SO_2NHR^a$, $SO_2NR^2R^3$, $NCOR^a$, halogen, trihalomethyl, CN, $S=O$, nitro, or two $R^4$ groups form an optionally substituted carbocyclic, heterocarbocyclic, aryl, or heteroaryl ring;

W and X are each independently N, $NR^a$, $NR^5$, O, S, $CR^2R^4$ or $CR^4$;

$R^5$ is $R^a$, $C(=O)R^a$, $SO_2R^a$, or is not present;

$Y^1$, $Y^2$, $Y^3$ and $Y^4$ are each independently $CR^4$ or N; and $NR^2R^3$ may form an optionally substituted heterocylic or heteroaryl ring including pyrrolidine, piperidine, morpholine, and piperazine.

In some embodiments, compounds can be represented by the formula

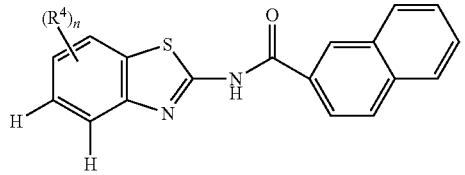

wherein $R^4$ is $R^d$, $SO_2R^d$, $C(=O)R^d$, NH $C(=O)R^d$, $R^e$, $OR^e$, or $CF_3$, wherein $R^c$ is H or $C_1$-$C_{10}$ hydrocarbyl, $R^d$ is unsubstituted heterocyclic or unsubstituted carbocyclic, and $R^e$ is substituted heteroaryl or substituted phenyl; and n is 1 or 2.

Some embodiments of the present disclosure can include a pharmaceutical composition including any of the compounds as described herein.

In addition, embodiments of the present disclosure can include methods of treating a viral infection in a subject including administering to the subject a therapeutically effective dose of a pharmaceutical composition as described herein thereby treating the viral infection in the subject.

Further, embodiments of the methods of the present disclosure can include administering any of the pharmaceutical compositions described herein as an adjuvant for a prophylactic or therapeutic vaccine.

Embodiments of the present disclosure include methods of modulating the innate immune response in a eukaryotic cell, including administering to the cell any of the compounds as described herein. In some embodiments the cell is in vivo. In other embodiments the cell is in vitro.

BRIEF DESCRIPTION OF THE DRAWINGS

In FIG. 1A, the high-throughput screen "hit" compound, compound 1 of Table 1, was validated by demonstrating dose-dependent induction of the IFNβ-luciferase (IFNβ-LUC, left), ISG56-luciferase (ISG56-LUC, center), and the ISG54-luciferase (ISG54-LUC, right) reporter genes. RLU=relative luciferase units. FIG. 1B confirms the specificity of compound 1, 10 μM of which (compound 1) does not induce the non-specific β-actin promoter relative to vehicle control (DMSO), and in contrast to equivalent dose of a positive control compound (CPD X). FIG. 1C shows HeLa cells treated with increasing amounts of compound 1 showed dose-dependent increase in interferon regulatory factor (IRF)-3 translocation to the nucleus, quantified by nuclear intensity minus cytoplasmic intensity ("normalized nuclear intensity"). FIG. 1D shows HeLa cells treated with increasing amounts of compound 1 showed dose-dependent increase in NFκB translocation, quantified by nuclear intensity minus cytoplasmic intensity. "SeV" refers to Sendai virus infection, the positive control.

FIG. 2A shows gene expression levels of IFIT2 (left) and OAS1 (right) in HeLa cells over time from 4-24 hours post treatment with 10 µM compound 1 (grey; OAS1 only) or 10 µM compound 2 (black; IFIT2 and OAS1 both shown). FIG. 2B shows gene expression levels of IFIT2 in PH5CH8 cells (solid color bars) and HeLa cells (black checked bars) treated with 10 µM compound 1 (CPD 1) or compound 2 (CPD 2). FIG. 2C shows gene expression levels of IFIT2 (left), OAS1 (center), and MxA (right) in primary HUVEC cells that were treated with 1 µM compound 1 (CPD 1) or 1 µM compound 2 (CPD 2).

FIG. 3A shows IFIT2 gene expression was induced by 5 µM compound 3 or compound 7. FIG. 3B shows compound 3 induced innate immune gene expression in mouse macrophage cells.

FIG. 10A, administration of compound 3 of Table 1 via oral (PO) or intravenous (IV) route resulted in detectable levels of compound in serum samples obtained up to 250 minutes post treatment. FIG. 10B, at 4 hours post treatment of compound 3 and compound 7 of Table 1, there was detectable compound in lung tissue.

FIG. 11C virus was decreased in the lung of animals treated with compound 3.

Figure 12:
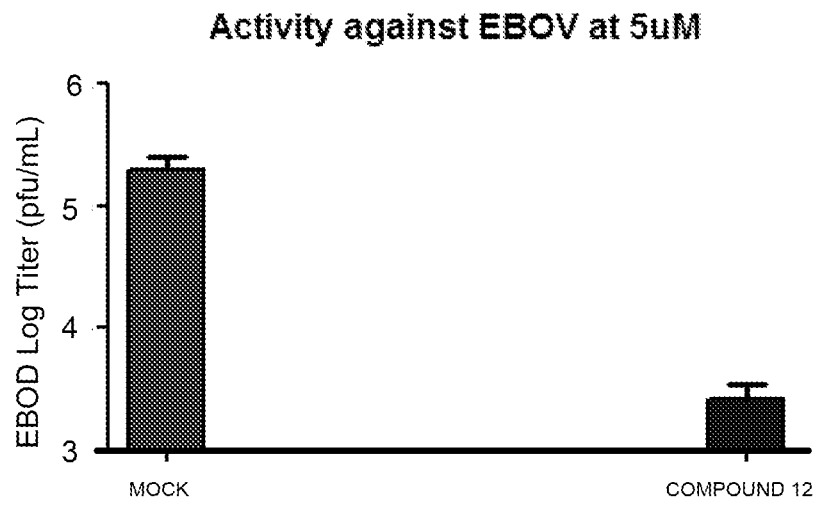

FIG. 12 shows the in vitro activity of compound 12 of Table 1 of the disclosure against EBOV at 5 µM, showing greater than a 2 log reduction in EBOV titer in vitro.

DETAILED DESCRIPTION

Figure 1A:
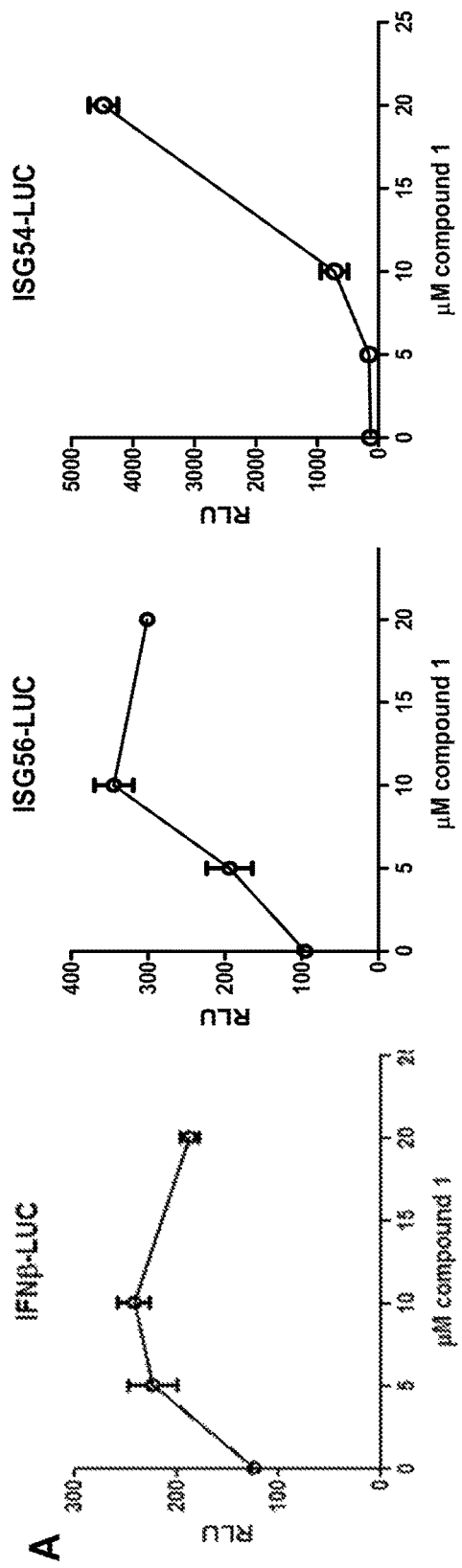
FIGS. 1A-1D show in vitro biological activity.

The present disclosure provides compounds, pharmaceutical compositions, and methods that shift the focus of viral treatments away from the targeting of viral proteins to targeting and enhancing the host (subject's) innate antiviral response. Such compounds, pharmaceutical compositions, and methods are likely to be more effective, less susceptible to the emergence of viral resistance, cause fewer side effects, and be effective against a range of different viruses.

The retinoic acid-inducible gene 1 (RIG-I) pathway is intimately involved in regulating the innate immune response to virus infections including RNA virus infections. RIG-I is a cytosolic pathogen recognition receptor that is essential for triggering immunity to a wide range of RNA viruses. RIG-I is a double-stranded RNA helicase that binds to motifs within the RNA virus genome characterized by homopolymeric stretches of uridine or polymeric UM motifs. Binding to RNA induces a conformation change that relieves RIG-I signaling repression by an autologous repressor domain, thus allowing RIG-I to signal downstream through its tandem caspase activation and recruitment domains (CARDs). RIG-I signaling is dependent upon its NTPase activity, but does not require the helicase domain. RIG-I signaling is silent in resting cells, and the repressor domain serves as the on-off switch that governs signaling in response to virus infection.

Without being bound by a theory or particular mechanism of action, RIG-I signaling is transduced through IPS-1 (also known as Cardif, MAVs, and VISA), an essential adaptor protein that resides in the outer mitochondrial membrane. IPS-1 recruits a macromolecular signaling complex that stimulates the downstream activation of IRF-3, a transcription factor that induces the expression of type I interferons (IFNs) and virus-responsive genes that control infection. Compounds that trigger RIG-I signaling directly or through modulation of RIG-I pathway components, including IRF-3, present attractive therapeutic applications as antivirals or immune modulators.

In certain embodiments, a high-throughput screening approach was used to identify compounds that modulate the RIG-I pathway. In particular embodiments, validated RIG-I agonist lead compounds were demonstrated to specifically activate IRF-3. In additional embodiments, the compounds have one or more of the following advantages: induce expression of interferon-stimulated genes (ISGs low cytotoxicity in cell-based assays, suitable for analog development and SAR studies, drug-like physiochemical properties, and/or antiviral activity against viruses including Dengue virus (DNV), human coronavirus (SARS and MERS-like pathogen), influenza A virus, respiratory syncytial virus (RSV), and/or Hepatitis C virus (HCV). In additional embodiments, the compounds exhibit antiviral activity against dsDNA viruses including human cytomegalovirus. In certain embodiments, the compounds exhibit all of these characteristics.

The disclosed compounds represent a new class of antiviral therapeutics. Although the disclosure is not bound by a specific mechanism of action of the compounds in vivo, the compounds are selected for their modulation of innate immune antiviral responses. In certain embodiments, the modulation is activation of the RIG-I pathway. Compounds, pharmaceutical compositions, and methods disclosed herein function to decrease one or more of: viral protein, viral RNA, and infectious virus in laboratory models of viral infection.

The disclosure herein relates to a class of compounds represented by Formula 1.

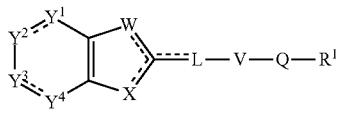

Formula 1 wherein L can be $NR^2$, O, S, $C(=O)N$, $CR^2R^3CR^2R^3$, $CR^2R^3NR^2$, $CR^4=CR^4$, $CR^2R^3O$, $CR^2R^3S$, $NR^2CR^2R^3$, $NR^2C(=O)$, $NS(O)_t$, $OCR^2R^3$, $SCR^2R^3$;
V is $(CR^2R^3)_u$, $C(=O)CR^2R^3$, $CR^2R^3O$, $CR^2R^3OCR^2R^3$, $CR^4=CR^4$, $C\equiv C$, $C(=NR^2)$, or $C(=O)$;
Q can be $NR^2$, O, $S(O)_t$, or a bond;
t=0, 1, 2; u=0-3;
wherein a dashed line indicates the presence or absence of a bond; $R^1$ can be $R^a$, $OR^2$ or $NR^2R^3$; each $R^a$ can independently be H, optionally substituted hydrocarbyl, optionally substituted aryl, optionally substituted heteroaryl; $R^2$ and $R^3$ can each independently be $R^a$, $C(=O)R^a$, or $SO_2R^a$, $R^2$ and $R^3$ can form an optionally substituted carbocyclic, heterocarbocyclic, aryl or heteroaryl ring; each $R^4$ can independently be $R^2$, $ORE$, $C(=O)R^a$, $C(=O)NR^2R^3$, $NR^2R^3$, $NR^b(=O)R^a$, $SR^a$, $SOR^a$, $SO_2R^a$, $SO_2NHR^a$, $SO_2NR^2R^3$, $NCOR^a$, halogen, trihalomethyl, CN, S=O, or nitro; W and X can each independently be N, $NR^a$, $NR^5$, O, S, $CR^2R^4$ or $CR^4$; $R^5$ can be $R^a$, $C(=O)R^a$, $SO_2R^a$, or is not present; $Y^1$, $Y^2$, $Y^3$ and $Y^4$ can each independently be $CR^4$ or N; and $NR^2R^3$ can form an optionally substituted heterocylic or heteroaryl ring including, but not limited to, pyrrolidine, piperidine, morpholine, and piperazine.

In an embodiment, with respect to Formula 1, $Y^1$ can be $CR^4$ or N. For example, $Y^1$ can be $CR^4$.

In an embodiment, with respect to Formula 1, $Y^2$ can be $CR^4$ or N. For example, $Y^2$ can be $CR^4$.

In an embodiment, with respect to Formula 1, $Y^2$ can be $CR^4$ or N. For example, $Y^3$ can be $CR^4$.

In an embodiment, with respect to Formula 1, $Y^1$ and $Y^2$ can both be $CR^4$, and in some instances, $Y^1$ and $Y^2$ can form a fused heterocyclic ring optionally substituted by $R^6$ as shown below:

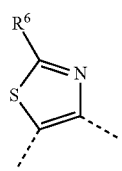

wherein $R^6$ can be H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. For example, $R^6$ can be H or $CH_3$.

In an embodiment, with respect to Formula 1, $Y^3$ and $Y^4$ can be $CR^4$ or N. For example, $Y^3$ and $Y^4$ can be $CR^4$.

In an embodiment, with respect to Formula 1, $Y^1$, $Y^2$, $Y^3$ and $Y^4$ can be $CR^4$. In some instances, $Y^1$, $Y^2$, $Y^3$ and $Y^4$ can be CH. In some instances, $Y^1$ and $Y^2$ can form a fused heterocyclic ring optionally substituted by $R^6$, as shown above, and $Y^3$ and $Y^4$ can be CH.

The disclosure also relates to a class of compounds represented by Formula 1A.

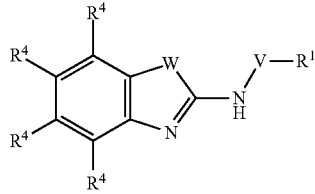

Formula 1A wherein W can be O or S; and $R^1$ can be $R^a$, $OR^2$, or $NR^2R^3$. $R^1$, $R^2$, $R^3$, $R^4$, $R^a$, and V and W, can be as defined above with respect to Formula 1. In an embodiment, each $R^a$ can independently be H, optionally substituted hydrocarbyl, optionally substituted aryl, optionally substituted heteroaryl; $R^2$ and $R^3$ can each independently be $R^2$, COW, or $SO_2R^a$; each $R^4$ can independently be $R^2$, $OR^a$, $NR^2R^3$, $SR^a$, $SOR^a$, $SO_2R^a$, $SO_2NHR^a$, $NCOR^a$, $C(=O)R^a$, $CONR^2R^3$, halogen, trihalomethyl, CN, S=O, or nitro; V can be $CR^2R^3$, $C(=O)$, $C(=O)CR^2R^3$, or $C(=N)R^2$; and W can be O or S. In some instances, V can be C=O, and $R^1$ can be an optionally substituted aryl, or an optionally substituted heteroaryl. For example, $R^1$ can be optionally substituted phenyl, or $R^1$ can be optionally substituted naphthyl.

The disclosure also relates to a class of compounds represented by Formula 1B.

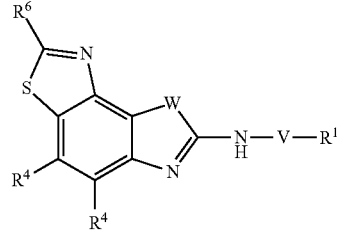

Formula 1B wherein W can be O or S; and $R^1$ can be $R^a$ or $NR^2R^3$. $R^1$, $R^2$, $R^3$, $R^4$, $R^6$, $R^a$, and V are as defined above with respect to Formula 1.

In some instances, V can be C=O, and $R^1$ can be an optionally substituted aryl, or an optionally substituted heteroaryl. For example, $R^1$ can be optionally substituted phenyl, or $R^1$ can be optionally substituted naphthyl.

The disclosure also relates to a class of compounds represented by Formula 1C.

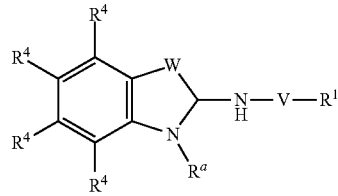

Formula 1C wherein W can be O or S; and $R^1$ can be $R^a$, $OR^2$, or $NR^2R^3$. $R^1$, $R^2$, $R^3$, $R^4$, $R^a$, and V and W, are as defined above with respect to Formula 1. In an embodiment, each $R^a$ can independently be H, optionally substituted hydrocarbyl, optionally substituted aryl, optionally substituted heteroaryl; $R^2$ and $R^3$ can each independently be $R^a$, $C(\!=\!O)R^a$, or $SO_2R^a$; each $R^4$ can independently be $R^2$, $OR^a$, $NR^2R^3$, $SR^a$, $SOR^a$, $SO_2R^a$, $SO_2NHR^a$, $NCOR^a$, $C(\!=\!O)R^a$, $CONR^2R^3$, halogen, trihalomethyl, CN, S=O, or nitro; V can be $CR^2R^3$, $C(\!=\!O)$, $C(\!=\!O)CR^2R^3$, or $C(\!=\!N)R^2$; and W can be O or S. In some instances, V can be C=O, and $R^1$ can be an optionally substituted aryl, or an optionally substituted heteroaryl. For example, $R^1$ can be optionally substituted phenyl, or $R^1$ can be optionally substituted naphthyl.

A class of compounds of interest can include compounds of Formula 1A, 1B, or 1C wherein $R^4$ can be H; and V can be C=O. Some embodiments can include compounds having Formula 1A, Formula, 1B, or Formula 1C wherein $R^1$ is optionally substituted phenyl or optionally substituted naphthyl. Various embodiments can include compounds having Formula 1A, Formula, 1B, or Formula 1C wherein W is S and X is N. Additional embodiments can include compounds having Formula 1A, Formula 1B, or Formula 1C wherein W is O and X is N.

The disclosure also includes a class of compounds represented by any one of Formulas 2-11.

Formula 2

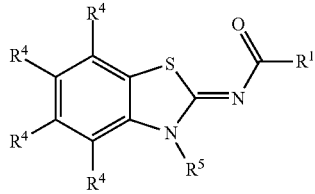

Formula 3

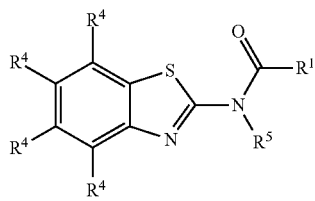

Formula 4

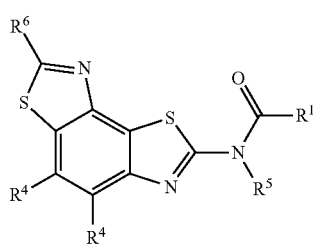

Formula 5

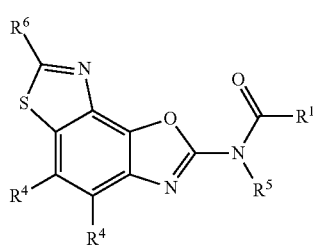

Formula 6

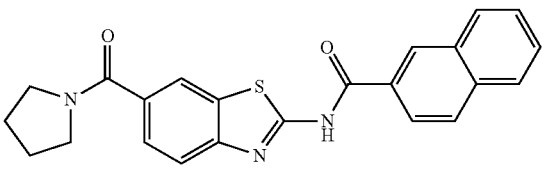

Formula 7

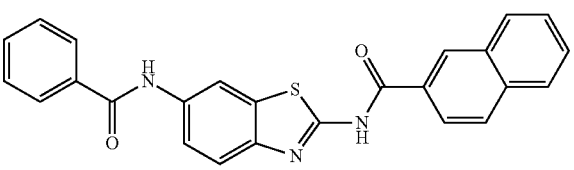

Formula 8

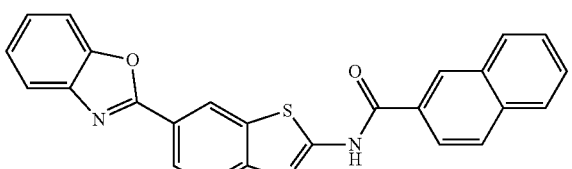

Formula 9

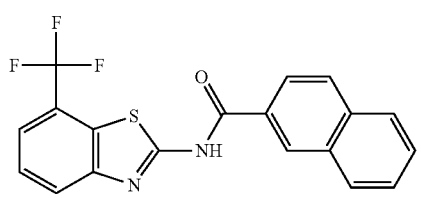

Formula 10

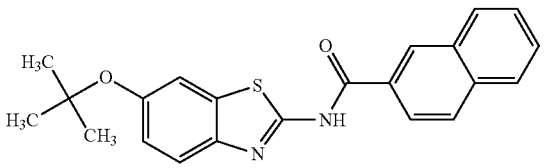

Formula 11

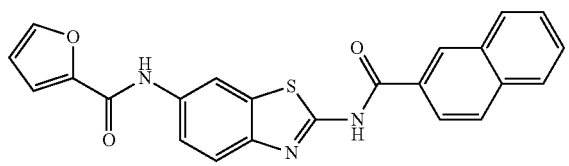

Formula 12

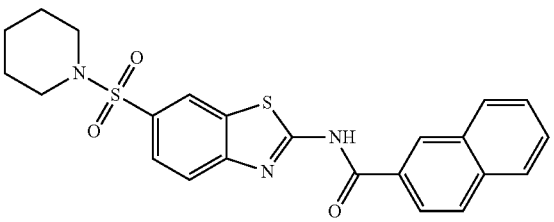

Embodiments can include compounds having Formula 4 wherein $R^1$ can be a phenyl group substituted by at least one halogen, a phenyl group substituted by $NR^2R^3$, a phenyl group substituted by $SO_2NR^2R^3$, $CR^2R^3ORd$, an unsubstituted naphthyl group, a naphthyl group substituted by $O(CR^2R^3)_nR^d$, $NR^a(CR^2R^3)_nR^d$, $NR^a(CR^2R^3)_nNR^2R^3$, a two membered ring structure including a pyridynyl group and a phenyl group, or a two membered ring structure including a phenyl group and a dioxolanyl group; each $R^a$ can independently be H or optionally substituted hydrocarbyl ($C_1$-$C_{10}$); $R^2$ and $R^3$ can each independently be $R^a$, $COR^a$, $(CH_2)_nO$, or $SO_2R^a$; each $R^4$ can independently be $R^a$; $R^d$ can be phenyl or morpholino; $R^5$ can be H or $CH_3$; $R^6$ can be H or $CH_3$; and wherein n can be 1, 2, 3, or 4.

Particular embodiments having Formula 4 can be represented by the compounds

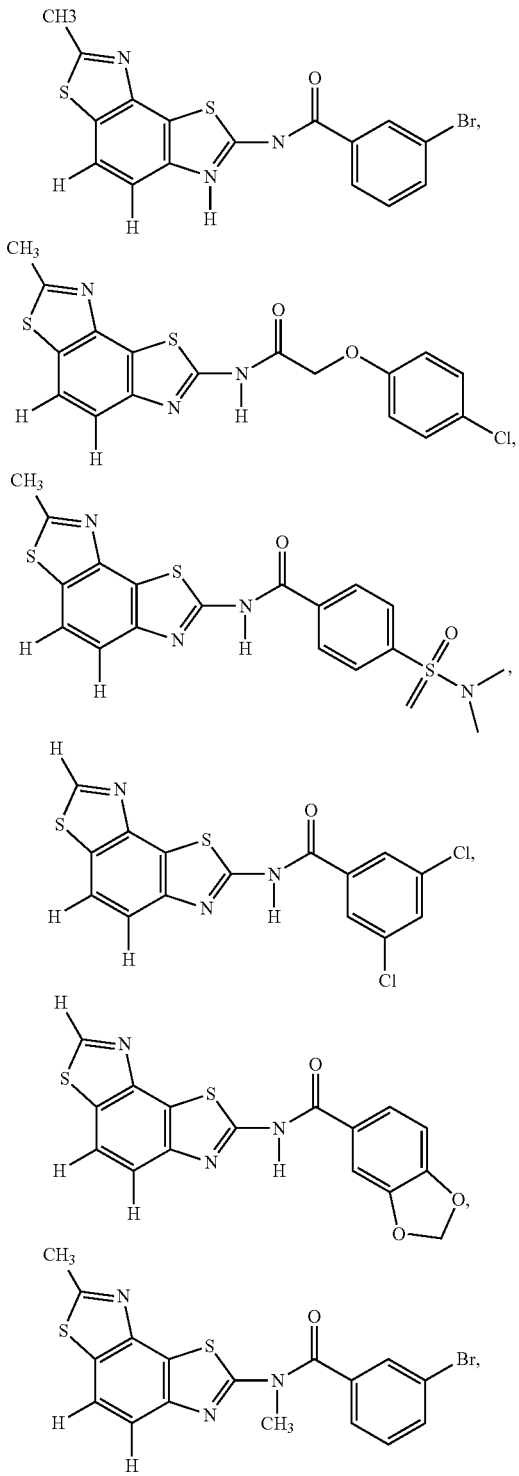

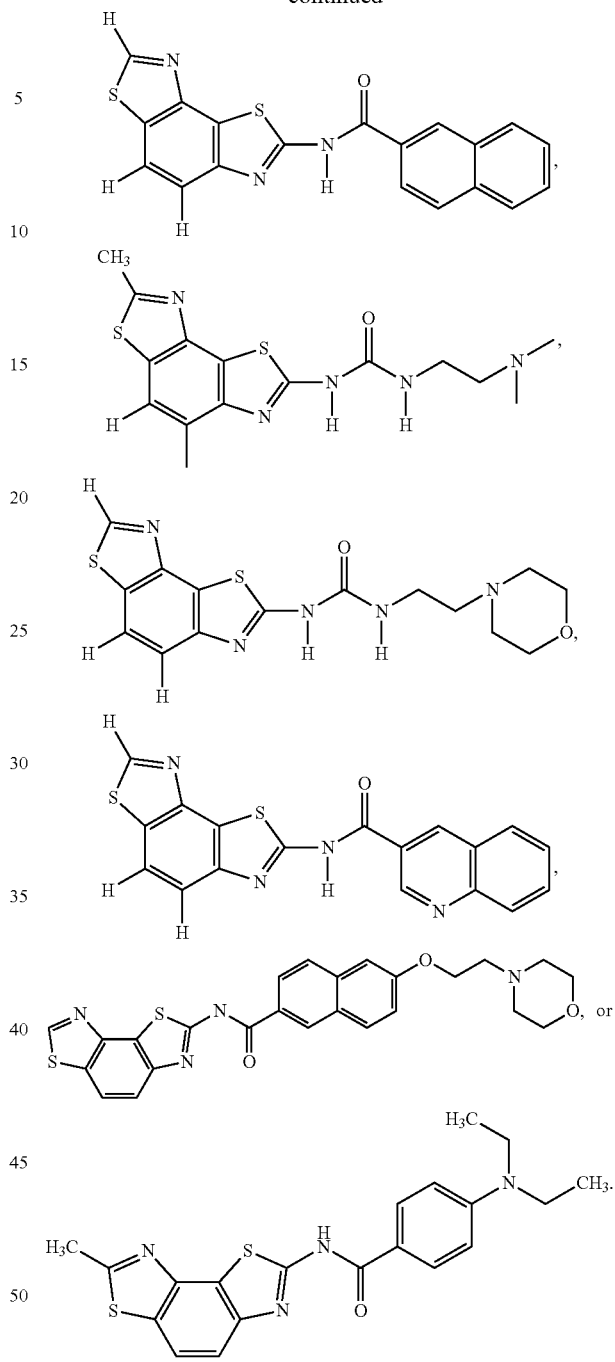

Embodiments can include compounds having Formula 5 wherein $R^1$ can be a phenyl group substituted by at least one halogen, a phenyl group substituted by $NR^2R^3$, a phenyl group substituted by $SO_2R^d$, a naphthyl group optionally substituted by $O(CR^2R^3)_nR^d$, or an unsubstituted naphthyl group, each $R^a$ can independently be H or optionally substituted $C_1$-$C_{10}$ hydrocarbyl; $R^2$, $R^3$ and each $R^4$ can independently be $R^a$, $R^d$ can optionally be substituted phenyl or optionally substituted morpholino; $R^5$ can be H or $CH_3$; $R^6$ can be H or $CH_3$, and wherein n can be 1, 2, 3, or 4.

Particular embodiments having Formula 4 can be represented by the compounds

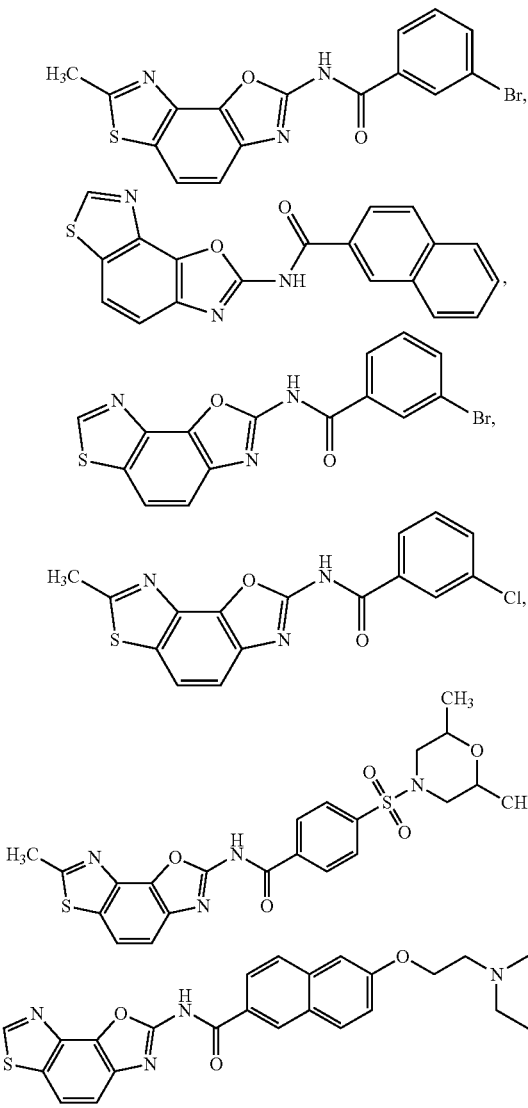

In various embodiments, a compound can be represented by the formula

Formula 1D

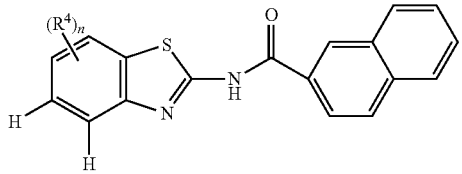

wherein $R^4$ can be $R^d$, $SO_2R^d$, $C(=O)R^d$, $NHC(=O)R^d$, $R^e$, $OR^c$, or $CF_3$, wherein $R^c$ can be H or $C_1$-$C_{10}$ hydrocarbyl, $R^d$ can be substituted heterocyclic, unsubstituted heterocyclic, or unsubstituted carbocyclic, and $R^e$ can be substituted heteroaryl or substituted phenyl; and n can be 1 or 2. In particular embodiments, $R^4$ can be $CF_3$, $OR^c$, or a phenyl group substituted by at least one $OCH_3$ group.

Additionally, some embodiments of Formula 1D can include compounds represented by

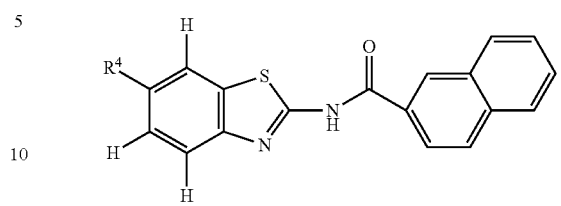

wherein $R^4$ can be: (i) $C(=O)R^d$ and $R^d$ is a pyrrolidonyl group, (ii) $SO_2R^d$ and $R^d$ is a piperidinyl group, (iii) $NHC(=O)R^d$ and $R^d$ is a phenyl group or a furanyl group, (iv) an imidazolyl group, or (v) a thiazole group.

Further, some embodiments of Formula 1D can include compounds represented by

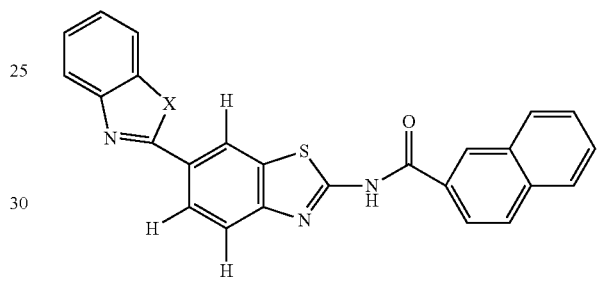

wherein X can be NH or O.

Embodiments of Formula 1D can include compounds represented by

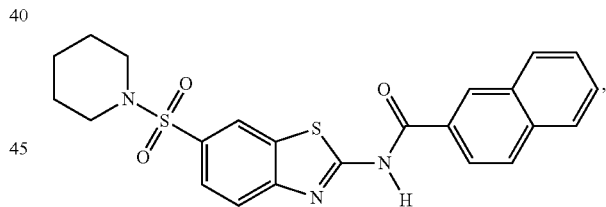

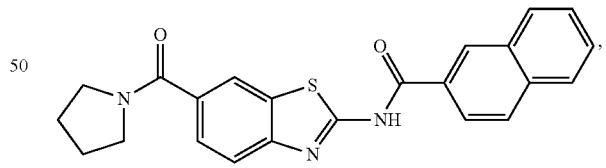

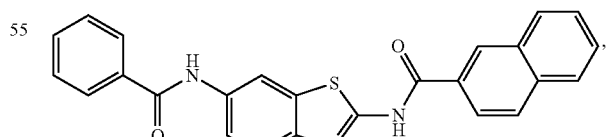

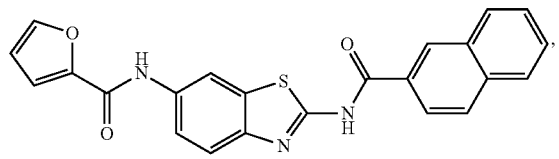

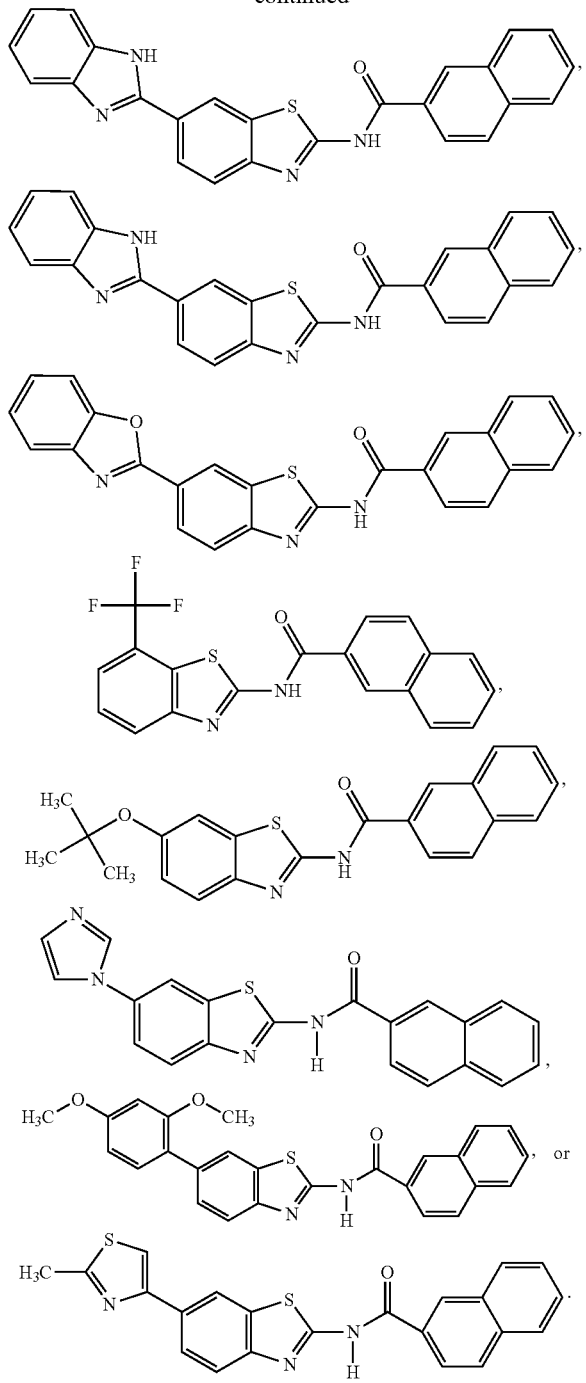

In an embodiment, compounds can be represented by the formula

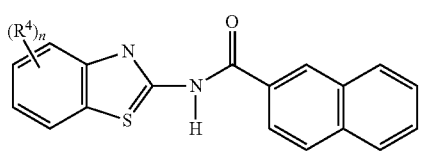

wherein each $R^4$ can independently be $R^2$, $OR^a$, $NR^2R^3$, $SR^a$, $SOR^a$, $SO_2R^a$, $SO_2NHR^a$, $NCOR^a$, $C(=O)R^a$, $CONR^2R^3$, halogen, trihalomethyl, CN, S=O, or nitro and n=1-4. In some embodiments, $R^4$ can be optionally substituted heteroaryl. Additionally, $R^4$ can be optionally substituted heteroaryl and n can be 1. In various embodiments, compounds can be represented by the formula

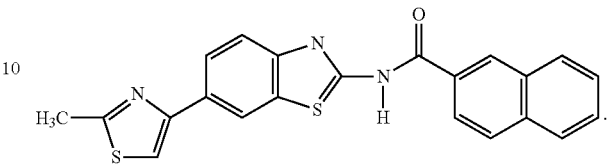

With respect to any relevant structural feature herein, each $R^a$ can independently be H; optionally substituted hydrocarbyl, such as $C_{1-12}$ or $C_{1-6}$ hydrocarbyl; optionally substituted aryl, such as optionally substituted $C_{6-12}$ aryl, including optionally substituted phenyl; optionally substituted heteroaryl, including optionally substituted $C_{2-12}$ heteroaryl, such as optionally substituted pyridinyl, optionally substituted furyl, optionally substituted thienyl, etc. In some embodiments, each Ra can independently be H, or $C_{1-12}$ alkyl, including: linear or branched alkyl having the formula $C_aH_{a+1}$, or cycloalkyl having the formula $C_aH_{a+1}$, wherein a is 1, 2, 3, 4, 5, 6, 7, 8, 9, 10, 11, or 12, such as linear or branched alkyl of the formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of the formula: $C_3H_5$, $C_4H_7$, $C_5H_9$, $C_6H_{11}$, $C_7H_{13}$, $C_8H_{15}$, $C_9H_{17}$, $C_{10}H_{19}$, etc.

With respect to Ra, in some embodiments, the aryl group can be substituted with halogen, trihalomethyl, alkoxy, alkylamino, OH, CN, alkylthio, arylthio, sulfoxide, arylsulfonyl, alkylsulfonyl, carboxylic acid, nitro or acylamino.

With respect to $R^a$, in some embodiments, the heteroaryl group can be single or fused. In some embodiments, the single heteroaryl group can be imidazole. In some embodiments, the fused heteroaryl group can be benzimidazole. In some embodiments, the heteroaryl group can be substituted with halogen, trihalomethyl, alkoxy, alkylamino, OH, CN, alkylthio, arylthio, sulfoxide, arylsulfonyl, alkylsulfonyl, carboxylic acid, nitro or acylamino. In some embodiments, the alkyl group can be branched, cyclic or polycyclic.

With respect to $R^a$, a hydrocarbyl can be alkyl, alkenyl, or alkynyl. In some embodiments, the alkyl group can be substituted with halogen, trihalomethyl, alkoxy, alkylamino, OH, CN, heteroaryl, alkylthio, arylthio, sulfoxide, arylsulfonyl, alkylsulfonyl, carboxylic acid, nitro, or acylamino. In some embodiments, the heteroaryl group can be single or fused. In some embodiments, the single heteroaryl group can be imidazole. In some embodiments, the fused heteroaryl group can be benzimidazole. In some embodiments, the alkenyl group can be branched, cyclic or polycyclic. In some embodiments, the alkenyl group can be substituted with halogen, trihalomethyl, alkoxy, alkylamino, OH, CN, heteroaryl, alkylthio, arylthio, sulfoxide, arylsulfonyl, alkylsulfonyl, carboxylic acid, nitro, or acylamino.

With respect to any relevant structural feature herein, $R^b$ can be H, or $C_{1-3}$ hydrocarbyl, such as $CH_3$, $C_2H_5$, $C_3H_7$, cyclopropyl, $CH=CH_2$, $CH_2CH=CH_2$, $C\equiv CH$, $CH_2C\equiv CH$, etc.

With respect to any relevant structural feature herein, $R^c$ can be H, or $C_{1-3}$ alkyl, such as $CH_3$, $C_2H_5$, $C_3H_7$, cyclopropyl, etc. In some embodiments, $R^c$ can be H.

With respect to any relevant formula or structural depiction herein, such as Formula 1, Formula 2, Formula 3, or Formula 4, $R^1$ can be $R^a$, $OR^2$ or $NR^2R^3$. In some embodiments, $R^1$ can be optionally substituted phenyl. In some embodiments, $R^1$ can be unsubstituted phenyl. In some embodiments, $R^1$ can be optionally substituted naphthyl. In some embodiments, $R^1$ can be unsubstituted naphthyl. In other embodiments, R1 can be

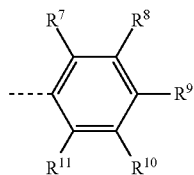

In some embodiments, $R^1$ can be.

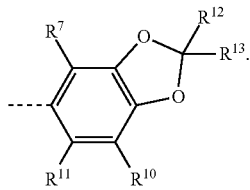

In some embodiments, $R^1$ can be

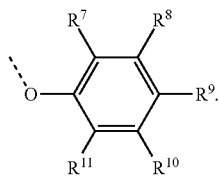

In some embodiments, $R^1$ can be

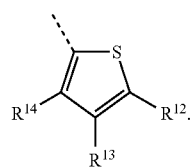

In some embodiments, $R^1$ can be

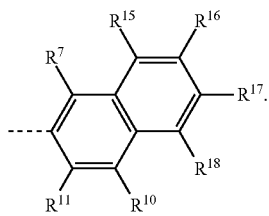

In some embodiments, $R^1$ can be

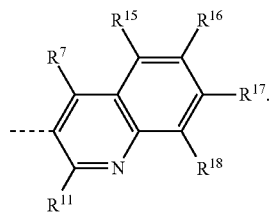

In some embodiments, $R^1$ can be

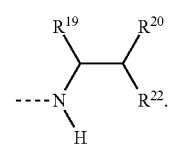

With respect to any relevant structural feature herein, $R^2$ can be $R^a$, $COR^a$, or $SO_2R^a$. In some embodiments, $R^2$ can be H, methyl, ethyl, a propyl (e.g. n-propyl, isopropyl, etc.), cyclopropyl, a butyl, cyclobutyl or an isomer thereof, a pentyl, cyclopentyl or an isomer thereof, a hexyl, a cyclohexyl or an isomer thereof, etc. In some embodiments, $R^2$ can be H.

With respect to any relevant structural feature herein, $R^3$ can be $R^a$, $C(=O)R^a$, or $SO_2R^a$. In some embodiments, $R^3$ can be H, methyl, ethyl, a propyl (e.g. n-propyl, isopropyl, etc.), cyclopropyl, a butyl, cyclobutyl or an isomer thereof, a pentyl, cyclopentyl or an isomer thereof, a hexyl, a cyclohexyl or an isomer thereof, etc. In some embodiments, $R^3$ can be H.

With respect to any relevant structural feature herein, each $R^4$ can independently be $R^2$, $OR^a$, $C(=O)R^a$, $CO_2R^a$, $OCOR^a$, $CONR^2R^3$, $NR^2R^3$, $NR^bC(=O)R^a$, $SR^a$, $SOR^a$, $SO_2R^a$, $SO_2NHR^a$, $SO_2NR^aR^b$, $NC(=O)R^a$, halogen, trihalomethyl, CN, S=O, nitro, or $C_{2-5}$ heteroaryl. In some embodiments, $R^4$ can be H.

Generally $R^5$ and $R^7$-$R^{22}$, can be H or any substituent, such as a substituent having from 0 to 6 carbon atoms and from 0 to 5 heteroatoms independently selected from: O, N, S, F, Cl, Br, and I, and/or having a molecular weight of 15 g/mol to 300 g/mol. Any of $R^5$ and $R^7$-$R^{22}$ can include: a) 1 or more alkyl moieties optionally substituted with, or optionally connected by, b) 1 or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or can be a substituent having no alkyl portion, such as F, Cl, Br, I, $NO_2$, CN, $NH_2$, OH, COH, $CO_2H$, etc.

With respect to any relevant structural feature herein, $R^5$ can be $R^a$, $COR^a$, $SO_2R^a$, or may not be present. Some examples of $R^5$ can include H or $C_{1-3}$ alkyl, such as $CH_3$, $C_2H_5$, $C_7$, cyclopropyl, etc. In some embodiments, $R^5$ can be $CH_3$. In some embodiments, $R^5$ is H.

With respect to any relevant formula or structural depiction above, some examples of $R^{19}$ can include $R^b$, $OR^b$, $SR^b$, $C(=O)R^b$, $CO_2R^b$, $OC(=O)R^b$, $NR^bR^c$, $C(=O)NR^bR^c$, $NR^bC(=O)R^c$, $SO_2NR^bR^c$, $CF_3$, CN, $NO_2$, F, Cl, Br, I, or $C_{2-5}$ heterocyclyl. In some embodiments, $R^{19}$ can be H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C=CH$, or $NO_2$. In some embodiments, $R^{19}$ can be H.

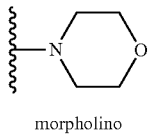 [SMILES: *N1CCOCC1]

morpholino

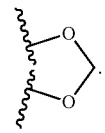

With respect to any relevant formula or structural depiction above, some examples of $R^5$ can include $R^b$, or as depicted below, $C(=O)R^b$, $CO_2R^b$, $C(=O)NR^bR^c$, $NR^bC(=O)R^c$, $SO_2NR^bR^c$, $CF_3$, CN, or $C_{2-5}$ heterocyclyl. In some embodiments, $R^5$ can be H, $CH_3$, $CH_2CH_3$, $SO_2NH_2$, or $CH_2C\equiv CH$. In some embodiments, $R^5$ can be H, $CH_3$, $CH_2CH_3$, $CH_2CH_2CH_3$, $CH_2CH=CH_2$, or $CH_2C\equiv CH$. In some embodiments, $R^5$ is $CH_2C\equiv CH$. In some embodiments, $R^5$ can be H.

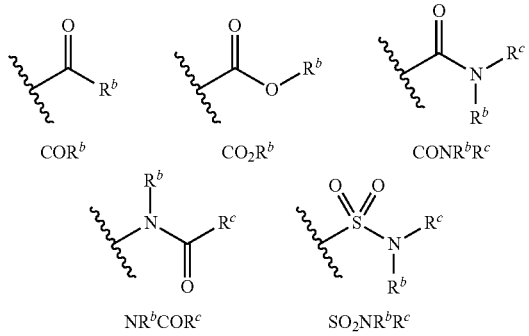

With respect to any relevant formula or structural depiction above, some examples of $R^7$ can include $R^b$, $OR^b$, $SR^b$, $C(=O)R^b$, $CO_2R^b$, $OC(=O)R^b$, $NR^bR^c$, $C(=O)NR^bR^c$, $NR^bC(=O)R^c$, $SO_2NR^bR^c$, $CF_3$, CN, $NO_2$, F, Cl, Br, I, or $C_{2-5}$ heterocyclyl. In some embodiments, $R^7$ can be H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^7$ can be H.

With respect to any relevant formula or structural depiction above, some examples of $R^8$ can include $R^b$, $OR^b$, $SR^b$, $C(=O)R^b$, $CO_2R^b$, $OC(=O)R^b$, $NR^bR^c$, $C(=O)NR^bR^c$, $NR^bC(=O)R^c$, $SO_2NR^bR^c$, $CF_3$, CN, $NO_2$, F, Cl, Br, I, or $C_{2-5}$ heterocyclyl. In some embodiments, $R^8$ can be H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^8$ can be H, Cl or Br. In some embodiments, $R^8$ can be Cl. In some embodiments, $R^8$ can be Br. In some embodiments, $R^8$ can be H.

With respect to any relevant formula or structural depiction above, some examples of $R^9$ can include $R^b$, $OR^b$, $SR^b$, $C(=O)R^b$, $CO_2R^b$, $OC(=O)R^b$, $NR^bR^c$, $C(=O)NR^bR^c$, $NR^bC(=O)R^c$, $SO_2NR^bR^c$, $CF_3$, CN, $NO_2$, F, Cl, Br, I, or $C_{2-5}$ heterocyclyl. In some embodiments, $R_9$ can be H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^9$ can be H, Cl, or $SO_2NH_2$. In some embodiments, $R^9$ can be H. In some embodiments, $R^9$ can be Cl. In some embodiments, $R^9$ can be $SO_2NH_2$. In some embodiments, $R^9$ can be H.

In some embodiments, $R^8$ and $R^9$ can be joined together to form:

With respect to any relevant formula or structural depiction above, some examples of $R^{10}$ can include $R^b$, $OR^b$, $SR^b$, $C(=O)R^b$, $CO_2R^b$, $OC(=O)R^b$, $NR^bR^c$, $C(=O)NR^bR^c$, $NR^bC(=O)R^c$, $SO_2NR^bR^c$, $CF_3$, CN, $NO_2$, F, Cl, Br, I, or $C_{2-5}$ heterocyclyl. In some embodiments, $R^{10}$ can be H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{10}$ can be H or Cl. In some embodiments, $R^{10}$ can be H. In some embodiments, $R^{10}$ can be Cl. In some embodiments, $R^8$ and $R^{10}$ can be Cl.

With respect to any relevant formula or structural depiction above, some examples of $R^{11}$ can include $R^b$, $OR^b$, $SR^b$, $C(=O)R^b$, $CO_2R^b$, $OC(=O)R^b$, $NR^bR^c$, $C(=O)NR^bR^c$, $NR^bC(=O)R^c$, $CF_3$, CN, $NO_2$, F, Cl, Br, or I. In some embodiments, $R^{11}$ can be H, $CH_3$, $CH_2CH_3$, Cl, Br, OH, $OCH_3$, $SCH_3$, $NH_2$, $NHCH_3$, $N(CH_3)_2$, $CH_2C\equiv CH$, or $NO_2$. In some embodiments, $R^{11}$ can be H.

In some embodiments, $R^7$ and $R^{11}$ can be H. In some embodiments, $R^7$, $R^9$, and $R^{11}$ can be H. In some embodiments, $R^7$, $R^{10}$, and $R^{11}$ can be H. In some embodiments, $R^7$, $R^8$, $R^{10}$, and $R^{11}$ can be H. In some embodiments, $R^7$, $R^8$, $R^9$, and $R^{11}$ can be H. In some embodiments, $R^7$, $R^8$, $R^9$, $R^{10}$, and $R^{11}$ can be H.

With respect to any relevant formula or structural depiction above, some examples of $R^{15}$ can include $R^b$, $OR^b$, $SR^b$, $C(=O)R^b$, $CO_2R^b$, $OC(=O)R^b$, $NR^bR^c$, $C(=O)NR^bR^c$, $NR^bC(=O)R^c$, $SO_2NR^bR^c$, $CF_3$, CN, $NO_2$, F, Cl, Br, or $C_{2-5}$ heterocyclyl. In some embodiments, $R^{15}$ can be H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{15}$ can be H.

With respect to any relevant formula or structural depiction above, some examples of $R^{16}$ can include $R^b$, $OR^b$, $SR^b$, $C(=O)R^b$, $CO_2R^b$, $OC(=O)R^b$, $NR^bR^c$, $C(=O)NR^bR^c$, $NR^bC(=O)R^c$, $SO_2NR^bR^c$, $CF_3$, CN, $NO_2$, F, Cl, Br, I, or $C_{2-5}$ heterocyclyl. In some embodiments, $R^{16}$ can be H, $CH_3$, $CH_2CH_3$, Cl, Br, OH, $OCH_3$, $SCH_3$, $NH_2$, $NHCH_3$, $N(CH_3)_2$, $SO_2NH_2$, $CH_2C\equiv CH$, or $NO_2$. In some embodiments, $R^{16}$ can be H.

With respect to any relevant formula or structural depiction above, some examples of $R^{17}$ can include $R^b$, $OR^b$, $SR^b$, $C(=O)R^b$, $CO_2R^b$, $OC(=O)R^b$, $NR^bR^c$, $C(=O)NR^bR^c$, $NR^bC(=O)R^c$, $SO_2NR^bR^c$, $CF_3$, CN, $NO_2$, F, Cl, Br, I, or $C_{2-5}$ heterocyclyl. In some embodiments, $R^{17}$ can be H, $CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{17}$ can be H.

With respect to any relevant formula or structural depiction above, some examples of $R^{18}$ can include $R^b$, $OR^b$, $SR^b$, $C(=O)R^b$, $CO_2R^b$, $OC(=O)R^b$, $NR^bR^c$, $C(O)NR^bR^c$, $NR^bC(=O)R^c$, $SO_2NR^bR^c$, $CF_3$, CN, $NO_2$, F, Cl, Br, I, or $C_{2-5}$ heterocyclyl. In some embodiments, $R^{18}$ can be H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, or $NO_2$. In some embodiments, $R^{18}$ can be H.

In some embodiments, $R^{15}$, $R^{16}$, $R^{17}$, and $R^{18}$ can be H.

With respect to any relevant formula or structural depiction above, some examples of $R^{12}$ can include $R^b$, $OR^b$, $SR^b$, $C(=O)R^b$, $CO_2R^b$, $OC(=O)R^b$, $NR^bR^c$, $C(=O)NR^bR^c$, NR$^b$C(=O)R$^c$, SO$_2$NR$^b$R$^c$, CF$_3$, CN, NO$_2$, F, Cl, Br, I, or C$_{2-5}$ heterocyclyl. In some embodiments, R$^{12}$ can be H, CH$_3$, CH$_2$CH$_3$, Cl, Br, OH, OCH$_3$, SCH$_3$, NH$_2$, NHCH$_3$, N(CH$_3$)$_2$, SO$_2$NH$_2$, CH$_2$C≡CH, or NO$_2$. In some embodiments, R12 can be H or SO$_2$NH$_2$. In some embodiments, R12 can be H. In some embodiments, R12 can be SO$_2$NH$_2$.

With respect to any relevant formula or structural depiction above, some examples of R$^{13}$ can include R$^b$, OR$^b$, SR$^b$, C(=O)R$^b$, CO$_2$R$^b$, OC(=O)R$^b$, NR$^b$R$^c$, C(=O)NR$^b$R$^c$, NR$^b$C(=O)R$^c$, SO$_2$NR$^b$R$^c$, CF$_3$, CN, NO$_2$, F, Cl, Br, I, or C$_{2-5}$ heterocyclyl. In some embodiments, R$_{13}$ can be H, CH$_3$, CH$_2$CH$_3$, Cl, Br, OH, OCH$_3$, SCH$_3$, NH$_2$, NHCH$_3$, N(CH$_3$)$_2$, SO$_2$NH$_2$, morpholino, or NO$_2$. In some embodiments, R$^{13}$ can be H.

In some embodiments, R$^{12}$ and R$^{13}$ can be H.

With respect to any relevant formula or structural depiction above, some examples of R$^{20}$ can include R$^b$, OR$^b$, SR$^b$, C(=O)R$^b$, CO$_2$R$^b$, OC(=O)R$^b$, NR$^b$R$^c$, C(=O)NR$^b$R$^c$, NR$^b$C(=O)R$^c$, SO$_2$NR$^b$R$^c$, CF$_3$, CN, NO$_2$, F, Cl, Br, I, or C$_{2-5}$ heterocyclyl. In some embodiments, R$^{20}$ can be H, CH$_3$, CH$_2$CH$_3$, Cl, Br, OH, OCH$_3$, SCH$_3$, NH$_2$, NHCH$_3$, N(CH$_3$)$_2$, SO$_2$NH$_2$, morpholino, CH$_2$C≡CH, or NO$_2$. In some embodiments, R$^{20}$ can be H, CH$_2$CH$_3$, OCH$_3$, N(CH$_3$)$_2$, morpholino, or SCH$_3$. In some embodiments, R$^{20}$ can be H. In some embodiments, R$^{20}$ can be CH$_2$CH$_3$. In some embodiments, R$^{20}$ can be OCH$_3$. In some embodiments, R$^{20}$ can be CN(CH$_3$)$_2$. In some embodiments, R$^{20}$ can be morpholino. In some embodiments, R$^{20}$ can be SCH$_3$.

With respect to any relevant formula or structural depiction above, some examples of R22 can include Rb, ORb, SRb, CF3, CN, NO2, F, Cl, Br, I, or C2-5 heterocyclyl. In some embodiments, R22 can be H, CH3, or CH2CH3. In some embodiments, R22 can be H.

In some embodiments, R$^{19}$ and R$^{22}$ can be H.

With respect to any relevant formula or structural depiction above, some examples of R$^{14}$ can include R$^b$, OR$^b$, SR$^b$, C(=O)R$^b$, CO$_2$R$^b$, OC(=O)R$^b$, NR$^b$R$^c$, C(=O)NR$^b$R$^c$, NR$^b$C(=O)R$^c$, SO$_2$NR$^b$R$^c$, CF$_3$, CN, NO$_2$, F, Cl, Br, or I. In some embodiments, R$^{30}$ can be H, CH$_3$, CH$_2$CH$_3$, Cl, Br, OH, OCH$_3$, SCH$_3$, NH$_2$, NHCH$_3$, N(CH$_3$)$_2$, SO$_2$NH$_2$, CH$_2$C≡CH, or NO$_2$. In some embodiments, R$^{14}$ can be H.

With respect to any relevant formula or structural depiction above, examples of R$^{13}$ can include R$^b$, OR$^b$, SR$^b$, C(=O)R$^b$, CO$_2$R$^b$, OC(=O)R$^b$, NR$^b$R$^c$, C(=O)NR$^b$R$^c$, NR$^b$C(=O)R$^c$, SO$_2$NR$^b$R$^c$, CF$_3$, CN, NO$_2$, F, Cl, Br, I, or C$_{2-5}$ heterocyclyl. In some embodiments, R$^{13}$ can be H, CH$_3$, CH$_2$CH$_3$, Cl, Br, OH, OCH$_3$, SCH$_3$, NH$_2$, NHCH$_3$, N(CH$_3$)$_2$, SO$_2$NH$_2$, morpholino, CH$_2$C≡CH, or NO$_2$. In some embodiments, R$^{13}$ can be H.

With respect to any relevant formula or structural depiction above, some examples of R$^{12}$ can include R$^b$, OR$^b$, SR$^b$, C(=O)R$^b$, CO$_2$R$^b$, OC(=O)R$^b$, NR$^b$R$^c$, C(=O)NR$^b$R$^c$, NR$^b$C(=O)R$^c$, SO$_2$NR$^b$R$^c$, CF$_3$, CN, NO$_2$, F, Cl, Br, I, or C$_{2-5}$ heterocyclyl. In some embodiments, R$^{12}$ can be H, CH$_3$, CH$_2$CH$_3$, Cl, Br, OH, OCH$_3$, SCH$_3$, NH$_2$, NHCH$_3$, N(CH$_3$)$_2$, SO$_2$NH$_2$, morpholino, CH$_2$C≡CH, or NO$_2$. In some embodiments, R$^{12}$ can be H or NO$_2$. In some embodiments, R$^{12}$ can be H. In some embodiments, R$^{12}$ can be NO$_2$.

In some embodiments, R$^{14}$, R$^{13}$, and R$^{12}$ can be H. In some embodiments, R$^{13}$ and R$^{12}$ can be H.

As suggested by the list of compounds in Table 1, in some instances, the substituent that is joined to an aromatic carbon atom is H.

Specific embodiments of the compounds disclosed herein have the structures shown in Table 1.

TABLE 1

| Structure | Compound ID |
|---|---|
| (chemical structure) | 1 |
| (chemical structure) | 2 |
| (chemical structure) | 3 |

TABLE 1-continued

| Structure | Compound ID |
|---|---|
| 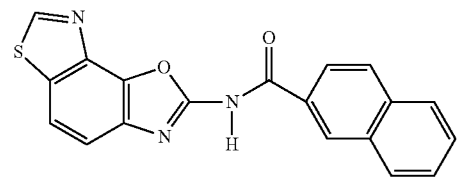 [SMILES: O=C(Nc1nc2ccc3scnc3c2o1)c1ccc2ccccc2c1] | 4 |
| 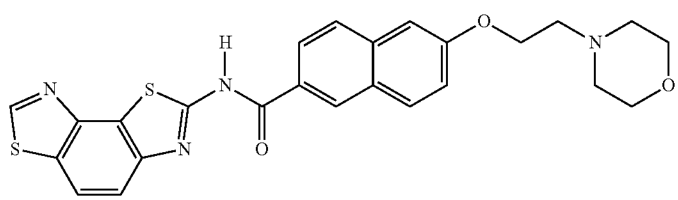 | 5 |
| 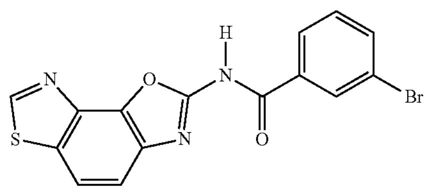 [SMILES: O=C(Nc1nc2ccc3scnc3c2o1)c1cccc(Br)c1] | 6 |
| 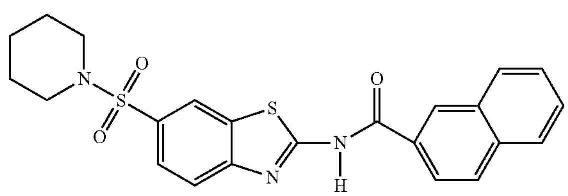 [SMILES: O=C(Nc1nc2ccc(S(=O)(=O)N3CCCCC3)cc2s1)c1ccc2ccccc2c1] | 7 |
| 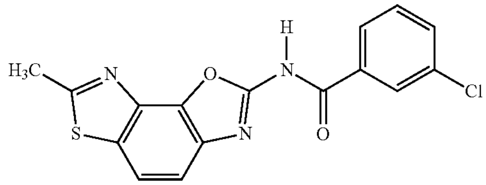 [SMILES: Cc1nc2c(ccc3nc(NC(=O)c4cccc(Cl)c4)oc32)s1] | 8 |
| 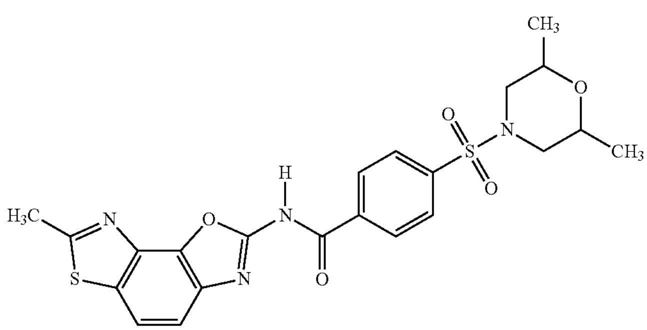 | 9 |
| 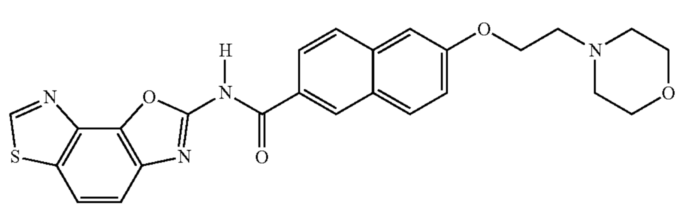 [SMILES: O=C(Nc1nc2ccc3scnc3c2o1)c1ccc2cc(OCCN3CCOCC3)ccc2c1] | 10 |

TABLE 1-continued
| Structure | Compound ID |
|---|---|
| 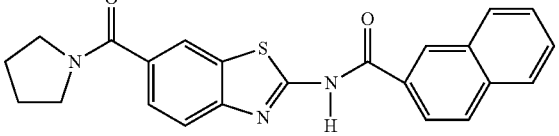 | 11 |
| 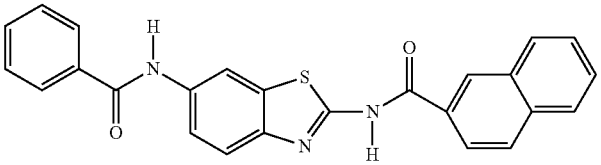 [SMILES: O=C(Nc1ccc2nc(NC(=O)c3ccc4ccccc4c3)sc2c1)c1ccccc1] | 12 |
| 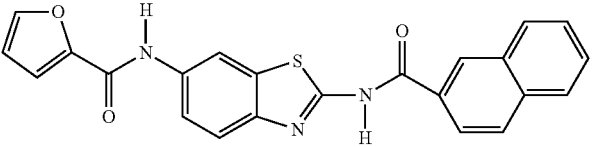 [SMILES: O=C(Nc1nc2ccc(NC(=O)c3ccco3)cc2s1)c1ccc2ccccc2c1] | 13 |
| 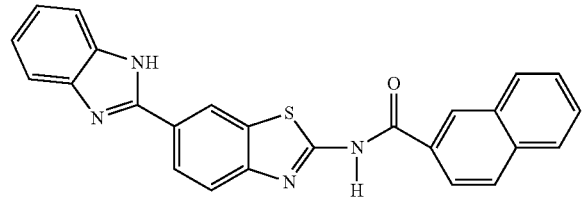 [SMILES: O=C(Nc1nc2ccc(-c3nc4ccccc4[nH]3)cc2s1)c1ccc2ccccc2c1] | 14 |
| 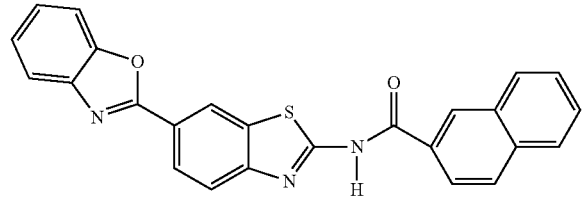 [SMILES: O=C(Nc1nc2ccc(-c3nc4ccccc4o3)cc2s1)c1ccc2ccccc2c1] | 15 |
| 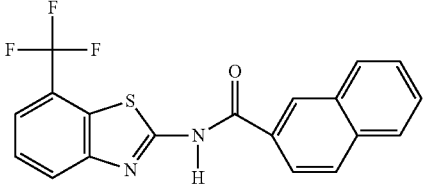 [SMILES: O=C(Nc1nc2cccc(C(F)(F)F)c2s1)c1ccc2ccccc2c1] | 16 |
| 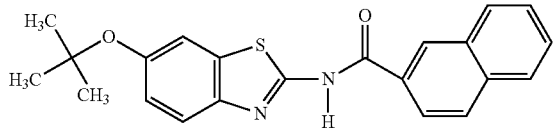 [SMILES: CC(C)(C)Oc1ccc2nc(NC(=O)c3ccc4ccccc4c3)sc2c1] | 17 |
| 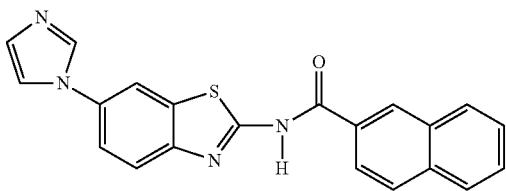 [SMILES: O=C(Nc1nc2ccc(-n3ccnc3)cc2s1)c1ccc2ccccc2c1] | 18 |

TABLE 1-continued

| Structure | Compound ID |
|---|---|
| 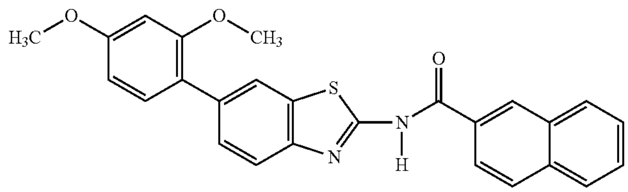 [SMILES: COc1ccc(-c2ccc3nc(NC(=O)c4ccc5ccccc5c4)sc3c2)c(OC)c1] | 19 |
| 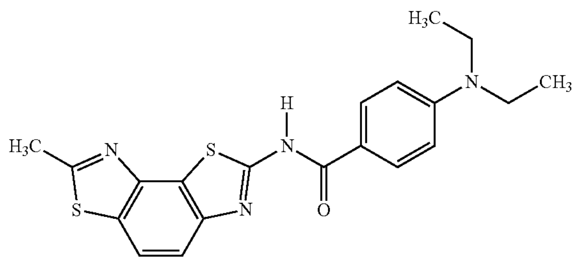 [SMILES: CCN(CC)c1ccc(C(=O)Nc2nc3ccc4sc(C)nc4c3s2)cc1] | 20 |
| 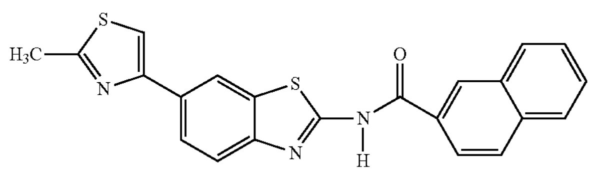 [SMILES: Cc1nc(-c2ccc3nc(NC(=O)c4ccc5ccccc5c4)sc3c2)cs1] | 21 |

Unless stereochemistry is unambiguously depicted, any structure, formula, or name for a compound can refer to any stereoisomer or any mixture of stereoisomers of the compound.

Unless otherwise indicated, any reference to a compound herein by structure, formula, name or any other means, includes pharmaceutically acceptable salts, such as sodium, potassium, and ammonium salts; prodrugs, such as ester prodrugs; alternate solid forms, such as polymorphs, solvates, hydrates, etc.; tautomers; isomers; or, any other chemical species that may rapidly convert to a compound described herein under conditions in which the compounds are used as described herein.

As used herein, the term "pharmaceutically acceptable salt" refers to pharmaceutical salts that are, within the scope of sound medical judgment, suitable for use in contact with the tissues of subjects without undue toxicity, irritation, and allergic response, and are commensurate with a reasonable benefit/risk ratio. Pharmaceutically acceptable salts are well known in the art. In one embodiment, the pharmaceutically acceptable salt is a sulfate salt. For example, S. M. Berge, et al. describes pharmaceutically acceptable salts in J. Pharm. Sci., 1977, 66:1-19.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Pharmaceutically acceptable acidic/anionic salts also include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Suitable pharmaceutically acceptable base addition salts include metallic salts made from aluminum, calcium, lithium, magnesium, potassium, sodium, and zinc or organic salts made from N,N'-dibenzylethylene-diamine, chloroprocaine, choline, diethanolamine, ethylenediamine, N-methylglucamine, lysine, arginine, and procaine. All of these salts can be prepared by conventional means from the corresponding compound represented by the disclosed compounds by treating, for example, the disclosed compounds with the appropriate acid or base. Pharmaceutically acceptable basic/cationic salts also include, the diethanolamine, ammonium, ethanolamine, piperazine, and triethanolamine salts.

A pharmaceutically acceptable salt includes any salt that retains the activity of the parent compound and is acceptable for pharmaceutical use. A pharmaceutically acceptable salt also refers to any salt which may form in vivo as a result of administration of an acid, another salt, or a prodrug which is converted into an acid or salt.

A prodrug includes a compound which is converted to a therapeutically active compound after administration, such as by hydrolysis of an ester group or some other biologically labile group.

"Functional group" refers to an atom or a group of atoms that have similar chemical properties whenever they occur in different compounds, and as such the functional group defines the characteristic physical and chemical properties of families of organic compounds.

Unless otherwise indicated, when any compound or chemical structural feature (collectively referred to herein as a "compound"), such as for example alkyl, aryl, etc., is referred to as being "optionally substituted," that compound can have no substituents (in which case it is "unsubstituted"), or it can include one or more substituents (in which case it is "substituted"). The term "substituent" has the ordinary meaning known to one of ordinary skill in the art. In some embodiments, the substituent can be an ordinary organic moiety known in the art, which can have a molecular weight (e.g., the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, the substituent includes: 0-30, 0-20, 0-10, or 0-5 carbon (C) atoms; and/or 0-30, 0-20, 0-10, or 0-5 heteroatoms including N, O, S, Si, F, Cl, Br, or I; provided that the substituent includes at least one atom including C, N, O, S, Si, F, Cl, Br, or I in a substituted compound. Examples of substituents can include alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc. For convenience, the term "molecular weight" is used with respect to a moiety or part of a molecule to indicate the sum of the atomic masses of the atoms in the moiety or part of a molecule, even though it may not be a complete molecule.

"Hydrocarbyl" has the broadest meaning generally understood in the art, and can include a moiety composed of carbon and hydrogen. Some examples can include alkyl, alkenyl, alkynyl, aryl, etc., and combinations thereof, and can be linear, branched, cyclic, or a combination thereof. Hydrocarbyl can be bonded to any other number of moieties (for example, can be bonded to one other group, such as —$CH_3$, —CH=$CH_2$, etc.; two other groups, such as -phenyl-, —C≡C—, etc.; or any number of other groups) that the structure can bear, and in some embodiments, can contain from one to thirty-five carbon atoms. Examples of hydrocarbyl groups include C1 alkyl, C2 alkyl, C2 alkenyl, C2 alkynyl, C3 alkyl, C3 alkenyl, C3 alkynyl, C4 alkyl, C4 alkenyl, C4 alkynyl, C5 alkyl, C5 alkenyl, C5 alkynyl, C6 alkyl, C6 alkenyl, C6 alkynyl, phenyl, etc.

"Alkyl" has the broadest meaning generally understood in the art, and can include a moiety composed of carbon and hydrogen containing no double or triple bonds and not having any cyclic structure. Alkyl can be linear alkyl, branched alkyl, cycloalkyl, or a combination thereof, and in some embodiments, can contain from one to thirty-five carbon atoms. In some embodiments, alkyl can include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g., branched butyl isomers), $C_5H_{11}$ (e.g., branched pentyl isomers), $C_6H_{13}$ (e.g., branched hexyl isomers), $C_7H_{15}$ (e.g., branched heptyl isomers), etc.; $C_{3-10}$ cycloalkyl, such as $C_3H_5$ (e.g. cyclopropyl), $C_4H_7$ (e.g., cyclobutyl isomers such as cyclobutyl, methylcyclopropyl, etc.), $C_5H_9$ (e.g., cyclopentyl isomers such as cyclopentyl, methylcyclobutyl, dimethylcyclopropyl, etc.) $C_6H_{11}$ cyclohexyl isomers), $C_7H_{13}$ (e.g., cycloheptyl isomers), etc.; $C_{3-12}$ bicycloalkyl such as decahydronaphthyl, and norbornyl; and the like.

"Alkyl," "alkenyl" and "alkynyl" refer to substituted and unsubstituted alkyls, alkenyls and alkynyls, respectively. An alkyl group can be optionally substituted as defined herein.

Substituted alkyls, alkenyls, and alkynyls refer to alkyls, alkenyls, and alkynyls substituted with one to five substituents including H, alkyl, aryl, alkenyl, alkynyl, arylalkyl, alkoxy, aryloxy, arylalkoxy, alkoxyalkylaryl, alkylamino, arylamino, $NH_2$, OH, CN, $NO_2$, $OCF_3$, $CF_3$, F, 1-amidine, 2-amidine, alkylcarbonyl, morpholinyl, piperidinyl, dioxanyl, pyranyl, heteroaryl, furanyl, thiophenyl, tetrazolo, thiazolyl, isothiazolyl, imidazolyl, thiadiazolyl, thiadiazole S-oxide, thiadiazole S,S-dioxide, pyrazolo, oxazolyl, isoxazolyl, pyridinyl, pyrimidinyl, quinolinyl, isoquinolinyl, SR, SOR, SO2R, CO2R, COR, CONR'R", CSNR'R", and SOnNR'R". As used herein, R, R', and R" can include R groups described in this disclosure, such as $R^a$, $R^b$, $R^c$, $R^d$, $R^e$, $R^2$, or $R^3$.

Either alone or in combination, "alkynyl" refers to a functional group including a straight-chain or branched-chain hydrocarbon containing from 2 to 20 carbon atoms and having one or more carbon-carbon triple bonds and not having any cyclic structure. An alkynyl group may be optionally substituted as defined herein. Examples of alkynyl groups include ethynyl, propynyl, hydroxypropynyl, butynyl, butyn-1-yl, butyn-2-yl, 3-methylbutyn-1-yl, pentynyl, pentyn-1-yl, hexynyl, hexyn-2-yl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, and the like.

"Alkylene", alone or in combination, refers to a saturated aliphatic group derived from a straight or branched chain saturated hydrocarbon attached at two or more positions, such as methylene (—$CH_2$—). Unless otherwise specified, "alkyl" can include "alkylene" groups.

Either alone or in combination "alkylcarbonyl" or "alkanoyl" refer to a functional group including an alkyl group attached to the parent molecular moiety through a carbonyl group. Examples of alkylcarbonyl groups can include methylcarbonyl, ethylcarbonyl, and the like.

Either alone or in combination, "heteroalkyl" refers to a functional group including a straight-chain, branched-chain, or cyclic hydrocarbon containing from 1 to 20 atoms linked exclusively by single bonds, where at least one atom in the chain is a carbon and at least one atom in the chain is O, S, N, or any combination thereof. The heteroalkyl group can be fully saturated or contain from 1 to 3 degrees of unsaturation. The non-carbon atoms can be at any interior position of the heteroalkyl group, and up to two non-carbon atoms can be consecutive, such as, e.g., —$CH_2$—NH—$OCH_3$. In addition, the non-carbon atoms can optionally be oxidized and the nitrogen can optionally be quaternized. Examples of heteroalkyl groups can include morpholine, azanorbornane, tetrahydrofuran, and the like.

Either alone or in combination, "alkyloxy" or "alkoxy" refer to a functional group including an alkyl ether group. Examples of alkoxys can include methoxy, ethoxy, n-propoxy, isopropoxy, n-butoxy, iso-butoxy, sec-butoxy, tert-butoxy, and the like.

Either alone or in combination, "hydroxy" refers to the functional group hydroxyl (—OH).

Either alone or in combination, "carboxyl" or "carboxy" refers to the functional group —C(=O)OH or the corresponding "carboxylate" anion —C(=O)O—. Examples include formic acid, acetic acid, oxalic acid, and benzoic acid. An "O-carboxyl" group refers to a carboxyl group having the general formula RCOO, wherein R is an organic moiety or group. A "C-carboxyl" group refers to a carboxyl group having the general formula COOR, wherein R is an organic moiety or group.

Either alone or in combination, "oxo" refers to the functional group =O.

"Carbocyclic" has the broadest meaning generally understood in the art, and includes a ring or ring system wherein the ring atoms are all carbon. Examples can include phenyl, naphthyl, anthracenyl, cycloalkyl, cycloalkenyl, cycloalkynyl, etc., and combinations thereof.

"Heterocyclic" has the broadest meaning generally understood in the art, and includes a ring or ring system wherein at least one of the ring atoms is not carbon, such as N, O, S, etc. Examples can include heteroaryl, cycloheteroalkyl, cycloheteroalkenyl, cycloheteroalkynyl, cyclic heteroalkyl, etc., and combinations thereof. Examples of heterocyclic systems can include quinoline, tetrahydroisoquinoline, tetrahydropyran, imidazole, thiophene, dihydrobenzofuran, and the like.

Either alone or in combination, "cycloalkyl," "carbocyclicalkyl" and "carbocyclealkyl" refer to a functional group including a substituted or unsubstituted non-aromatic hydrocarbon with a non-conjugated cyclic molecular ring structure of 3 to 12 carbon atoms linked exclusively with carbon-carbon single bonds in the carbon ring structure. A cycloalkyl group can be monocyclic, bicyclic or polycyclic, and can optionally include one to three additional ring structures, such as, e.g., an aryl, a heteroaryl, a cycloalkenyl, a heterocycloalkyl, or a heterocycloalkenyl.

Either alone or in combination, "lower cycloalkyl" refers to a functional group including a monocyclic substituted or unsubstituted non-aromatic hydrocarbon with a non-conjugated cyclic molecular ring structure of 3 to 6 carbon atoms linked exclusively with carbon-carbon single bonds in the carbon ring structure. Examples of lower cycloalkyl groups can include cyclopropyl, cyclobutyl, cyclopentyl, and cyclohexyl.

"Aryl" has the broadest meaning generally understood in the art, and can include an aromatic ring or aromatic ring system. An aryl group can be monocyclic, bicyclic or polycyclic, and may optionally include one to three additional ring structures; such as, for example, a cycloalkyl, a cycloalkenyl, a heterocycloalkyl, a heterocycloalkenyl, or a heteroaryl. The term "aryl" includes phenyl (benzenyl), thiophenyl, indolyl, naphthyl, tolyl, xylyl, anthracenyl, phenanthryl, azulenyl, biphenyl, naphthalenyl, 1-methylnaphthalenyl, acenaphthenyl, acenaphthylenyl, anthracenyl, fluorenyl, phenalenyl, phenanthrenyl, benzo[a]anthracenyl, benzo[c]phenanthrenyl, chrysenyl, fluoranthenyl, pyrenyl, tetracenyl (naphthacenyl), triphenylenyl, anthanthrenyl, benzopyrenyl, benzo[a]pyrenyl, benzo[e]fluoranthenyl, benzo[ghi]perylenyl, benzo[j]fluoranthenyl, benzo[k]fluoranthenyl, corannulenyl, coronenyl, dicoronylenyl, helicenyl, heptacenyl, hexacenyl, ovalenyl, pentacenyl, picenyl, perylenyl, tetraphenylenyl, etc.

Additionally, either alone or in combination, "aryl," "hydrocarbyl aryl" or "aryl hydrocarbon" can refer to a functional group including a substituted or unsubstituted aromatic hydrocarbon with a conjugated cyclic molecular ring structure of 3 to 12 carbon atoms. Substituted aryl refers to aryls substituted with one to five substituents including H, lower alkyl, aryl, alkenyl, alkynyl, arylalkyl, alkoxy, aryloxy, arylalkoxy, alkoxyalkylaryl, alkylamino, arylamino, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, SR, SOR, $SO_2R$, $CO_2R$, COR, CONR'R", CSNR'R", SOnNR'R", etc.

Either alone or in combination, "lower aryl" refers to a functional group including a substituted or unsubstituted aromatic hydrocarbon with a conjugated cyclic molecular ring structure of 3 to 10 carbon atoms. Examples of lower aryl groups can include phenyl and naphthyl.

Either alone or in combination, "heteroaryl" refers to a functional group including a substituted or unsubstituted aromatic hydrocarbon with a conjugated cyclic molecular ring structure of 3 to 12 atoms, where at least one atom in the ring structure is a carbon and at least one atom in the ring structure is O, S, N, or any combination thereof. A heteroaryl group can be monocyclic, bicyclic or polycyclic, and may optionally include one to three additional ring structures, such as, e.g., an aryl, a cycloalkyl, a cycloalkenyl, a heterocycloalkyl, or a heterocycloalkenyl. Examples of heteroaryl groups can include acridinyl, benzidolyl, benzimidazolyl, benzisoxazolyl, benzodioxinyl, dihydrobenzodioxinyl, benzodioxolyl, 1,3-benzodioxolyl, benzofuryl, benzoisoxazolyl, benzopyranyl, benzothiophenyl, benzo[c]thiophenyl, benzotriazolyl, benzoxadiazolyl, benzoxazolyl, benzothiadiazolyl, benzothiazolyl, benzothienyl, carbazolyl, chromonyl, cinnolinyl, dihydrocinnolinyl, coumarinyl, dibenzofuranyl, furopyridinyl, furyl, indolizinyl, indolyl, dihydroindolyl, imidazolyl, indazolyl, isobenzofuryl, isoindolyl, isoindolinyl, dihydroisoindolyl, isoquinolyl, dihydroisoquinolinyl, isoxazolyl, isothiazolyl, oxazolyl, oxadiazolyl, phenanthrolinyl, phenanthridinyl, purinyl, pyranyl, pyrazinyl, pyrazolyl, pyridyl, pyrimidinyl, pyridazinyl, pyrrolinyl, pyrrolyl, pyrrolopyridinyl, quinolyl, quinoxalinyl, quinazolinyl, tetrahydroquinolinyl, tetrazolopyridazinyl, tetrahydroisoquinolinyl, thiophenyl, thiazolyl, thiadiazolyl, thienopyridinyl, thienyl, thiophenyl, triazolyl, xanthenyl, and the like.

The phenyl structure associated with some of the embodiments described herein is depicted below. This structure can be unsubstituted, as shown below, or can be substituted such that a substituent can independently be in any position normally occupied by a hydrogen atom when the structure is unsubstituted. Unless a point of attachment is indicated by -|, attachment may occur at any position normally occupied by a hydrogen atom.

Phenyl

Each $R^a$ can independently be H; optionally substituted hydrocarbyl; optionally substituted aryl, such as optionally substituted phenyl or optionally substituted aryl; optionally substituted heteroaryl, such as optionally substituted pyridinyl, optionally substituted furyl, optionally substituted thienyl, etc. In some embodiments, each $R^a$ can independently be H, or $C_{1-12}$ alkyl, including: linear or branched alkyl such as linear or branched alkyl of the formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of the formula: $C_3H_5$, $C_4H_7$, $C_5H_9$, $C_6H_{11}$, $C_7H_{13}$, $C_8H_{15}$, $C_9H_{17}$, $C_{10}H_{19}$, etc.

Pharmaceutical Compositions

According to other embodiments, the present disclosure provides for a pharmaceutical composition including any one of the compounds described herein.

Pharmaceutical compositions can be formed by combining a compound disclosed herein, or a pharmaceutically acceptable prodrug or salt thereof, with a pharmaceutically acceptable carrier suitable for delivery to a subject in accordance with known methods of drug delivery. Accordingly, a "pharmaceutical composition" includes at least one compound disclosed herein together with one or more pharmaceutically acceptable carriers, excipients, or diluents, as appropriate for the chosen mode of administration.

A pharmaceutical composition including a compound of the disclosure can be formulated in a variety of forms depending upon the particular indication being treated and will be apparent to one of ordinary skill in the art. Formulating pharmaceutical compositions including one or more compounds of the disclosure can employ straightforward medicinal chemistry processes. The pharmaceutical compositions can be subjected to conventional pharmaceutical operations such as sterilization and/or can contain conventional adjuvants, such as buffering agents, preservatives, isotonicifiers, stabilizers, wetting agents, emulsifiers, etc.

The administration of the formulations of the present disclosure can be performed in a variety of ways, including orally, subcutaneously, intravenously, intracerebrally, intranasally, transdermally, intraperitoneally, intramuscularly, intrapulmonary, intrathecally, vaginally, rectally, intraocularly, or in any other acceptable manner. The formulations can be administered continuously by infusion, although bolus injection is acceptable, using techniques known in the art, such as pumps (e.g., subcutaneous osmotic pumps) or implantation. In some instances the formulations can be directly applied as a solution or spray.

An example of a pharmaceutical composition is a solution designed for parenteral administration. Although in many cases pharmaceutical solution formulations are provided in liquid form, appropriate for immediate use, such parenteral formulations can also be provided in frozen or in lyophilized form. In the former case, the composition must be thawed prior to use. The latter form is often used to enhance the stability of the active compound contained in the composition under a wider variety of storage conditions, as it is recognized by those of ordinary skill in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

Parenterals can be prepared for storage as lyophilized formulations or aqueous solutions by mixing, as appropriate, the compound having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from 2 mM to 50 mM of a pharmaceutical composition. Suitable buffering agents for use with the present disclosure include both organic and inorganic acids and salts thereof, such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.), and acetate buffers (e.g., acetic acid-sodium acetate mixture, acetic acid-sodium hydroxide mixture, etc.). Additional possibilities are phosphate buffers, histidine buffers, and trimethylamine salts such as Tris.

Preservatives can be added to retard microbial growth, and are typically added in amounts of 0.2%-1% (w/v), Suitable preservatives for use with the present disclosure include phenol, benzyl alcohol, meta-cresol, methyl paraben, propyl paraben, octadecyldimethylbenzyl ammonium chloride, benzalkonium halides (e.g., benzalkonium chloride, bromide or iodide), hexamethonium chloride, alkyl parabens such as methyl or propyl paraben, catechol, resorcinol, cyclohexanol and 3-pentanol.

Isotonicifiers can be added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc.; organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, alpha-monothioglycerol and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active compound weight.

Additional miscellaneous excipients include fillers (e.g., starch), chelating agents (e.g., EDTA), antioxidants (e.g., ascorbic acid, methionine, vitamin E), and cosolvents.

Particular embodiments can include one or more of ethanol (<10%), propylene glycol (<40%), polyethylene glycol (PEG) 300 or 400 (<60%), N—N-dimethylacetamide (DMA, <30%), N-methyl-2-pyrrolidone (NMP, <20%), dimethyl sulfoxide (DMSO, <20%) co-solvents or the cyclodextrins (<40%) and have a pH of 3 to 9.

The compound(s) can also be entrapped in microcapsules prepared, for example, by coascervation techniques or by interfacial polymerization, for example hydroxymethylcellulose, gelatin or poly-(methylmethacrylate) microcapsules, in colloidal drug delivery systems (for example liposomes, albumin microspheres, microemulsions, nano-particles and nanocapsules) or in macroemulsions. Such techniques are disclosed in Remington, The Science and Practice of Pharmacy, 21st Ed., published by Lippincott Williams & Wilkins, A Wolters Kluwer Company, 2005.

Parenteral formulations to be used for in vivo administration generally are sterile. This is readily accomplished, for example, by filtration through sterile filtration membranes.

Generally, the pharmaceutical compositions can be made up in a solid form (including granules, powders, or suppositories) or in a liquid form (e.g., solutions, suspensions, or emulsions). The compounds can be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, they can be dissolved in saline, water, polyethylene glycol, propylene glycol, ethanol, oils (such as corn oil, peanut oil, cottonseed oil, or sesame oil), tragacanth gum, and/or various buffers. Other adjuvants and modes of administration are well known in the pharmaceutical art. The carrier or diluent can include time delay material, such as glyceryl monostearate or glyceryl distearate alone or with a wax, or other materials well known in the art.

Oral administration of the compounds and compositions is one intended practice of the disclosure. For oral administration, the pharmaceutical composition can be in solid or liquid form, e.g., in the form of a capsule, tablet, powder, granule, suspension, emulsion or solution. The pharmaceutical composition is preferably made in the form of a dosage unit containing a given amount of the active ingredient. A suitable daily dose for a human or other subject can vary widely depending on the condition of the subject and other factors, but can be determined by persons of ordinary skill in the art using routine methods.

Solid dosage forms for oral administration can include capsules, tablets, pills, powders, and granules. In such solid dosage forms, the active compound can be admixed with at least one inert diluent such as sucrose, lactose, or starch. Such dosage forms can also include, as is normal practice, additional substances other than inert diluents, e.g., lubricating agents such as magnesium stearate. In the case of capsules, tablets, and pills, the dosage forms can also include buffering agents. Tablets and pills can additionally be prepared with enteric coatings. For buccal administration the pharmaceutical compositions can take the form of tablets or lozenges formulated in conventional manners.

Liquid dosage forms for oral administration can include pharmaceutically acceptable emulsions, solutions, suspensions, syrups, and elixirs containing inert diluents commonly used in the art, such as water. Such pharmaceutical compositions can also include adjuvants, such as wetting, sweetening, flavoring, and perfuming agents.

The pharmaceutical compositions can be formulated for parenteral administration by injection, e.g. by bolus injection, or infusion. Formulations for injection can be presented in unit dosage form, e.g. in glass ampoule or multi-dose containers, e.g. glass vials. The pharmaceutical compositions for injection can take such forms as suspensions, solutions, or emulsions in oily or aqueous vehicles, and can contain formulatory agents such as antioxidants, buffers, non-ionic detergents, dispersants, isotonicifiers, suspending agents, stabilizers, preservatives, dispersing agents and/or other miscellaneous additives.

Although in many cases pharmaceutical compositions provided in liquid form are appropriate for immediate use, such parenteral formulations can also be provided in frozen or in lyophilized form. In the former case, the pharmaceutical composition must be thawed prior to use. The latter form is often used to enhance the stability of the compound contained in the pharmaceutical composition under a wider variety of storage conditions, as it is recognized by those or ordinary skill in the art that lyophilized preparations are generally more stable than their liquid counterparts. Parenterals can be prepared for storage as lyophilized formulations by mixing, as appropriate, the compound having the desired degree of purity with one or more pharmaceutically acceptable carriers, excipients, or stabilizers typically employed in the art (all of which are termed "excipients"), for example, antioxidants, buffers, non-ionic detergents, dispersants, isotonicifiers, suspending agents, stabilizers, preservatives, dispersing agents and/or other miscellaneous additives. Such lyophilized preparations are reconstituted prior to use by the addition of one or more suitable pharmaceutically acceptable diluents such as sterile pyrogen-free water for injection or sterile physiological saline solution.

For administration by inhalation (e.g., nasal or pulmonary), the pharmaceutical compositions can be conveniently delivered in the form of an aerosol spray, from pressurized packs or a nebulizer, and/or with the use of suitable propellant, e.g. dichlorodifluoromethane, trichlorofluoromethane, dichlorotetrafluoroethane, carbon dioxide, or other suitable gases or mixture of gases.

The compounds or compositions can be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, they can be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are known in the pharmaceutical art. The carrier or diluent can include time delay material, such as glyceryl monostearate or glyceryl distearate alone or with a wax, or other materials known in the art.

In addition to the formulations described above, the pharmaceutical compositions can also be formulated as depot preparations. Such long acting formulations can be administered by implantation or by intramuscular injection.

The compounds can also be entrapped in microcapsules prepared, for example, by coascervation techniques or by interfacial polymerization, (for example hydroxymethylcellulose, gelatin or poly-(methylmethacylate) microcapsules), in colloidal drug delivery systems (for example liposomes, albumin microspheres, microemulsions, nano-particles and nanocapsules) or in macroemulsions. Such techniques are disclosed in Remington, The Science and Practice of Pharmacy, 21st Ed., published by Lippincott Williams & Wilkins, A Wolters Kluwer Company, 2005.

Suitable examples of sustained-release preparations include semi-permeable matrices of solid hydrophobic polymers containing the compound or composition, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the PROLEASE® technology (Alkermes, Cambridge, Mass.) or LUPRON DEPOT® (injectable microspheres composed of lactic acid-glycolic acid copolymer and leuprolide acetate; Abbott Laboratories, Abbott Park, Ill.), and poly-D-(-)-3-hydroxybutyric acid. While polymers such as ethylene-vinyl acetate and lactic acid-glycolic acid enable release of molecules for long periods such as up to or over 100 days, certain hydrogels release compounds for shorter time periods.

Methods of Use

The pharmaceutical compositions disclosed herein can be used to treat a viral infection in a subject; wherein the viral infection is caused by a virus from one the following families: Arenaviridae, Arterivirus, Astroviridae, Birnaviridae, Bromoviridae, Bunyaviridae, Caliciviridae, Closteroviridae, Comoviridae, Coronaviridae, Cystoviridae, Filoviridae, Flaviviridae, Flexiviridae, Hepadnaviridae, Hepevirus, Herpesviridae, Leviviridae, Luteoviridae, Mesoniviridae, Mononegavirales, Mosaic Viruses, Nidovirales, Nodaviridae, Orthomyxoviridae, Papillomaviridae, Paramyxoviridae, Picobirnaviridae, Picobirnavirus, Picornaviridae, Potyviridae, Reoviridae, Retroviridae, Roniviridae, Sequiviridae, Tenuivirus, Togaviridae, Tombusviridae, Totiviridae, and Tymoviridae.

According to more specific embodiments, the pharmaceutical compositions can be used to treat a viral infection caused by one or more of Alfuy virus, Banzi virus, bovine diarrhea virus, Chikungunya virus, Dengue virus (DNV), Encephalomyocarditis virus (EMCV), Hepatitis B virus (HBV), HCV, human cytomegalovirus (hCMV), HIV, Ilheus virus, influenza virus (including avian and swine isolates), rhinovirus, norovirus, adenovirus, Japanese encephalitis virus, Kokobera virus, Kunjin virus, Kyasanur forest disease virus, louping-ill virus, measles virus, MERS-coronavirus (MERS), metapneumovirus, any of the Mosaic Viruses, Murray Valley virus, parainfluenza virus, poliovirus, Powassan virus, respiratory syncytial virus (RSV), Rocio virus, SARS-coronavirus (SARS), St. Louis encephalitis virus, tick-borne encephalitis virus, WNV, Ebola virus, Nipah virus, Lassa virus, Tacaribe virus, Junin virus, and yellow fever virus.

In an embodiment, a method of treating a viral infection in a subject can include administering to the subject a therapeutically effective amount of a pharmaceutical composition having the structure In some cases, the viral infection is caused by Ebola virus.

Many RNA viruses share biochemical, regulatory, and signaling pathways. These viruses include influenza virus (including avian and swine isolates), rhinovirus, norovirus, DNV, RSV, WNV, HCV, parainfluenza virus, metapneumovirus, Chikungunya virus, SARS, MERS, poliovirus, measles virus, yellow fever virus, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, any of the Mosaic Viruses, HIV, Ebola virus, Lassa virus, and the Kyasanur forest disease virus. The compounds, pharmaceutical compositions, and methods disclosed herein can be used to treat these viruses.

Antiviral activity against WNV, Nipah Virus, Lassa Fever Virus, and Ebola Virus in vitro is measured by focus-forming assay. Virus strains that are used in these assays include WNV-TX (WNV), WNV-MAD (WNV), NiV-Malaysia (Nipah), LASV-Josiah (Lassa Fever), and ZEBOV-Mayinga (Ebola). Cultured human cells including human umbilical vein cells (HUVEC) are seeded in tissue-culture plates and infected with virus at MOI of 0.01 to 0.5 for a duration including but not limited to 2 hours and then removed. Compound dilutions are prepared in 0.5% DMSO and used to treat cells at final concentrations of compound ranging 0.001 to 10 μM per well. Vehicle control wells contain 0.5% DMSO and are used to compare to drug treated cells. Virus infections after drug treatment are allowed to proceed for 48 to 96 hours. Virus supernatants are then harvested and used to infect new monolayer of permissive cells. The newly infected cells are incubated overnight (18-24 hours) and used to measure the level of infectious virus in the original supernatants by focus-forming assay using methods generally known in the art.

Methods disclosed herein include treating subjects (humans, mammals, free-range herds, veterinary animals (dogs, cats, reptiles, birds, etc.), farm animals and livestock (horses, cattle, goats, pigs, chickens, etc.), and research animals (monkeys, rats, mice, fish, etc.)) with pharmaceutical compositions disclosed herein. Treating subjects includes delivering therapeutically effective amounts. Therapeutically effective amounts include those that provide effective amounts, prophylactic treatments, and/or therapeutic treatments.

An "effective amount" is the amount of a compound necessary to result in a desired physiological change in the subject. Effective amounts are often administered for research purposes. Effective amounts disclosed herein reduce, control, or eliminate the presence or activity of viral infections and/or reduce, control, or eliminate unwanted side effects of viral infections. For example, an effective amount may result in a reduction in viral protein in a subject or assay, a reduction in viral RNA in a subject or assay, and/or a reduction in virus present in a cell culture.

A "prophylactic treatment" includes a treatment administered to a subject who does not display signs or symptoms of a viral infection or displays only early signs or symptoms of the viral infection such that treatment is administered for the purpose of diminishing, preventing, or decreasing the risk of developing the viral infection further. Thus, a prophylactic treatment functions as a preventative treatment against a viral infection. Prophylactic treatment may also include vaccines as described elsewhere herein. Prophylactic treatment may result in a lack of increase in viral proteins or RNA in a subject, and/or a lack of increase in clinical indicators of viral infection, such as: loss of appetite, fatigue, fever, muscle aches, nausea, and/or abdominal pain in the case of HCV; fever and/or headache in the case of WNV; and cough, congestion, fever, sore throat, and/or headache in the case of RSV. Prophylactic treatments can be administered to any subject regardless of whether signs of viral infection are present. In some embodiments, prophylactic treatments can be administered before travel.

A "therapeutic treatment" includes a treatment administered to a subject who displays symptoms or signs of a viral infection and is administered to the subject for the purpose of diminishing or eliminating the signs or symptoms of the viral infection. The therapeutic treatment can reduce, control, or eliminate the presence or activity of viruses and/or reduce, control, or eliminate side effects of viruses. Therapeutic treatment may result in a decrease in viral proteins or RNA in a subject, and/or a decrease in clinical indicators of viral infection, such as: loss of appetite, fatigue, fever, muscle aches, nausea, and/or abdominal pain in the case of HCV; fever and/or headache in the case of WNV; and cough, congestion, fever, cyanosis, sore throat, and/or headache in the case of RSV.

For administration, therapeutically effective amounts (also referred to herein as doses) can be initially estimated based on results from in vitro assays and/or animal model studies. For example, a dose can be formulated in animal models to achieve a circulating concentration range that includes an IC50 as determined in cell culture against a particular target. Such information can be used to more accurately determine useful doses in subjects of interest.

The actual dose amount administered to a particular subject can be determined by a physician, veterinarian, or researcher taking into account parameters such as physical and physiological factors including target, body weight, severity of condition, type of viral infection, previous or concurrent therapeutic interventions, idiopathy of the subject, and route of administration.

Pharmaceutical compositions can be administered intravenously to a subject for treatment of viral infections in a clinically safe and effective manner, including one or more separate administrations of the composition. For example, 0.05 mg/kg to 5.0 mg/kg can be administered to a subject per day in one or more doses (e.g., doses of 0.05 mg/kg once-daily (QD), 0.10 mg/kg QD, 0.50 mg/kg QD, 1.0 mg/kg QD, 1.5 mg/kg QD, 2.0 mg/kg QD, 2.5 mg/kg QD, 3.0 mg/kg QD, 0.75 mg/kg twice-daily (BID), 1.5 mg/kg BID or 2.0 mg/kg BID). For certain antiviral indications, the total daily dose of a compound can be 0.05 mg/kg to 3.0 mg/kg administered intravenously to a subject one to three times a day, including administration of total daily doses of 0.05-3.0, 0.1-3.0, 0.5-3.0, 1.0-3.0, 1.5-3.0, 2.0-3.0, 2.5-3.0, and 0.5-3.0 mg/kg/day of compounds of Table 1 using 60-minute QD, BID, or three times daily (TID) intravenous infusion dosing. In one particular example, antiviral pharmaceutical compositions can be intravenously administered QD or BID to a subject with, e.g., total daily doses of 1.5 mg/kg, 3.0 mg/kg, 4.0 mg/kg of a composition with up to 92-98% wt/wt of a compound of Table 1.

Additional useful doses can often range from 0.1 to 5 μg/kg or from 0.5 to 1 μg/kg. In other examples, a dose can include 1 μg/kg, 5 μg/kg, 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, 80 μg/kg, 85 μg/kg, 90 μg/kg, 95 μg/kg, 100 μg/kg, 150 μg/kg, 200 μg/kg, 250 μg/kg, 350 μg/kg, 400 μg/kg, 450 μg/kg, 500 μg/kg, 550 μg/kg, 600 μg/kg, 650 μg/kg, 700 μg/kg, 750 μg/kg, 800 μg/kg, 850 μg/kg, 900 μg/kg, 950 μg/kg, 1000 μg/kg, 0.1 to 5 mg/kg, or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months, or yearly.

The administration of the pharmaceutical compositions of the present disclosure can be performed in a variety of ways, including orally, subcutaneously, intravenously, intracerebrally, intranasally, transdermally, intraperitoneally, intramuscularly, intrapulmonary, intrathecally, vaginally, rectally, intraocularly, or in any other acceptable manner. The pharmaceutical compositions can be administered continuously by infusion, although bolus injection is acceptable, using techniques well known in the art, such as pumps (e.g., subcutaneous osmotic pumps) or implantation. In some instances the pharmaceutical compositions can be directly applied as a solution or spray.

Particular embodiments provide for pharmaceutical compositions including any one or more of the compounds described herein, for the purpose of treating and/or preventing disease in a subject. Additional embodiments provide for pharmaceutical compositions alone or in combination with an antigen. As such, in some embodiments the pharmaceutical compositions can be used as vaccines.

The disclosure provides for the use of the compounds as adjuvants.

The compounds, pharmaceutical compositions, and methods disclosed herein can be additive or synergistic with other therapies currently in development or use. For example, ribavirin and interferon-α provide an effective treatment for HCV infection when used in combination. Their efficacy in combination can exceed the efficacy of either drug product when used alone. The pharmaceutical compositions of the disclosure can be administered alone or in combination or conjunction with interferon, ribavirin, and/or a variety of small molecules that are being developed against both viral targets (viral proteases, viral polymerase, and/or assembly of viral replication complexes) and host targets (host proteases required for viral processing, host kinases required for phosphorylation of viral targets such as NS5A, and inhibitors of host factors required to efficiently utilize the viral internal ribosome entry site, or IRES).

The pharmaceutical compositions disclosed herein could be used in combination or conjunction with adamantane inhibitors, neuraminidase inhibitors, alpha interferons, non-nucleoside or nucleoside polymerase inhibitors, NS5A inhibitors, antihistamines, protease inhibitors, helicase inhibitors, P7 inhibitors, entry inhibitors, IRES inhibitors, immune stimulators, HCV replication inhibitors, cyclophilin A inhibitors, A3 adenosine agonists, and/or microRNA suppressors.

Cytokines that could be administered in combination or conjunction with the pharmaceutical compositions disclosed herein include interleukin (IL)-2, IL-12, IL-23, IL-27, or IFN-γ.

New HCV drugs that are, or will be, available for potential administration in combination or conjunction with the pharmaceutical compositions disclosed herein include ACH-1625 (Achillion); Glycosylated interferon (Alios Biopharma); ANA598, ANA773 (Anadys Pharm); ATI-0810 (Arisyn Therapeutics); AVL-181 (Avila Therapeutics);

LOCTERON® (Biolex); CTS-1027 (Conatus); SD-101 (Dynavax Technologies); Clemizole (Eiger Biopharmaceuticals); GS-9190 (Gilead Sciences); GI-5005 (GlobalImmune BioPharma); Resiquimod/R-848 (Graceway Pharmaceuticals); Albinterferon alpha-2b (Human Genome Sciences); IDX-184, IDX-320, IDX-375 (Idenix); IMO-2125 (Idera Pharmaceuticals); INX-189 (Inhibitex); ITCA-638 (Intarcia Therapeutics); ITMN-191/RG7227 (Intermune); ITX-5061, ITX-4520 (iTherx Pharmaceuticals); MB11362 (Metabasis Therapeutics); Bavituximab (Peregrine Pharmaceuticals); PSI-7977, RG7128, PSI-938 (Pharmasset); PHX1766 (Phenomix); Nitazoxanide/ ALINIA[8] (Romark Laboratories); SP-30 (Samaritan Pharmaceuticals); SCV-07 (SciClone); SCY-635 (Scynexis); TT-033 (Tacere Therapeutics); Viramidine/taribavirin (Valeant Pharmaceuticals); Telaprevir, VCH-759, VCH-916, VCH-222, VX-500, VX-813 (Vertex Pharmaceuticals); and PEG-INF Lambda (Zymogenetics).

New influenza and WNV drugs that are, or will be, available for potential administration in combination or conjunction with the pharmaceutical compositions disclosed herein include neuraminidase inhibitors (Peramivir, Laninamivir); triple therapy neuraminidase inhibitors, ribavirin, and amantadine (ADS-8902); polymerase inhibitors (Favipiravir); reverse transcriptase inhibitor (ANX-201); inhaled chitosan (ANX-211); entry/binding inhibitors (Binding Site Mimetic, Flucide); entry inhibitor, (Fludase); fusion inhibitor, (MGAWN1 for WNV); host cell inhibitors (Iantibiotics); cleavage of RNA genome (RNAi, RNAse L); immune stimulators (Interferon, Alferon-LDO; Neurokinin1 agonist, Homspera, Interferon Alferon N for WNV); and TG21.

Other drugs for treatment of influenza and/or hepatitis that are available for potential administration in combination or conjunction with the pharmaceutical compositions include PEGinterferon alfa-2a (Pegasys), PEGinterferon alfa-2b (Peg-Intron), ribavirin (Copegus; Rebetol), oseltamivir (Tamiflu), zanamivir (Relenza), amantadine, and rimantadine.

These agents can be incorporated as part of the same pharmaceutical composition or can be administered separately from the compounds of the disclosure, either concurrently or in accordance with another treatment schedule.

The compounds or pharmaceutical compositions can be additive or synergistic with other compounds or pharmaceutical compositions to enable vaccine development. By virtue of their antiviral and immune enhancing properties, the compounds can be used to affect a prophylactic or therapeutic vaccination. The compounds need not be administered simultaneously or in combination with other vaccine components to be effective. The vaccine applications of the compounds are not limited to the treatment of viral infection but can encompass all therapeutic and prophylactic vaccine applications due to the general nature of the immune response elicited by the compounds.

A "vaccine" is an immunogenic preparation that is used to induce an immune response in an individual. A vaccine can have more than one constituent that is immunogenic. A vaccine can be used for prophylactic and/or therapeutic purposes. A vaccine does not necessarily have to prevent viral infections. Without being bound by theory, the vaccines of the disclosure can affect an individual's immune response in a manner such that viral infection occurs in a lesser amount (including not at all) or such that biological or physiological effects of the viral infection are ameliorated when the vaccine is administered as described herein. As used herein, vaccines include preparations including pharmaceutical compositions including the compounds, alone or in combination with an antigen, for the purpose of treating a viral infection in a subject including a vertebrate animal.

The disclosure provides for the use of the compounds and pharmaceutical compositions as adjuvants. An adjuvant enhances, potentiates, and/or accelerates the beneficial effects of another administered therapeutic agent. In particular embodiments, the term "adjuvant" refers to compounds that modify the effect of other agents on the immune system. Adjuvants that possess this function may also be inorganic or organic chemicals, macromolecules, or entire cells of certain killed bacteria, which enhance the immune response to an antigen. They may be included in a vaccine to enhance the recipient's immune response to the supplied antigen.

As is understood by one of ordinary skill in the art, vaccines can be against viruses, bacterial infections, cancers, etc. and can include one or more of a live attenuated vaccine (LAIV), an inactivated vaccine (IIV; killed virus vaccine), a subunit (split vaccine); a sub-virion vaccine; a purified protein vaccine; or a DNA vaccine. Appropriate adjuvants include one or more of water/oil emulsions, non-ionic copolymer adjuvants, e.g., CRL 1005 (Optivax; Vaxcel Inc., Norcross, Ga.), aluminum phosphate, aluminum hydroxide, aqueous suspensions of aluminum and magnesium hydroxides, bacterial endotoxins, polynucleotides, polyelectrolytes, lipophilic adjuvants and synthetic muramyl dipeptide (norMDP) analogs such as N-acetyl-nor-muranyl-L-alanyl-D-isoglutamine, N-acetyl-muranyl-(6-O-stearoyl)-L-alanyl-D-isoglutamine, or N-Glycol-muranyl-LalphaAbu-D-isoglutamine (Ciba-Geigy Ltd.).

The present disclosure further includes the use and application of the compounds and pharmaceutical compositions in vitro in a number of applications including developing therapies and vaccines against viral infections, research in modulation of the innate immune response in eukaryotic cells, etc. The compounds and pharmaceutical compositions disclosure can also be used in animal models. The results of such in vitro and animal in vivo uses of the compounds and pharmaceutical compositions can, for example, inform their in vivo use in humans, or they can be valuable independent of any human therapeutic or prophylactic use.

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure. For example, the Examples below provide in vitro methods for testing the compounds of the disclosure. Other in vitro and/or in vivo virus infection models include flaviviruses such as DNV, bovine diarrheal virus, WNV, and GBV-C virus, other RNA viruses such as RSV, SARS, and the HCV replicon systems. Furthermore, any appropriate cultured cell competent for viral replication can be utilized in the antiviral assays.

EXPERIMENTAL EXAMPLES

Example 1

General Synthesis Methods

The compounds of the disclosure may be prepared by the methods described below, together with synthetic methods familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-VI (published by Wiley-Interscience)). Preferred methods include those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999.

Compounds of the disclosure, or their pharmaceutically acceptable salts, can be prepared according to the reaction Schemes described below. These methods can be modified or adapted in ways known to chemists of ordinary skill in order to achieve synthesis of additional compounds within the scope of the present invention. Such modification was done to synthesize an exemplary compound of the invention as described in Examples 2 and 3. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the disclosure in any way.

Synthesis of N-(4-hydroxy-2-methyl-1,3-benzothiazol-5-yl)acetamide

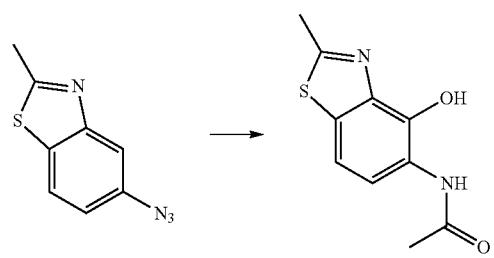

0.6 g of commercially available 5-azido-2-methyl-1,3-benzothiazole and 5 g of acetic acid were heated to 100° C. for 20 minutes. Evaporation and column chromatography purification of the residue afforded 0.43 g of N-(4-hydroxy-2-methyl-1,3-benzothiazol-5-yl)acetamide.

Synthesis of 5-amino-2-methyl-1,3-benzothiazol-4-ol

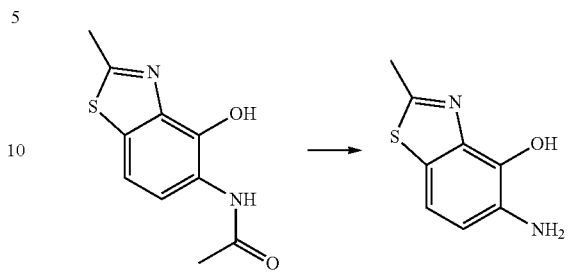

0.4 g of the acetamide was treated with 2 mL concentrated HCl. Evaporation provided 0.38 g of 5-amino-2-methyl-1,3-benzothiazol-4-ol as the di-HCl salt.

Synthesis of 7-methyl[1,3]thiazolo[5,4-g][1,3]benzoxazol-2-amine

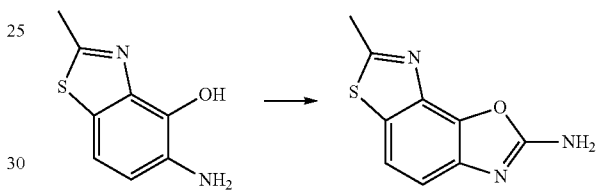

To a solution of 5 mL 3:4 methanol:water solution cooled to 0° C. was added 0.08 mL bromine followed by 0.12 g of KCN in portions. When the bromine color was gone the cyanogen bromide solution was added to 0.38 g of the amine dihydrochloride in 20 mL water and 0.252 g sodium bicarbonate and the reaction was left overnight. The reaction was filtered and the filtrate was treated with sodium bicarbonate and concentrated under vacuum. The residue was dissolved in ethanol and the solution was filtered. The filtrate was concentrated to a residue which was purified by chromatography to afford 0.14 of 7-methyl[1,3]thiazolo[5,4-g][1,3]benzoxazol-2-amine.

Example 2

Synthesis of N-(7-methyl[1,3]thiazolo[5,4-g][1,3]benzoxazol-2-yl)thiophene-2-carboxamide Acid chloride coupling was performed:

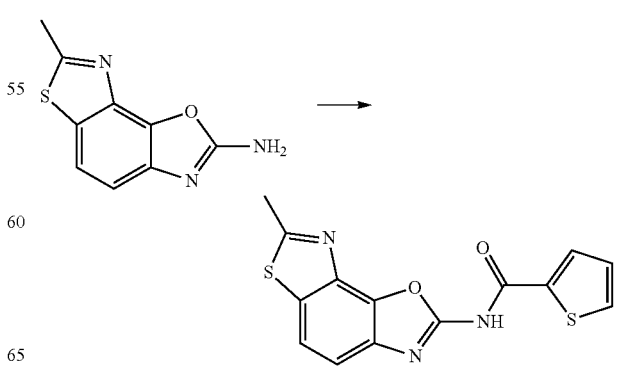

To a suspension of 0.15 g 7-methyl[1,3]thiazolo[5,4-g][1,3]benzoxazol-2-amine in 2.5 mL dry pyridine was added 0.078 mL thiophene-2-carbonyl chloride. The reaction was stirred for 5 h at 80° C. then cooled to room temperature. 4 mL of water was added and the precipitate was filtered off, washed with water and dried to afford 0.154 g of N-(7-methyl[1,3]thiazolo[5,4-g][1, 3]benzoxazol-2-yl)thiophene-2-carboxamide.

Example 3

Synthesis of N-[6-(pyrrolidine-1-sulfonyl)-1,3-benzothiazol-2-yl]naphthalene-2-carboxamide The intermediate 6-(pyrrolidin-1-ylsulfonyl)-1,3-benzothiazol-2-amine, which was used in the synthesis of N-[6-(pyrrolidine-1-sulfonyl)-1,3-benzothiazol-2-yl]naphthalene-2-carboxamide, was synthesized as described below:

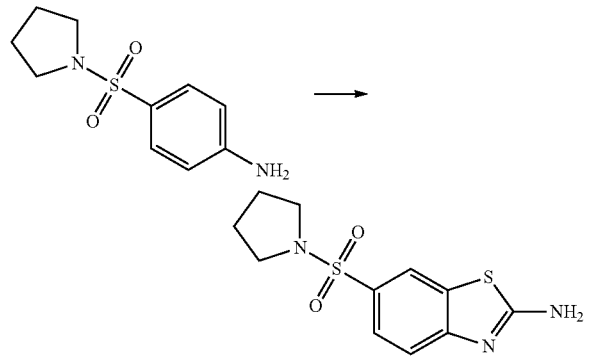

A mixture of commercially available 4-(pyrrolidin-1-ylsulfonyl)aniline (1.0 g) and ammonium thiocyanate (1.01 g) was suspended in 25 mL acetic acid and heated to 90° C. The mixture was cooled to 15° C. and liquid bromine (0.22 mL) was added dropwise. The reaction was stirred at room temperature overnight then filtered. The filtrate was concentrated under vacuum and the residue was added to a solution of aqueous sodium bicarbonate and stirred for 1 hour. The precipitate was filtered off, washed with water and ether and dried to afford 0.7 g of 6-(pyrrolidin-1-ylsulfonyl)-1,3-benzothiazol-2-amine.

0.1 g of 6-(pyrrolidin-1-ylsulfonyl)-1,3-benzothiazol-2-amine was dissolved in 2 mL dry pyridine and 2-naphthoyl chloride (0.067 g) was added and the mixture was stirred at 80° C. for 5 h. After cooling to room temperature the mixture was added to 0.7 mL water and the precipitate was filtered off, washed with water and ether and dried to afford 0.091 g of N-[6-(pyrrolidine-1-sulfonyl)-1,3-benzothiazol-2-yl]naphthalene-2-carboxamide:

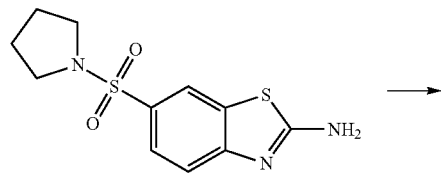

-continued

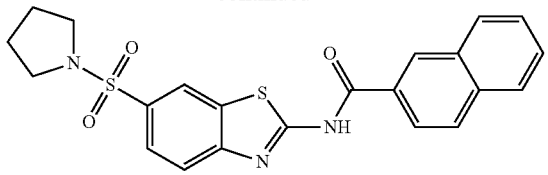

Example 4

Antiviral Activity and Pharmacological Properties Using Structure-Activity Relationship (SAR) Studies This Example describes optimization of compounds for antiviral action. First, a small analog derivative set is used to define a structural class. The active analogs that are identified in this first stage are then used to define a subset of structural classes of interest for further optimization (Stage 2).

Stage 2 focuses on creating structural diversity and evaluating core variants for derivative expansion. Structural derivatives are tested for biological activity including the IRF-3 translocation assay, antiviral activity, and cytotoxicity in one or more cell lines or peripheral blood mononuclear cells. Optimized molecules that show improved efficacy and low cytotoxicity are further characterized by additional measures of in vitro toxicology and absorption, distribution, metabolism, and elimination (ADME). Their mechanism of action and breadth of antiviral activity are also studied.

To design analog structures, the drug-like properties, metabolic lability, and toxic potential of the lead compounds are analyzed. Drug-like properties, as measured by Lipinski's Rules, and related physiochemical properties are primary indicators of bioavailability. Structural features that suggest metabolic and toxicological liabilities may indicate limited stability, reduced half-life, reactive intermediates, or idiosyncratic toxicity and will therefore be removed.

Compounds are tested for potent in vitro antiviral activity against viruses including HCV 2A, RSV, DNV type 2, and influenza A virus strains. Viral protein and RNA levels are assessed following drug treatment using the assays described herein. Analog design is aimed to identify lead compounds with picomolar to nanomolar potency, which is adequate to support preclinical development Lead compounds are characterized for their in vitro toxicological and ADME properties and for further mechanistic study.

In vitro pharmacology studies are performed to measure performance of the most promising analogs in one or more assays of intestinal permeability, metabolic stability and toxicity. Key in vitro characterization studies can include plasma protein binding; serum, plasma, and whole-blood stability in human and model organisms; intestinal permeability; intrinsic clearance; human Ether-á-go-go (hERG) channel inhibition; and genotoxicity.

For each analog, an HPLC- and/or HPLC-mass spectrometry-based analytical method is used to evaluate drug and metabolite concentrations in various test systems. Although the specific analytical method is optimized for each molecule, reverse-phase chromatography can be used alone or in combination with quadrupole mass spectrometry to characterize the identity and purity of several of the lead molecules. Initially, drug stability over time in increasing concentrations of serum, plasma, and whole blood from mammalian species (such as mouse, cynomolgus macaque, and human) is evaluated by HPLC, and a half-life is determined.

Prominent metabolites were characterized by mass spectrometry. Human plasma protein binding were evaluated by partition analysis using equilibrium dialysis. For intestinal permeability modeling, apical-to-basolateral flux is assessed in the human epithelial cell line TC7. Hepatic clearance is estimated for a subset of the most promising analogs by measuring the rate of disappearance of the parent compound during incubation in human liver microsomes. As above, specific metabolites can be isolated and characterized.

In vitro toxicology studies are performed to evaluate the potential cardiac and genetic toxicity of lead analogs. Automated patch-clamp is used to assess the impact of each compound on hERG channel currents in a recombinant Chinese hamster ovary (CHO) cell line transgenically expressing the human Kv11.1 gene. Concentrations up to the lesser of 30 times the maximum serum concentration or the limit of solubility of each compound are evaluated in order to determine an IC50 for the molecule on the hERG channel. A subset of compounds is evaluated over a range of concentrations for their ability to induce mutation reversion in *Salmonella typhimurium* strains TA98 and TA100 or to promote micronucleus formation in CHO cells in culture.

Example 5

Biological Activity

This Example describes methods used to identify compounds that activate innate immune responses, including activation of the RIG-I pathway. Other compounds as described herein likewise can be evaluated by the methods described in this example, and other cell types can also be used.

Cultured Huh 7 cells that were stably transfected with a luciferase reporter gene coupled with a RIG-I signaling pathway responsive promoter (IFNβ, ISG56, or ISG54 promoter) were seeded and allowed to grow overnight. The compound 1 was then added and cells were grown in the presence of compound 1 for 18-20 hours. Steady-Glo luciferase substrate (Promega) was added and luminescence was read on a luminometer (Berthold).

Figure 1B:
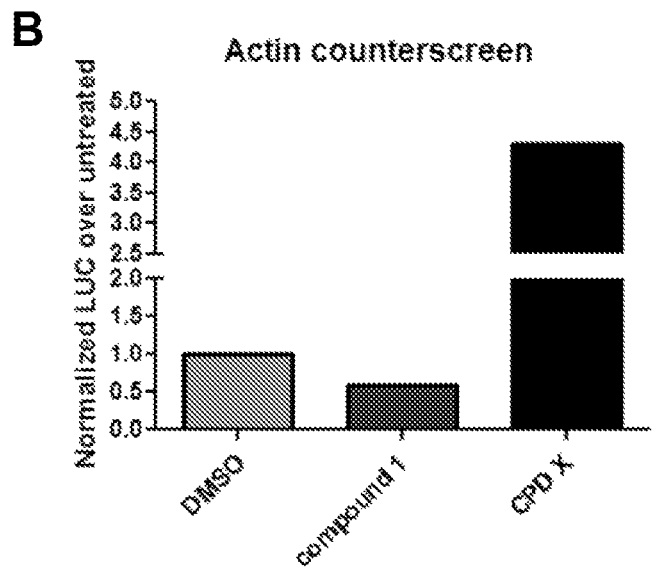

FIG. 1A shows that compound 1 of Table 1 as described herein was validated by demonstrating dose-dependent induction of the luciferase reporter gene coupled to the promoters for IFNβ ("IFNβ-LUC," left), ISG56 ("ISG56-LUC," center), and ISG54 ("ISG54-LUC," right). Additionally, compound 1 did not induce a nonspecific promoter (β-actin-LUC, FIG. 1B).

An immunofluorescent cytochemistry assay was used to determine IRF-3 activation and translocation to the nucleus. Cultured human HeLa cells were treated with increasing amounts of compound or equivalent amounts of DMSO diluted in media for 20 hours. Positive control wells were infected with 100 HA/mL Sendai virus for an equivalent time period. IRF-3 was detected using polyclonal rabbit serum specific to IRF-3 and a secondary antibody conjugated to DYLIGHT® (Pierce Biotechnology, Inc., Rockford, Ill.) 488.

An immunofluorescent cytochemistry assay was used to determine NFκB activation. The innate immune response is also dependent on activation of the NFκB transcription factor. Cultured human HeLa cells were treated with increasing amounts of compound or equivalent amounts of DMSO diluted in media for 20 hours. Positive control wells were infected with 100 HA/mL Sendai virus for an equivalent time period. NFκB was detected using monoclonal mouse antibody specific to the p65 subunit of NFκB and a secondary antibody conjugated to DyLight 488.

Figure 1C:
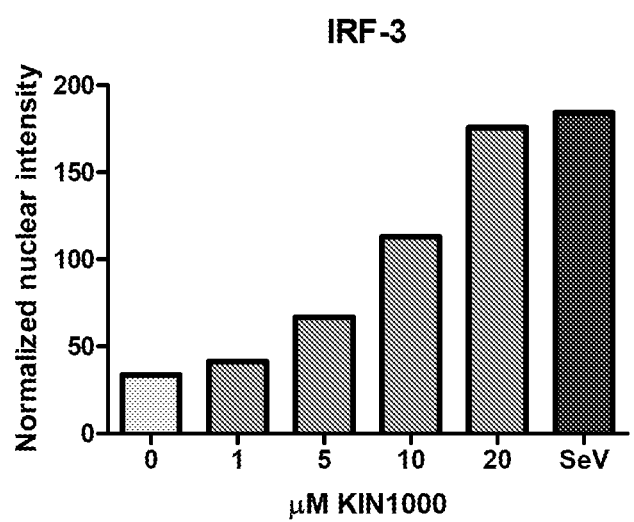
Figure 1D:
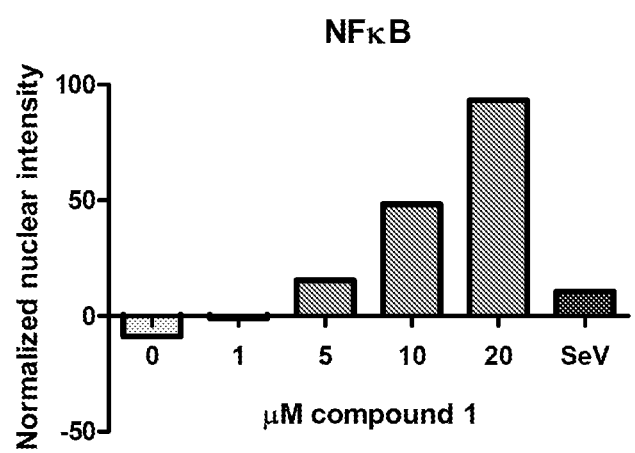

Quantification of the IRF-3 and NFκB immunofluorescent assays described herein was done as follows: 96-well plates containing cultured human cells treated with compound and stained for either IRF-3 or NFκB were scanned and quantified using the ARRAYSCAN® instrument and software (Cellomics). Activation of transcription factor was evidenced by increased nuclear intensity normalized for cytoplasmic intensity, or nuclear-cytoplasmic difference. Compound 1 shows a dose dependent increase in nuclear-cytoplasmic difference for IRF-3 (FIG. 1C) and for NFκB (FIG. 1D).

Assays for innate immune gene expression were performed in cell types including HeLa cells, PH5CH8 cells, and HUVEC primary cells. Gene expression can be similarly assayed in cell types that include: primary blood mononuclear cells, human macrophages, THP-1 cells, Huh 7 cells, A549 cells, MRC5 cells, rat splenocytes, rat thymocytes, mouse macrophages, mouse splenocytes, and mouse thymocytes. Expression of other genes of interest can be assayed as described herein.

Cultured HeLa cells were treated with 20 μM, 10 μM, 5 μM of compound or a DMSO control and incubated for up to 24 hours. Cultured PH5CH8 cells were treated with 10 μM, 5 μM, 1 μM, or a DMSO control and incubated for up to 24 hours. Primary HUVEC cells were thawed and seeded in 6-well plates at 2.4×10$^4$ cells per well and allowed to grow to 80% confluence, typically 5 days in culture with fresh media replaced every 48 hours. Compound was added at 10 μM, 1 μM or a DMSO control and incubated for up to 24 hours. Gene expression was assayed as described below.

Cells were harvested and RNA was isolated using the QIAshredder columns and RNeasy Mini Kit (Qiagen) according to manufacturer instructions. Reverse transcription was performed and the cDNA template was used for quantitative real-time PCR. PCR reactions were performed using commercially available, validated TaqMan gene expression assays (Applied Biosystems/Life Technologies) according to manufacturer instructions. Gene expression levels were measured using a relative expression analysis (ΔΔCt).

Figure 2A:
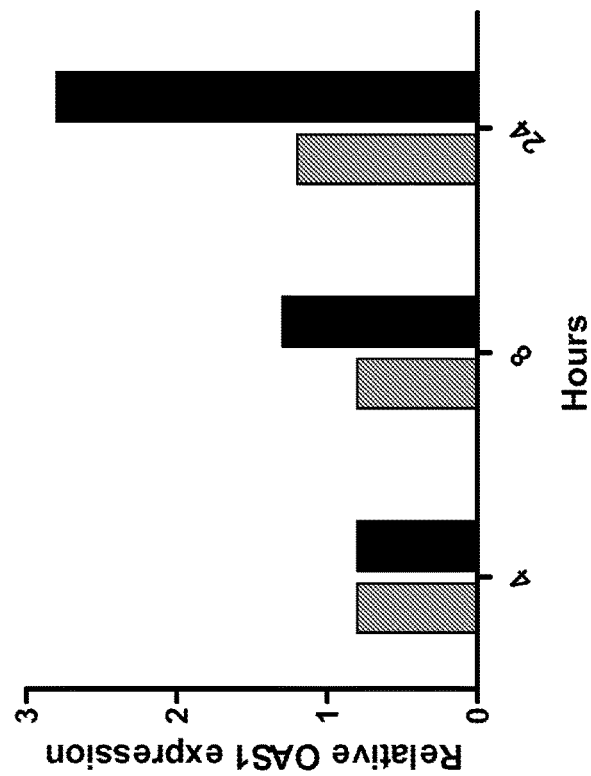
FIGS. 2A-2C show induction of gene expression by compound 1 and 2 of Table 1.
Figure 2A:
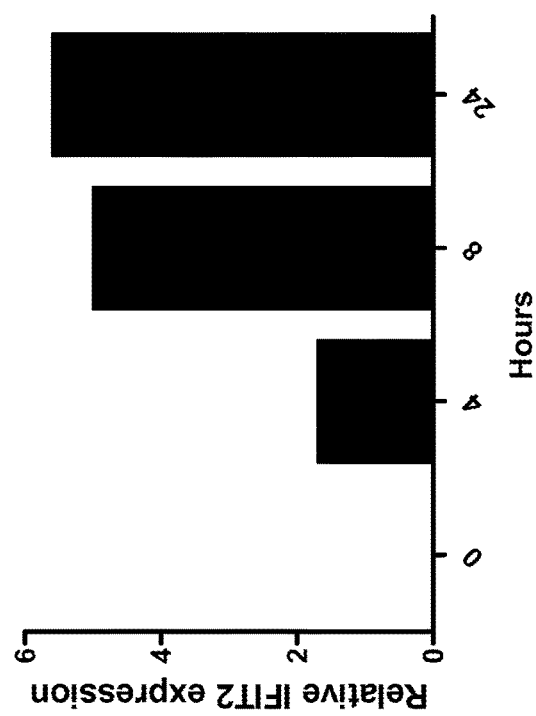
Figure 2B:
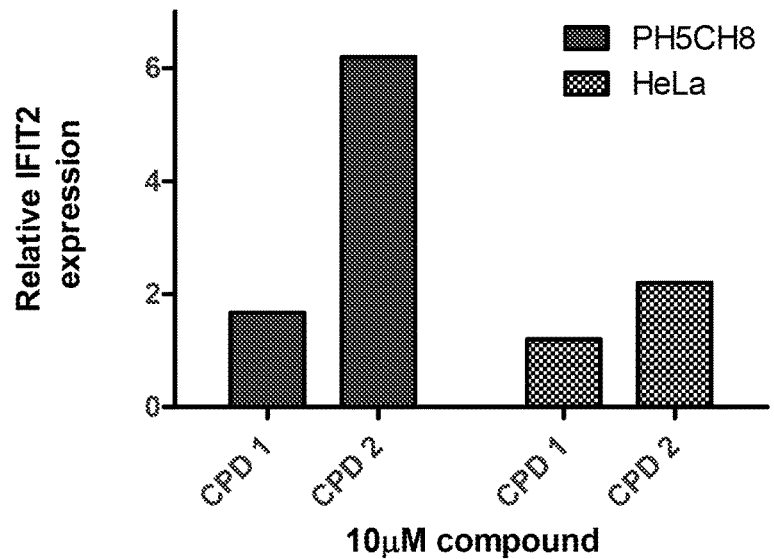
Figure 2C:
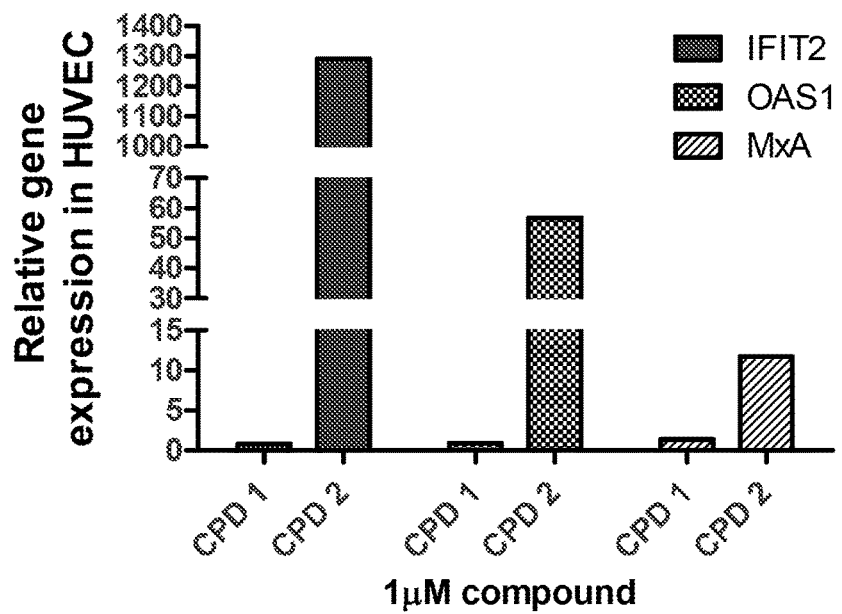

FIGS. 2A-2C show induction of gene expression by compounds 1 and 2 of Table 1. FIG. 2A shows gene expression levels of IFIT2 (left) and OAS1 (right) in HeLa cells over time from 4-24 hours post treatment with 10 μM compound 1 (grey; OAS1 only) or 10 μM compound 2 (black; IFIT2 and OAS1 both shown). FIG. 2B shows gene expression levels of IFIT2 in PH5CH8 cells (solid color bars) and HeLa cells (black checked bars) treated with 10 μM compound 1 (CPD 1) or compound 2 (CPD 2). FIG. 2C shows gene expression levels of IFIT2 (left), OAS1 (center), and MxA (right) in primary HUVEC cells that were treated with 1 μM compound 1 (CPD 1) or 1 μM compound 2 (CPD 2).

Figure 3A:
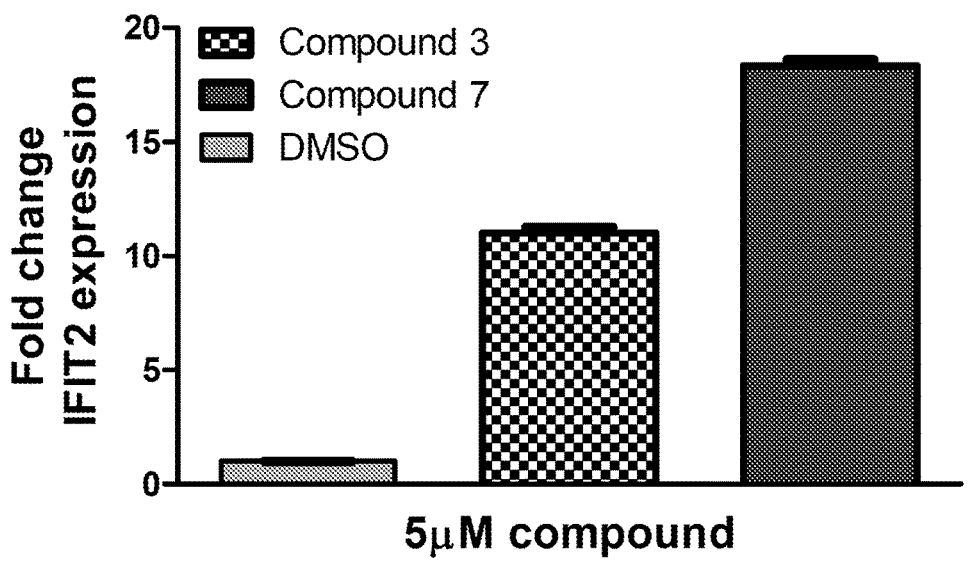
FIGS. 3A-3B show induction of gene expression by compound 3 and compound 7 of Table 1.
Figure 3B:
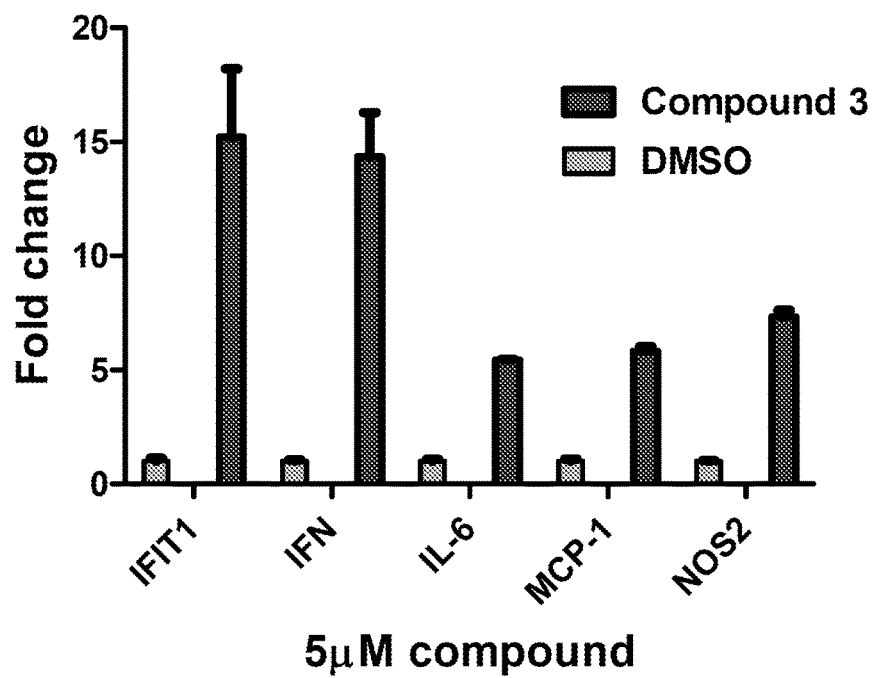

FIGS. 3A-3B show induction of gene expression by compound 3 and compound 7 of Table 1, FIG. 3A shows IFIT2 gene expression was induced by 5 μM compound 3 or compound 7. FIG. 3B shows compound 3 induced innate immune gene expression in mouse macrophage cells.

Example 6

Ex Vivo Immune Stimulatory Activity of Compound 1

The activity of compound 1 of Table 1 in primary immune cells was assayed to determine whether compound 1 stimulates immune responses. Cultured human primary dendritic cells were treated with 0, 1, or 10 µM of compound 1 for 24 hours. Supernatant from treated wells was isolated and tested for levels of cytokine protein. Cytokines were detected using specific antibodies conjugated to magnetic beads and a secondary antibody that reacts with Streptavidin/Phycoerythrin to produce a fluorescent signal. The bound beads were detected and quantified using the MAGPIX® (Luminex Corp.) instrument, although similar techniques as are known in the art may be used to measure fluorescent protein production, such as for example an ELISA.

Figure 4:
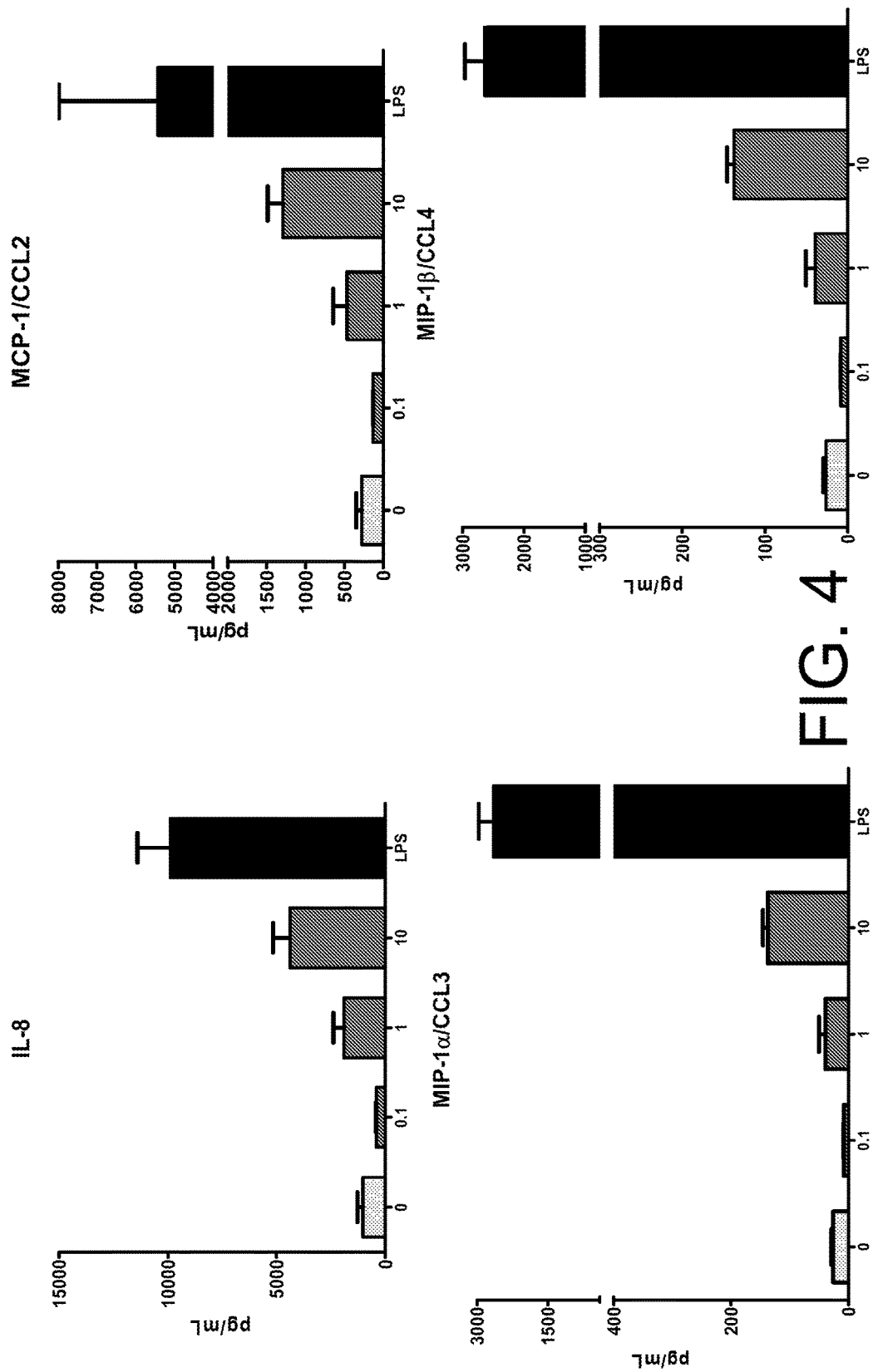
FIG. 4 shows induction of the chemokines IL-8, MCP-1, MIP-1α, and MIP-1β by dendritic cells treated with compound 1 of Table 1 (concentrations shown in µM). LPS is shown as a positive control inducer of chemokine expression.

FIG. 4 shows induction of the chemokines IL-8, MCP-1, MIP-1α, and MIP-1β by dendritic cells treated with compound 1 of Table 1 (concentrations shown in µM). LPS is shown as a positive control inducer of chemokine expression.

Other cells from which cytokine secretion can be measured include, for example human peripheral blood mononuclear cells, human macrophages, mouse macrophages, mouse splenocytes, rat thymocytes, and rat splenocytes.

Example 7

In Vitro Antiviral Activity

To further characterize the breadth of antiviral activity of optimized molecules, cell culture infection models are used to analyze different viruses, including different strains of influenza virus, HCV, DNV, RSV, and WNV, an emerging public health concern. The studies include treating cells with compound 2-24 hours prior to infection or treating cells up to 8 hours after infection. Virus production and cellular ISG expression are assessed over a time course to analyze antiviral effects of representative compounds from lead structural classes. Known antiviral treatments including IFNβ are used as a positive control.

Virus production is measured by focus-forming or plaque assay. In parallel experiments, viral RNA and cellular ISG expression are measured by qPCR and immunoblot analyses. These experiments are designed to validate compound signaling actions during virus infection, and assess compound actions to direct innate immune antiviral programs against various strains of viruses and in the setting of virus countermeasures. Detailed dose-response analyses of each compound are conducted in each virus infection system to determine the effective dose that suppresses virus production by 50% (IC50) and 90% (IC90) as compared with control cells for both the pre-treatment and post-treatment infection models.

Compounds of the current invention are tested using in vitro models against viruses including: Hepatitis B Virus (HBV), HCV H77 (genotype 1a), HVV JFH1 (genotype 2a), Influenza A/PR/8/34 (H1N1 mouse-adapted virus), Influenza A/WSN/33 (H1N1 mouse-adapted neurovirulent virus), Influenza A/TX/36/91 (H1N1 circulating virus), Influenza A/Udorn/72 (H3N2), WNV TX02 (lineage 1), WNV MAD78 (lineage 2), RSV, human coronavirus OC43 (SARS-like pathogen), and DNV type 2.

Antiviral activity of exemplary compounds of the disclosure is demonstrated in Examples 8-11 below.

Example 8

In Vitro Activity Against Respiratory Syncytial Virus

HeLa cells were seeded the previous day in 6-well plates at $4\times10^5$ cells per well. The next day, the media was replaced with RSV in media without FBS at an MOI of 0.1. Virus binding occurred at 37° C. for 2 hours. After 2 hours the cells were washed with warm complete media and replaced with media containing drug at varying concentrations of 10 µM, 5 µM, 1 µM, or a DMSO control. Cells were placed in a 37° C. incubator for 48 hours.

For virus detection and titration, HeLa cells were seeded in 96-well plates at $8\times10^3$ cells per well 24 hrs prior to collecting virus supernatant. After the 48 hour incubation period, the virus supernatant from the infected plate was harvested and used to infect these cells at a 1/10 final dilution. Cells were placed in a 37° C. incubator for 24 hours.

24 hours after infection, cells were washed twice with PBS and fixed with methanol/acetone solution. After fixing the cells were washed twice with PBS and replaced with blocking buffer (10% horse serum, 1 g/mL BSA and 0.1% Triton-100X in PBS) for 1 hour. The blocking buffer was replaced with binding buffer containing a 1/2000 dilution of primary antibody for 2 hours at room temperature. The primary antibody was a mouse monoclonal antibody against RSV. The cells were washed twice with PBS and replaced with binding buffer containing 1/3000 dilution of the Alexa Fluor-488 goat anti-mouse secondary antibody and a Hoechst nuclear stain for 1 hour at room temperature. The cells were washed twice with PBS and PBS is added to all wells. The 96-well plate was sealed and fluorescence activity associated with virus infectivity was determined by immunofluorescent assay using the Array Scan instrument (Thermo-Fischer).

Treatment with compounds can be done prior to infection. In variations of this method, the compounds are added at varying time points prior to infection with virus. Virus detection and titration is conducted as described.

Figure 5:
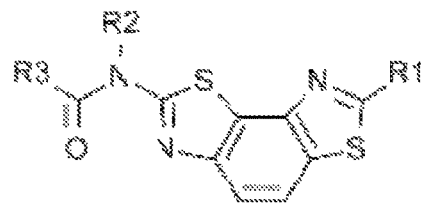
FIG. 5 shows results of experiments performed using the protocol of Example 8, demonstrating the antiviral activity of select compounds of FIG. 5 that demonstrated antiviral activity against RSV. +++=greater than 70% inhibition of infection, ++=greater than 50% inhibition, +=greater than 30% inhibition, −=less than 30% inhibition.

FIG. 5 shows results of experiments performed using the protocol of Example 8, demonstrating the antiviral activity of select compounds that demonstrated antiviral activity against RSV. +++=greater than 70% inhibition of infection, ++=greater than 50% inhibition, +=greater than 30% inhibition, −=less than 30% inhibition.

Example 9

In Vitro Activity Against Influenza Virus

Influenza A/Worn/72 infection of H292 cells. $2\times10^6$ H292 cells in RPMI1640+10% FCS were treated with 2 µM compound 2 in a final concentration of 0.5% DMSO for 6 hours. Compound-containing media was aspirated and replaced with 1×MEM containing A/Udorn/72 at an MOI of 0.1 and placed at 37° C. in a $CO^2$ incubator. Two hours post infection, virus-containing media was aspirated and replaced with 1×MEM containing 1 ug/mL TPCK-treated Trypsin, 2 µM compound 2, 0.5% DMSO. Cells were placed in 37° C. $CO_2$ incubator for 18 hours. After 20 hours post-infection, virus supernatants were collected and titered on MDCK cells.

Influenza A/Udorn/72 infection of HEK293 cells. 5×105 HEK293 cells were infected with A/Udorn/72 at an MOI of 0.2 in 1×MEM. After 2 hours post-infection, virus-containing media was aspirated and replaced with 1×MEM containing 1 µg/mL TPCK-treated Trypsin, 10 µM compound 2, 0.5% DMSO. Cells were returned to 37° C., CO2 incubator for 18 hours. After 20 hours post-infection, virus supernatants were collected and titred on MDCK cells.

Titer in MDCK cells. 10 µL of infected supernatant was added to 2×106 MDCK cells in the presence of 2 µg/mL TPCK-trypsin and placed in a 37° C. CO2 incubator. After 8 hours, supernatant was removed and cells were fixed and stained with FITC-conjugated antibody specific for Influenza NP protein. Number of foci was quantitated using the ArrayScan instrument and software (Cellomics).

Figure 6:
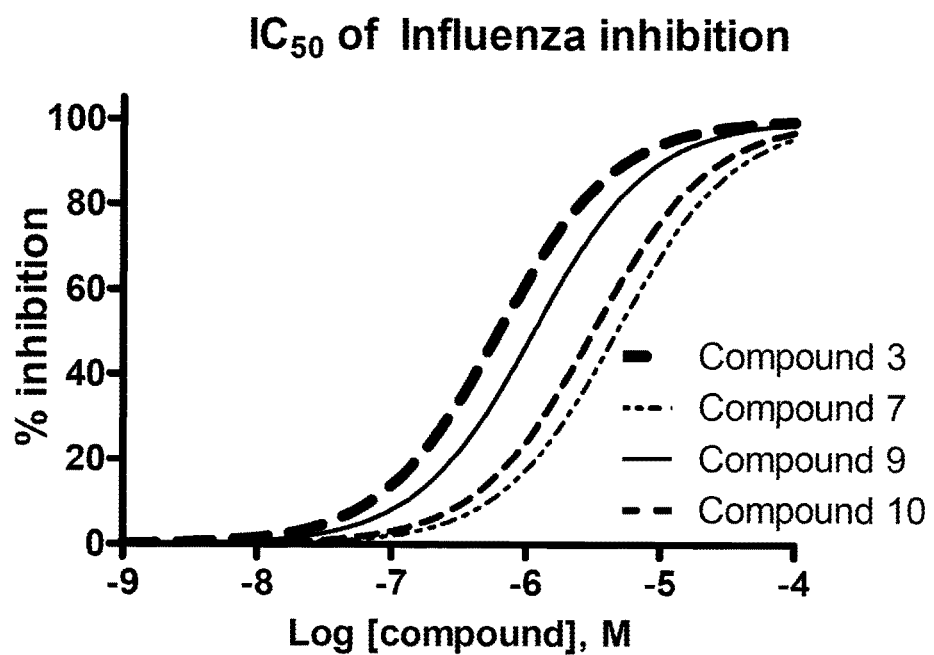
FIG. 6 shows antiviral activity of example compounds against Influenza A virus Udorn/72. Treatment of HEK293 cells with increasing concentrations of compound 3, compound 7, compound 9, and compound 10 of Table 1 resulted in dose-dependent inhibition of virus infection (shown as % untreated negative control). Calculated IC50 values are shown.

The protocol of Example 9 can be performed as described in order to evaluate the antiviral activity of example compounds. FIG. 6 shows antiviral activity of example compounds against Influenza A virus Udorn/72. Treatment of HEK293 cells with increasing concentrations of compound 3, compound 7, compound 9, and compound 10 of Table 1 resulted in dose-dependent inhibition of virus infection (shown as % untreated negative control). Calculated IC50 values are shown. Table 2 shows calculated IC50 values of selected compounds from Table 1,

TABLE 2

| IC50 against flu | |
|---|---|
| Compound | IC50 (µM) |
| 2 | 2.04 |
| 3 | 0.61 |
| 4 | 1.29 |
| 5 | >10 |
| 6 | 1.49 |
| 7 | >5 |
| 9 | 1.15 |
| 10 | 3.18 |
| 11 | 5.16 |
| 12 | 2 |
| 13 | 2 |
| 15 | 6.8 |

Example 10

In Vitro Activity Against Dengue Virus

Cultured human Huh 7 cells were seeded in 6-well tissue-culture plates at a density of $4 \times 10^5$ cells per well and grown for 24 hours. Cells were infected with DNV type 2 strain at multiplicity of infection (MOI) of 0.1 for 2 hours and then removed. Compound dilutions were prepared in 0.5% DMSO and used to treat cells at final concentrations of compound ranging 0.001 to 10 µM per well. Vehicle control wells treated with 0.5% DMSO were used to compare to drug treated cells. Replication was allowed to proceed for 48 hours. Virus supernatants were harvested and used to infect new monolayer of permissive cells, such as Vero cells that were seeded in 96-well plates at $8 \times 10^3$ cells per well 24 hrs prior to collecting virus supernatant.

The newly infected cells were incubated for 24 hours and used to measure the level of infectious virus in the original supernatants by immunofluorescent staining of viral protein. The cells were fixed with ice-cold 1:1 methanol and acetone solution and stained for DNV fusion protein. Primary mouse monoclonal antibody against DNV fusion protein (Millipore) was used at 1:2000 dilution. Secondary goat anti-mouse antibody conjugated to Alexa Fluor 488 dye (Invitrogen) and Hoescht Dye (nuclear staining) are used at 1:3000 to detect DNV protein and cell nuclei. Following secondary antibody incubation, the monolayers were washed and left in 100 µL PBS for imaging and quantitation using a Cellomics ArrayScan HCS instrument.

Figure 7:
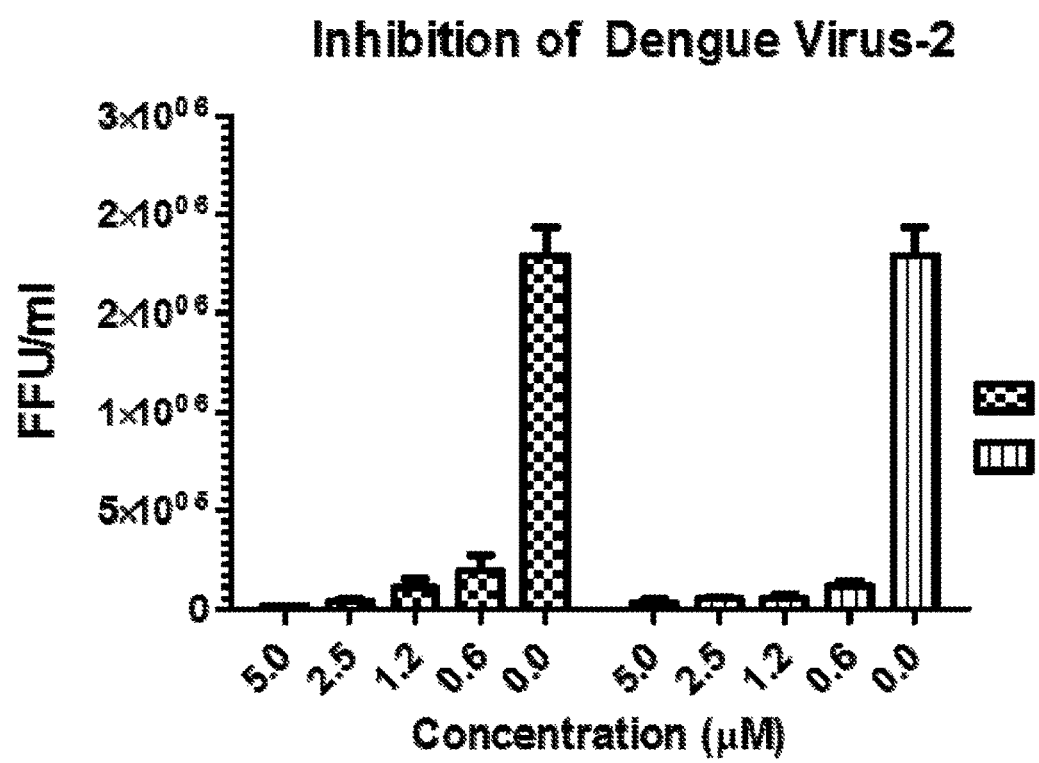
FIG. 7 shows the antiviral activity of compound 5 and compound 20 of Table 1 against Dengue virus (DNV) type 2. Treatment with increasing amounts of the compounds showed dose-dependent decrease in infection by virus.

FIG. 7 shows the antiviral activity of compound 5 and compound 20 of Table 1 against Dengue virus (DNV) type 2. Treatment with increasing amounts of compound showed dose-dependent decrease in infection by virus.

Figure 8:
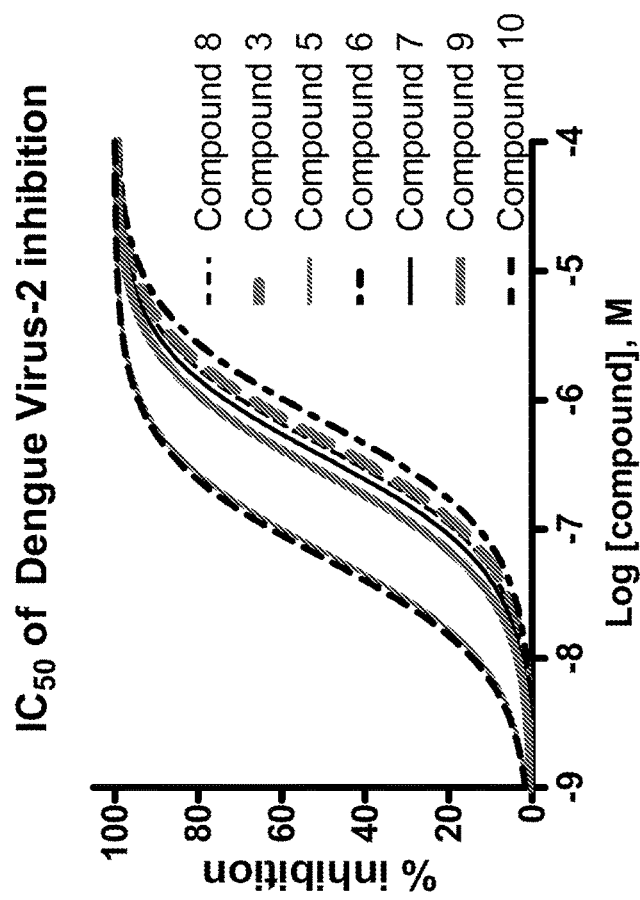
FIG. 8 shows antiviral activity of example compounds against DNV type 2. Treatment of Huh 7 cells with increasing concentrations of compound 8, compound 3, compound 5, compound 6, compound 7, compound 9, and compound 10 of Table 1 resulted in dose-dependent inhibition of virus infection (shown as % untreated negative control). Calculated IC50 values are shown.

FIG. 8 shows antiviral activity of exemplary compounds against Dengue virus type 2. Treatment of Huh 7 cells with increasing concentrations of compound 8, compound 3, compound 5, compound 6, compound 7, compound 9, and compound 10 of Table 1 resulted in dose-dependent inhibition of virus infection (shown as % untreated negative control). Calculated IC50 values are shown.

Table 3 shows calculated IC50 values of selected compounds against Dengue virus type 2 (DV2) and/or Dengue virus type 4 (DV4).

TABLE 3

| IC50 against DNV | | |
|---|---|---|
| Compound | IC50 against DV2 (µM) | IC50 against DV4 (µM) |
| 2 | 6.18 | |
| 3 | 1.87 | 0.78 |
| 4 | 3.65 | |
| 5 | 0.47 | 4.9 |
| 6 | 2.03 | 0.02 |
| 7 | 0.74 | 1.87 |
| 8 | 1.23 | |
| 9 | 1.78 | |
| 10 | 1.78 | 6.48 |
| 11 | 0.53 | |
| 21 | 0.10 | 0.27 |
| 12 | 0.14 | 0.15 |
| 14 | 0.15 | 0.03 |
| 15 | 0.39 | >5 |
| 16 | >5 | |
| 17 | 0.50 | 4.7 |

Example 11

In Vitro Activity Against Human Coronavirus

MRC5 cells were seeded the previous day in 6-well plates and grown for 24 hours. Cells were infected with human coronavirus OC43 (HCoV-OC43) for 2 hours and then removed. Compound dilutions were prepared in 0.5% DMSO and used to treat cells at final concentrations of compound ranging 0.001 to 10 µM per well. Vehicle control wells treated with 0.5% DMSO were used to compare to drug treated cells. Replication was allowed to proceed for 5 days. Virus supernatants were harvested and used to infect new monolayer of permissive cells, such as Huh 7 cells that were seeded in 96-well plates 24 hours prior to collecting virus supernatant, i.e., 4 days post infection.

The newly infected cells were incubated for 48 hours and used to measure the level of infectious virus in the original supernatants by immunofluorescent staining of viral protein. The cells are fixed with ice-cold 1:1 methanol and acetone solution and stained for HCoV-OC43 nucleoprotein. Primary mouse monoclonal antibody against HCoV-OC43 nucleoprotein (Millipore) is used at 1:1000 dilution. Secondary goat anti-mouse antibody conjugated to Alexa Fluor 488 dye (Invitrogen) and Hoescht Dye (nuclear staining) were used at 1:3000 to detect OC43 protein and cell nuclei. Following secondary antibody incubation, the monolayers were washed and left in 100 µL PBS for imaging and quantitation using a Cellomics ArrayScan HCS instrument.

Figure 9:
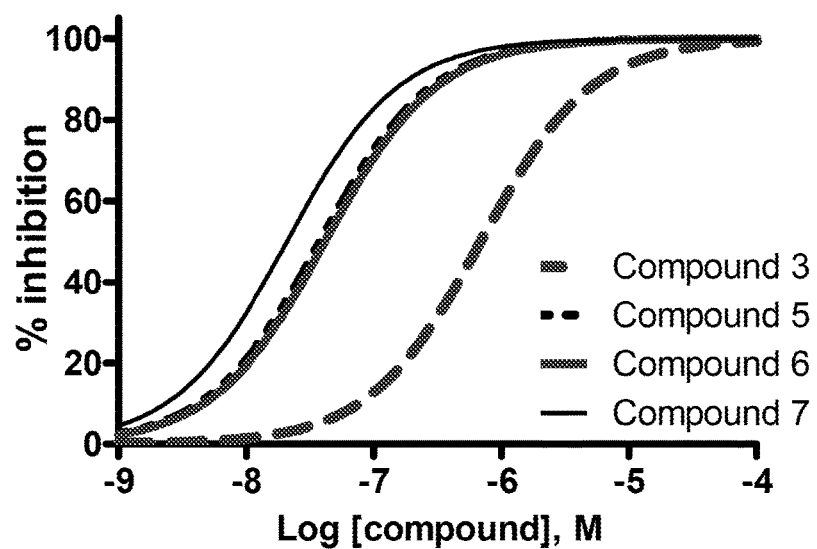
FIG. 9 shows antiviral activity of example compounds against human coronavirus OC43. Treatment with increasing concentrations of compound 3, compound 5, compound 6, and compound 7 of Table 1 resulted in dose-dependent inhibition of virus infection (shown as % untreated negative control). Calculated IC50 values are shown.

FIG. 9 shows antiviral activity of exemplary compounds against human coronavirus OC43. Treatment with increasing concentrations of compound 3, compound 5, compound 6, and compound 7 of Table 1 resulted in dose-dependent inhibition of virus infection (shown as % untreated negative control). Calculated 1050 values are shown.

Table 4 shows calculated IC50 values of selected compounds against human coronavirus OC43.

TABLE 4

| IC50 against OC43 | |
|---|---|
| Compound | IC50 (µM) |
| 2 | 9.22 |
| 3 | 0.54 |
| 4 | 0.09 |
| 5 | 0.04 |
| 6 | 0.04 |
| 7 | 0.02 |

Example 12

In Vivo Pharmacokinetic and Toxicological Properties of Compounds

The in vivo pharmacokinetic (PK) profile and tolerability/toxicity of the compounds described herein are evaluated in order to conduct further characterization of their antiviral activity in vivo.

A reverse-phase, HPLC-MS/MS detection method is used for measuring the concentration of each compound in mouse plasma. Prior to PK profiling, an initial oral and intravenous formulation for each compound is developed using a limited formulation component screen that is largely focused on maximizing aqueous solubility and stability over a small number of storage conditions. Any of the analytical methods as are known in the art can be used to measure formulation performance. A formulation is developed for each compound following a three tiered strategy:

Tier 1: pH (pH 3 to 9), buffer, and osmolality adjustment
Tier 2: addition of ethanol (<10%), propylene glycol (<40%), or polyethylene glycol (PEG) 300 or 400 (<60%) co-solvents to enhance solubility
Tier 3: addition of N—N-dimethylacetamide (DMA, <30%), N-methyl-2-pyrrolidone (NMP, <20%), and/or dimethyl sulfoxide (DMSO, <20%) co-solvents or the cyclodextrins (<40%) as needed to further improve solubility.

Example 13

In Vivo Antiviral Activity of Compounds

For compounds that demonstrate adequate performance in in vitro antiviral, mechanistic, ADME, and toxicology studies, a preliminary mouse PK study is performed. Each compound is administered as a single dose to animals by oral gavage (<10 ml/kg) or i.v. bolus injection (<5 ml/kg) after an overnight fast. Multiple animals are dosed for each dosing group such that 3 animals can be sampled at each time point. Blood samples are collected by retro-orbital sinus prior to dosing and at 5, 15, and 30 minutes, and 1, 2, 4, 8, and 24 hours post-dosing. Drug concentrations are measured according to the previously developed bioanalytical method. PK parameters are evaluated using the WinNonlin software.

Based upon performance in exploratory PK studies, compounds are further evaluated for preliminary tolerability and toxicity in mice prior to their characterization in antiviral models. Tolerability studies are performed in two stages: an initial dose escalation stage (up to 5 doses, each separated by a 5-day washout period) to determine the maximum tolerable dose (MTD, Phase 1), followed by seven daily administrations of the MTD to evaluate acute toxicity (Stage 2). All doses are administered by oral gavage. In an example experiment, five animals of each sex are placed on-study in stage 1 and 15 animals per sex per dosing group in Stage 2. Study endpoints include a determination of the MTD, physical examination, clinical observations, hematology, serum chemistry and animal bodyweights. Gross pathology is performed on all animals whether found dead, euthanized in extremis, or at the intended conclusion of the experiment. The toxicology studies are primarily exploratory in nature and intended to identify early toxicological endpoints, and drive selection of lead candidates for antiviral animal models.

Example methods to complete the PK and tolerability studies described above are shown in Table 5. These methods may be modified and/or adapted such as a different route of administration, in order to more accurately measure the pharmacological properties of a compound.

TABLE 5

| Study | Experimental design | Route of administration | Outcomes |
|---|---|---|---|
| Mouse PK | Single dose pharmacokinetic study | IV and Oral | Oral bioavailability, $C_{max}$, $t^{1/2}$, Cl, $V_d$, $AUC_{0-24, 0-\infty}$ |
| Mouse tolerability | Phase 1: ascending dose tolerability and MTD determination; Phase 2: placebo controlled 7-day toxicity at MTD | Oral | MTD, acute toxicity, hematology, serum chemistry, gross pathology |

Figure 10:
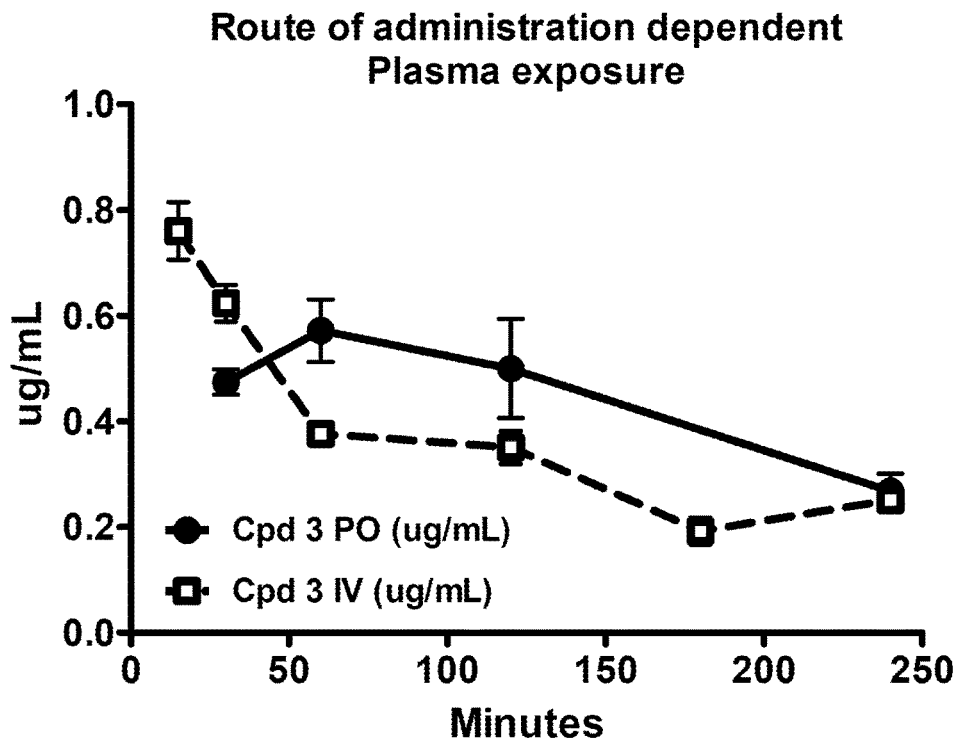
FIG. 10 shows results from exploratory pharmacokinetic (PK) studies.
Figure 10:
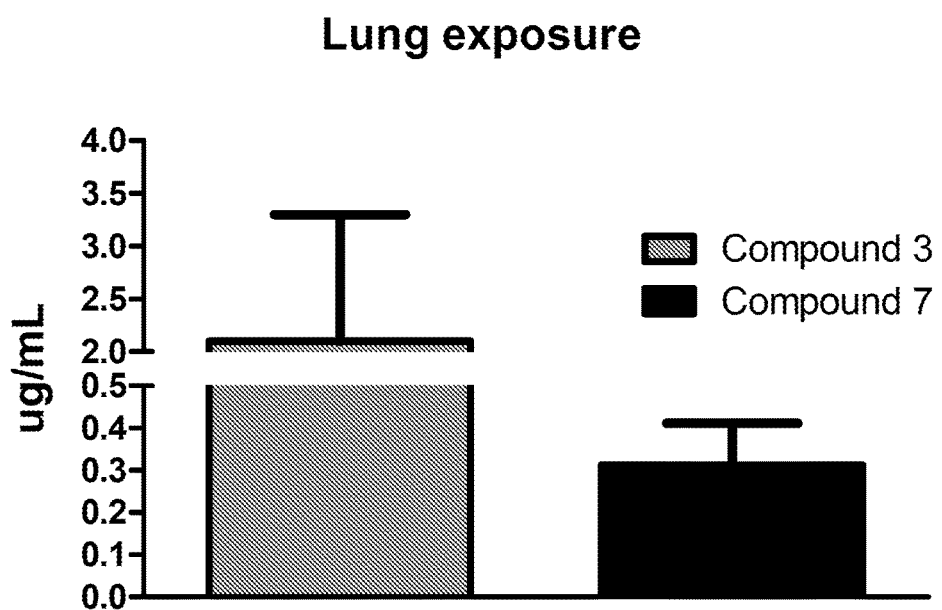

FIG. 10 shows results from exploratory PK studies. Administration of compound 3 of Table 1 via oral (PO) or intravenous (IV) route resulted in detectable levels of compound in serum samples obtained up to 250 minutes post treatment (FIG. 10A). At 4 hours post treatment of compound 3 and compound 7 of Table 1, there was detectable compound in lung tissue (FIG. 10B).

Example compounds of the disclosure that demonstrate desirable PK properties, tolerability, antiviral potency, and/or innate immune activating activity, are selected for further evaluation in preclinical mouse models of infection.

Incorporated in the design of these experiments is the determination of an effective dose for 50% and 90% suppression of serum viral load (EC50 and EC90) by each compound after a standard challenge of virus; for example, 100 pfu of WNV-TX or 1,000 pfu of influenza virus. Virus quantification in serum and/or target tissues are determined by established assay methods including: plaque assay, TCID50 assay, focus forming assay, viral protein quantification such as through HA assay or BCA assay, viral RNA quantification such as through qPCR, and/or antigen quantification such as through ELISA.

The compound actions are tested in virus challenge studies at a minimum of 2 dose levels including the determined EC50 and EC90 to evaluate their ability to limit viral pathogenesis, virus replication, and virus spread. Mice are monitored for morbidity and mortality over a range of challenge doses (for example, 10 to 1,000 pfu of virus) either alone or in combination with compound treatment beginning 12 hours before or 24 hours after infection and continuing daily subject to the determined plasma half-life of the drug. Compound dose-response analysis and infection time course studies are also conducted to evaluate compound efficacy to: 1) limit serum viral load, 2) limit virus replication and spread in target organs, and 3) protect against viral pathogenesis.

Studies to define effective dosage of drug in vivo and established mouse virus infection models are described in Table 6, although this list is not intended to be complete and the compounds can be tested in any mouse model for potency against any virus infection.

TABLE 6

| Study | Experimental design | Analysis | Outcomes |
|---|---|---|---|
| Compound dose determination | Drug measured in blood at ≥3 dose levels; 2, 8, 24 hours post treatment | Drug concentration in blood; HPLC reverse phase | Define in vivo compound exposure |
| Effective compound dose determination | Viral burden analysis at ≥3 dose levels | Viral burden analysis in serum and/or target tissues | Define in vivo $EC_{50}$ and $EC_{90}$ |
| Viral pathogenesis study 1: $EC_{50}$ and $EC_{90}$ Treatment | Treatment at defined doses of $EC_{50}$ and $EC_{90}$ | Time to moribund state, clinical scoring for pathologic signs of infection | Define compound action toward limiting viral pathogenesis |
| Viral pathogenesis study 2: $EC_{50}$ and $EC_{90}$ treatment and time course analysis | Treatment at defined doses of $EC_{50}$ and $EC_{90}$ | Viral burden analysis in serum and various target organs | Define compound action toward limiting virus replication and spread |
| Mouse WNV neuroinvasion Model | Intracranial injection of WNV-TX; drug treatment at 2 doses w/ placebo | Time to moribund state, clinical scoring for pathologic signs of infection | Define compound action toward limiting viral pathogenesis in the CNS |
| Mouse Influenza Model | Intranasal or tracheal instillation of A/PR/8/34, A/WSN/33 or A/Udorn/72; drug treatment at 2 doses w/ placebo | Mortality, viral titer in serum/target organs, body temp., clinical observations, bodyweight, cytokine levels, gene expression, markers of inflammation | Define compound action toward limiting viral pathogenesis, virus replication, and spread |
| Mouse RSV Model | Intranasal or tracheal instillation of RSV A2 Long strain; drug treatment at 2 doses w/ placebo control | Mortality, viral titer in serum/target organs, body temp., clinical observations, bodyweight, cytokine levels, gene expression, markers of inflammation | Define compound action toward limiting viral pathogenesis, virus replication, and spread |
| Mouse DNV Model | IP injection of DV-2; drug treatment at 2 doses w/ placebo | Mortality, viral titer in serum/target organs, body temp., clinical observations, bodyweight, cytokine levels, gene expression, markers of inflammation | Define compound action toward limiting viral pathogenesis, virus replication, and spread |
| Mouse MHV-1 Model | Intranasal instillation of MHV-1; drug treatment at 2 doses w/ placebo | Mortality, viral titer in serum/target organs, body temp., clinical observations, bodyweight, cytokine levels, gene expressions, markers of inflammation | Define compound action toward limiting viral pathogenesis, virus replication, and spread |

Mouse WNV model. Efficacy of compounds against WNV can be assayed after subcutaneous or intracranial (neuroinvasion) infection of virus. Compounds are administered daily by oral gavage or IP administration over the entire course of infection at 2 dose levels plus a placebo control group. Animals are evaluated for study endpoints including daily clinical observations, mortality, body weight, and body temperature. Virus titer is measured in serum, lymph nodes, spleen, and/or brain. Gene and cytokine expression at various time points during infection in compound-treated versus control animals can be assayed.

Mouse influenza model. Virus infection is done by non-surgical intranasal or tracheal instillation of influenza virus strains A/WSN/33 and A/Udorn/72. These influenza virus strains are two different subtypes (H1N1 and H3N2) and exhibit varying pathogenic properties and clinical presentations in C57Bl/6 mice. Compounds are administered daily by oral gavage or IP administration over the entire course of infection (≥2 weeks) at 2 dose levels plus a placebo control group. Animals are evaluated for study endpoints including daily clinical observations, mortality, body weight, and body temperature. Virus titer is measured in serum, heart, lung, kidney, liver, and/or brain. Gene and cytokine expression at various time points during infection in compound-treated versus control animals can be assayed.

Mouse RSV model. Virus infection is done by non-surgical intranasal or tracheal instillation of RSV A2 long strain at a dose that does not cause cytopathic effects. Compounds are administered daily by oral gavage or IP administration for 3 weeks, at 2 dose levels or a placebo control. Animals are evaluated for study endpoints including daily clinical observations, mortality, body weight, and body temperature. Virus titer is measured in serum, blood, and/or lung. Gene and cytokine expression, and increased immune cell population counts can be assayed.

Mouse DNV model. Virus infection is done by intraperitoneal injection of DNV type 2 strain. Compounds are administered daily by oral gavage or IP administration over the entire course of infection at 2 dose levels plus a placebo control group. Animals are evaluated for study endpoints including daily clinical observations, mortality, body weight, and body temperature. Virus titer is measured in serum, blood, heart, lung, kidney, liver, and/or brain. Gene and cytokine expression at various time points during infection in compound-treated versus control animals can be assayed.

Mouse hepatitis virus type 1 (MHV-1) coronavirus model. Virus infection is done by non-surgical intranasal instillation of MHV-1. Compounds are administered daily by oral gavage or IP administration over the entire course of infection (≥1 week) at 2 dose levels plus a placebo control group. Animals are evaluated for study endpoints including daily clinical observations, mortality, body weight, and body temperature. Virus titer is measured in serum, heart, lung, kidney, liver, and/or brain. Gene and cytokine expression at various time points during infection in compound-treated versus control animals can be assayed.

Figure 11A:
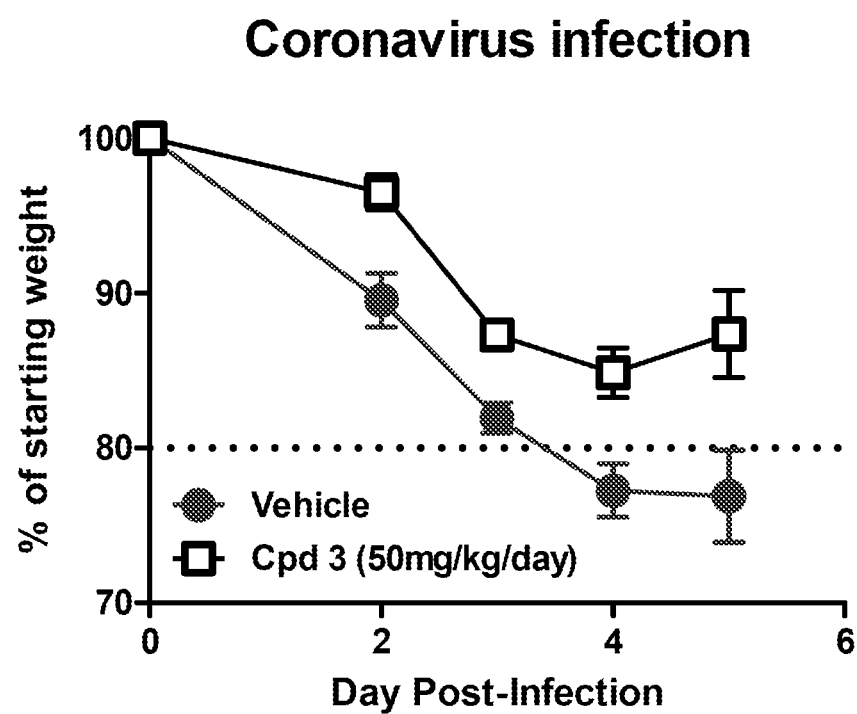
FIG. 11A-11C show a study performed using the mouse hepatitis virus type 1 (MHV-1) coronavirus model. Treatment with compound 3 of Table 1 resulted in decreased pathological symptoms including weight loss FIG. 11A and increased survival 11B after lethal challenge with MHV-1.
Figure 11B:
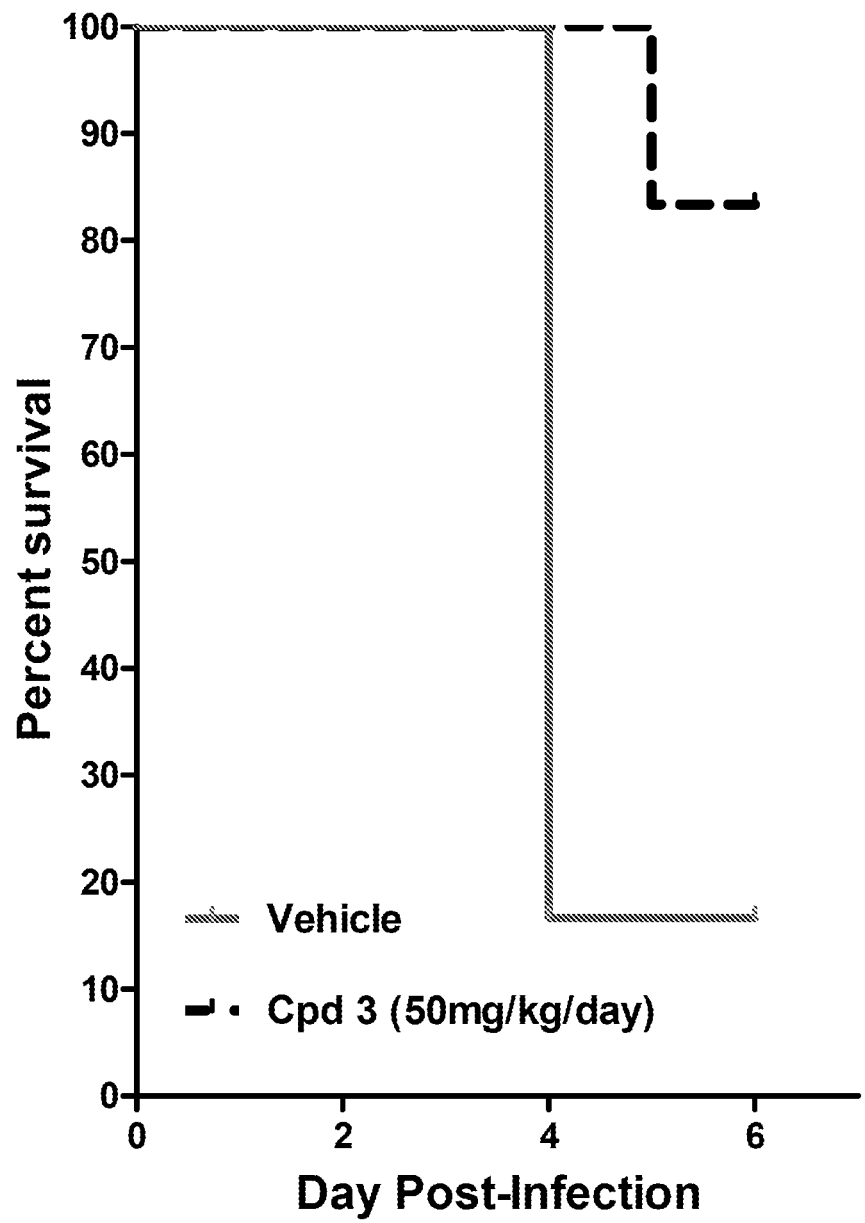
Figure 11C:
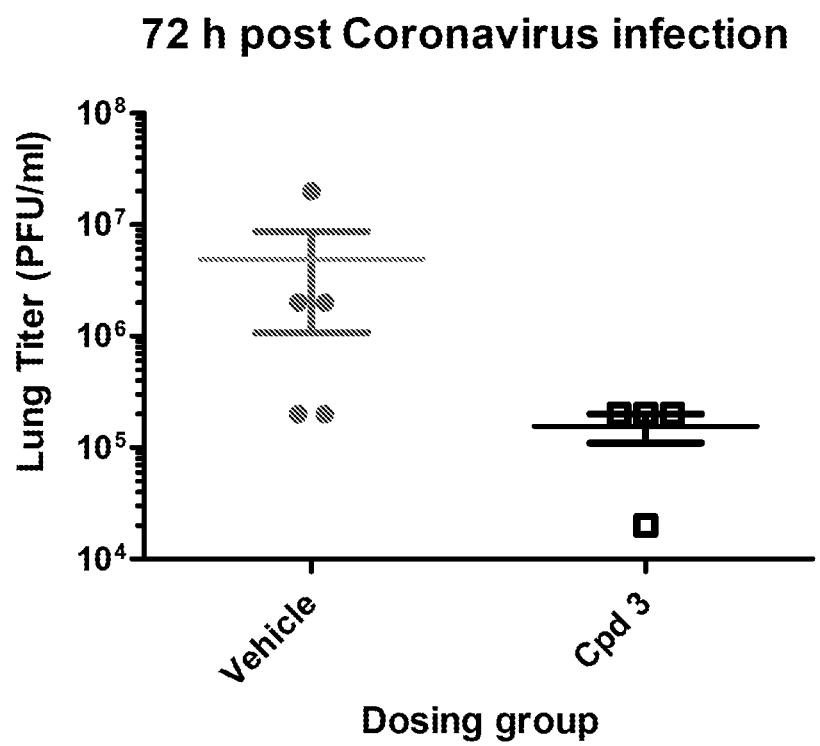
Figure 13:
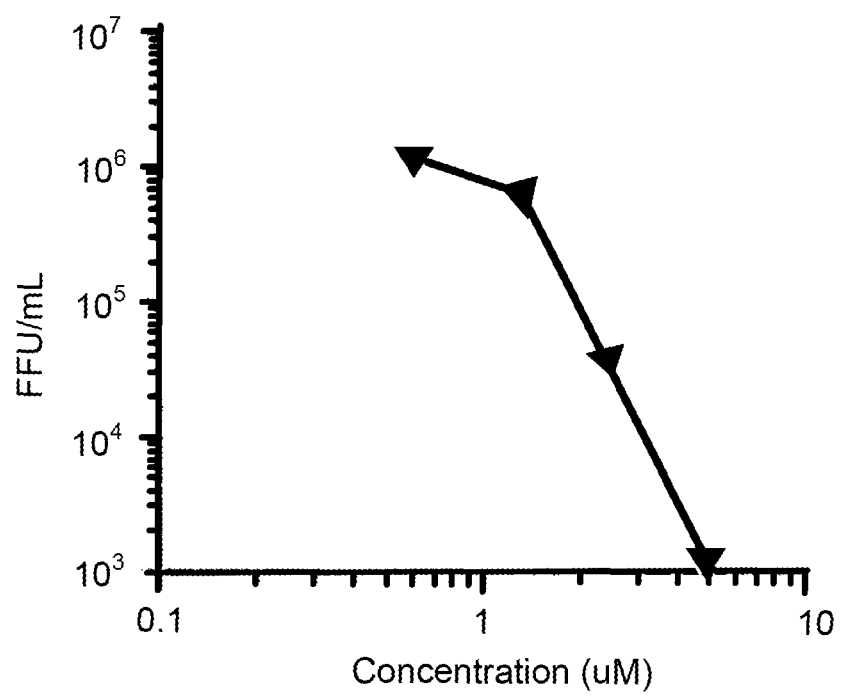
FIG. 13 shows the dose response activity of compound 8 of Table 1 against DENV-2, as FFU/ml.

FIG. 11 shows a study performed using the mouse hepatitis virus type 1 (MHV-1) coronavirus model. Treatment with compound 3 of Table 1 resulted in decreased pathological symptoms including weight loss (A) and increased survival (B) after lethal challenge with MHV-1. (C) Virus was decreased in the lung of animals treated with compound 3.

The antiviral activity of example compounds are described in Table 7.

TABLE 7

| Compound ID | DNV2 EC50 (uM) | DNV4 EC50 (uM) | FLU EC50 (uM) | RSV EC50 (uM) | HCOV EC50 (uM) |
|---|---|---|---|---|---|
| 1 | >10 | 2.1 | >10 | >10 | NA |
| 2 | 6.2 | >5 | 2 | >10 | 9.2 |
| 3 | 1.9 | 1.22 | 6 | 2.3 | 0.54 |
| 4 | 3.6 | NA | 1.3 | 2.8 | NA |
| 5 | 0.5 | 5 | >10 | NA | 0.04 |
| 6 | 2.5 | 2.8 | 1.1 | 1.7 | 0.04 |
| 7 | 0.71 | 3.4 | NA | >3 | 0.02 |
| 8 | 1.2 | NA | NA | NA | NA |
| 9 | 1.8 | 0.9 | 1.1 | 1.8 | NA |
| 10 | 1.4 | 5.6 | 3.2 | 2.9 | NA |
| 11 | 0.5 | 5.2 | NA | NA | NA |
| 12 | 0.2 | 2.8 | 6.8 | 7.5 | NA |
| 13 | 2.0 | 5.5 | 5.3 | 14.00 | NA |
| 15 | 0.4 | 4.6 | 6.8 | >3 | NA |
| 16 | NA | NA | NA | NA | NA |
| 17 | 0.5 | 4.7 | 4.1 | NA | NA |
| 19 | 0.5 | 0.6 | NA | 1.2 | NA |

Example 14

In Vivo Adjuvant Activity

To characterize the breadth of adjuvant activity of compounds of the disclosure, animal models of vaccination and vaccination plus protection are used. The studies include priming animals including rats and mice with compound alone or in combination with an antigen and then assessing the adjuvant effect.

Adjuvant effect is measured by assays for modified, enhanced immune humoral and cellular responses. Humoral responses are assessed over time at discrete times post vaccination and/or boosting by collecting blood for sera and determining relative concentrations of antibody classes (IgM, IgG, IgA or IgE) and/or isotypes including IgG1 IgG2a, IgG2b, IgG2c, IgG3 for IgG antibodies. Moreover, affinity and avidity of the generated antibodies is also determined. In instances in which the vaccine preparation includes a combination of compound and antigen, the neutralizing activity of the generated antibodies is also determined.

Cellular mediated immune responses induced by the compounds are measured by established methods in the field including ex vivo stimulation of peripheral blood mononuclear cells, lymph nodes, splenocytes or other secondary lymphoid organs with the antigen and measurement of cytokine or chemokine production in the supernatant at several times thereafter. Cytokines measured include Th1 type of cytokines including IFN gamma and TNF alpha, Th2 type cytokines including IL-4, IL-10, IL-5 and IL-13 and Th17 cytokines including IL-17, IL-21 and IL-23. Chemokines elicited by the compounds are also measured including RANTES, IP-10, MIP1a, MIP1b, and IL-8. T cell antigen specific production of cytokines can also be measured by intracellular cytokine staining with fluorescently labeled specific antibodies and flow cytometry or by ELISPOT. Both CD4+ and CD8+ T cell populations are studied.

Measurement of adjuvant activity at the cellular level is also determined by immunophenotyping of surface markers of activation by flow cytometry. CD8 T cell antigen-specific responses are also evaluated by intracellular cytokine staining of perforin, cell surface marker expression or proliferation assays including thymidine incorporation.

These experiments are designed to validate compound adjuvant activity in different combinations of prime-boost schemes and assess how compound-induced effects on innate immune antiviral programs shape the adaptive immune responses mounted to the antigen in the vaccine preparations.

Detailed immune response analyses of each compound as described above are conducted with each selected antigen to determine the immune correlates for that particular antigen(s) and compound formulation. These results guide the protection studies in which animals vaccinated and boosted with combinations of select optimized compounds and desired antigen(s) formulations from select infectious agents are later challenged with doses of infectious agent that are known to result in disease or death of the animal. Protection afforded by vaccination is typically measured by monitoring of clinical symptoms and survival.

Example 15

Anti-Viral Activity of Compound 12 of Table 1 Against Ebola Virus

The in vitro efficacy of compound 12 of Table 1 was tested against Ebola virus (EBOV). As shown in FIG. 12, compound 12 showed greater than a 2 log reduction in EBOC titer in vitro. Control titer (pfu/mL) was over 5, whereas the test titer using compound 12 was less than 3.5.

Example 16

Anti-Viral Effect of Compound 8 of Table 1

FIG. 13 shows the dose response activity of compound 8 of Table 1 against DENV-2, as FFU/ml.

Example Embodiments

1. A compound represented by the formula 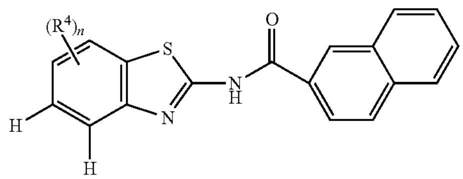 wherein $R^4$ is $R^d$, $SO_2R^d$, $C(=O)R^d$, NH $C(=O)R^d$, $R^e$, $OR^c$, or $CF_3$, wherein $R^c$ is H or $C_1$-$C_{10}$ hydrocarbyl, $R^d$ is substituted heterocyclic, unsubstituted heterocyclic, or unsubstituted carbocyclic, and $R^e$ is substituted heteroaryl or substituted phenyl; and n is 1 or 2.

2. The compound of embodiment 1, represented by the formula 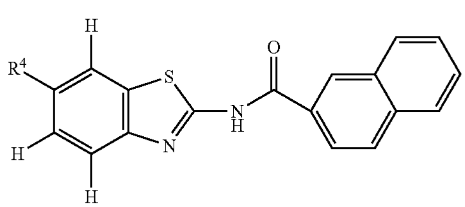 wherein $R^4$ is:

(i) $C(=O)R^d$ and $R^d$ is a pyrrolidonyl group, (ii) $SO_2R^d$ and $R^d$ is a piperidinyl group, (iii) $NHC(=O)R^d$ and $R^d$ is a phenyl group or a furanyl group, (iv) an imidazolyl group, or (v) a thiazolyl group.

3. The compound of embodiment 1, represented by the formula 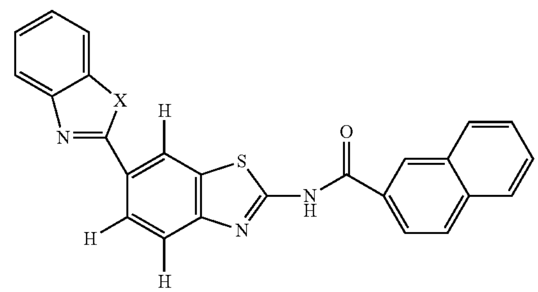 wherein X is NH or O.

4. The compound of embodiment 1, wherein $R^4$ is $CF_3$, $OR^c$, or a phenyl group substituted by at least one $OCH_3$ group.

5. A compound of claim 1 represented by the formula:

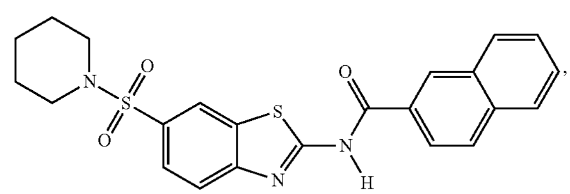

,

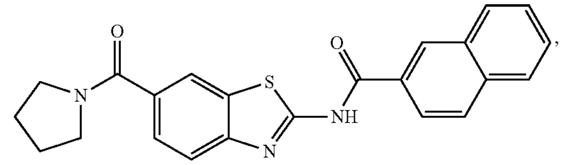

,

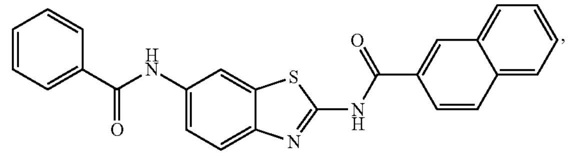

,

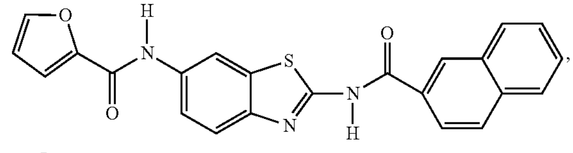

,

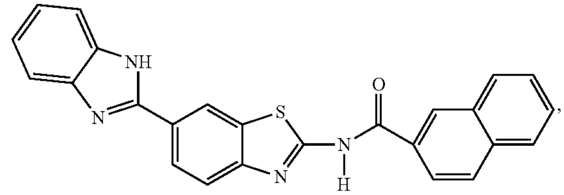

,

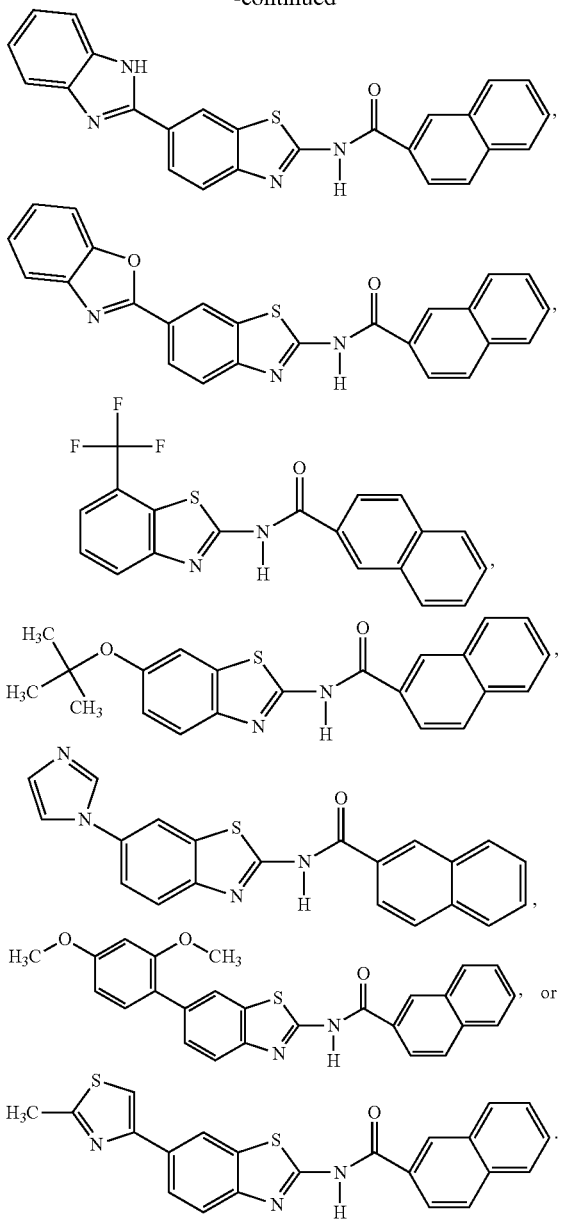

6. A compound represented by the formula

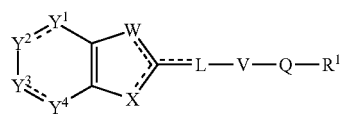

wherein L is NR², O, S, C(=O)N, CR²R³CR²R³, CR²R³NR², CR⁴=CR⁴, CR²R³O, CR²R³S, NR²CR²R³, NR²C(=O), NS(O)$_t$, OCR²R³, SCR²R³;
V is (CR²R³)$_u$, C(=O)CR²R³, CR²R³O, CR²R³OCR²R³, CR⁴=CR⁴, C≡C, C(=NR²), or C(=O);
Q is NR², O, S(O)$_t$, or a bond;
t=0, 1, 2; u=0-3;
wherein a dashed line indicates the presence or absence of a bond;
R¹ is R$^a$, OR², or NR²R³;

each R$^a$ is independently H, optionally substituted hydrocarbyl, optionally substituted aryl, optionally substituted heteroaryl;
R² and R³ are each independently R$^a$, C(=O)R$^a$, SO₂R$^a$, or R² and R³ form an optionally substituted carbocyclic, heterocarbocyclic, aryl, or heteroaryl ring;
each R⁴ is independently R², OR$^a$, C(=O)R$^a$, C(=O)NR²R³, NR²R³, NR$^b$(=O)R$^a$, SR$^a$, SOR$^a$, SO₂R$^a$, SO₂NHR$^a$, SO₂NR²R³, NCOR$^a$, halogen, trihalomethyl, CN, S=O, nitro, or two R⁴ groups form an optionally substituted carbocyclic, heterocarbocyclic, aryl, or heteroaryl ring;
W and X are each independently N, NR$^a$, NR⁵, O, S, CR²R⁴ or CR⁴;
R⁵ is R$^a$, C(=O)R$^a$, SO₂R$^a$, or is not present;
Y¹, Y², Y³ and Y⁴ are each independently CR⁴ or N; and NR²R³ may form an optionally substituted heterocyclic or heteroaryl ring including pyrrolidine, piperidine, morpholine, and piperazine.

7. A compound of embodiment 6, the compound having a structure represented by Formula 1A or 1C Formula 1A

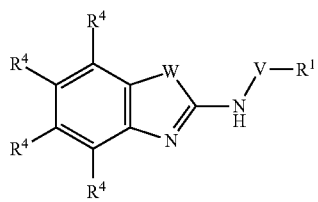

Formula 1C

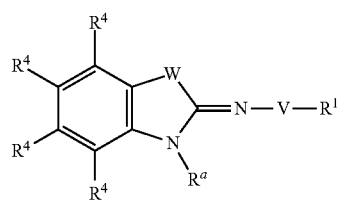

wherein in each of Formula 1A and Formula 1C,
R¹ is R$^a$, OR², or NR²R³;
each R$^a$ is independently H, optionally substituted hydrocarbyl, optionally substituted aryl, optionally substituted heteroaryl;
R² and R³ are each independently R$^a$, C(=O)R$^a$, or SO₂R$^a$;
each R⁴ is independently R², OR$^a$, NR²R³, SR$^a$, SOR$^a$, SO₂R$^a$, SO₂NHR$^a$, NCOR$^a$, C(=O)R$^a$, CONR²R³, halogen, trihalomethyl, CN, S=O, or nitro;
V is CR²R³, C(=O), C(=O)CR²R³, or C(=N)R²; and
W is O or S.

8. A compound of embodiment 6, the compound having a structure represented by the Formula 1B Formula 1B

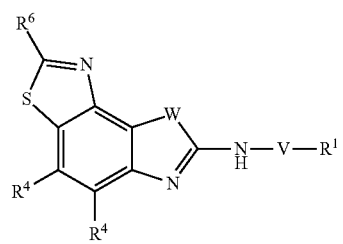

wherein R¹ is R^a, OR² or NR²R³;
each R^a is independently H, optionally substituted hydrocarbyl, optionally substituted aryl, optionally substituted heteroaryl;
R² and R³ are each independently R^a, C(=O)R^a, or SO₂R^a;
each R⁴ is independently R², OR^a, NR²R³, SR^a, SOR^a, SO₂R^a, SO₂NHR^a, NCOR^a, C(=O)R^a, CONR²R³, halogen, trihalomethyl, CN, S=O, or nitro;
R⁶ is H or CH₃.
V is CR²R³, C(=O), C(=O)CR²R³, or C=NR²; and
W is O or S.

9. A compound of embodiment 7 or 8 wherein R4 is H; and V is C=O.

10. A compound of any one of embodiments 7, 8, or 9 wherein R1 is optionally substituted phenyl or optionally substituted naphthyl.

11. A compound of any one of embodiments 6-10, wherein W is S and X is N.

12. A compound of any one of embodiments 6-10, wherein W is O and X is N.

13. A compound of any one of embodiments 6-11 represented by the formula

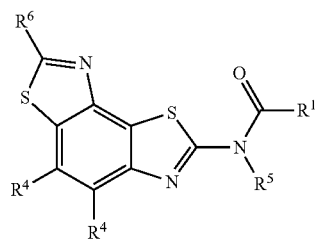

wherein R¹ is a phenyl group substituted by at least one halogen, a phenyl group substituted by NR²R³, a phenyl group substituted by SO₂NR²R³, CR²R³ORd, an unsubstituted napthyl group, a napthyl group substituted by O(CR²R³)ₙR^d, NR^a(CR²R³)ₙR^d, NR^a(CR²R³)ₙNR²R³, a two membered ring structure including a pyridynyl group and a phenyl group, or a two membered ring structure including a phenyl group and a dioxolanyl group;
each R^a is independently H or optionally substituted hydrocarbyl (C₁-C₁₀);
R² and R³ are each independently R^a, COR^a, (CH2)ₙO, or SO₂R^a;
each R⁴ is independently R^a
R^d is phenyl or morpholino
R⁵ is H or CH₃;
R⁶ is H or CH₃; and
wherein n is 1, 2, 3, or 4.

14. A compound of embodiment 13 represented by the formula

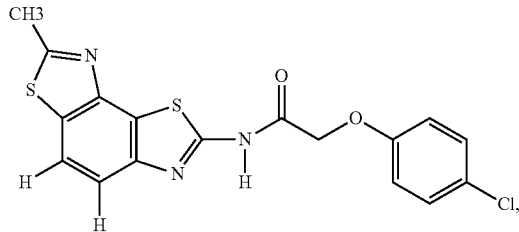

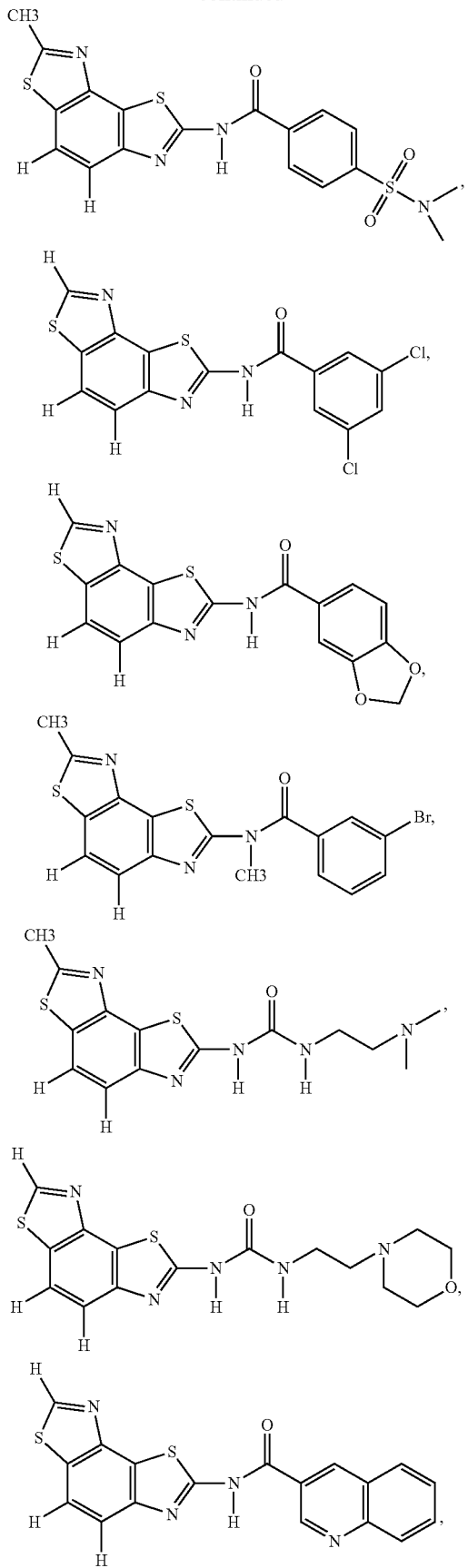

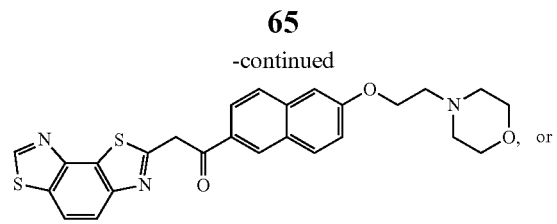

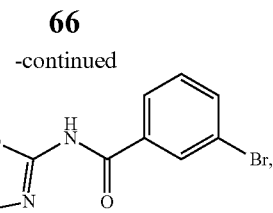

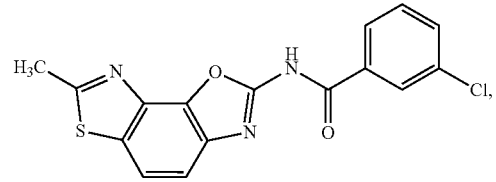

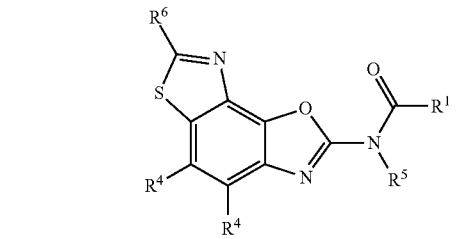

15. A compound of any one of embodiments 5-9 and 11 represented by the formula

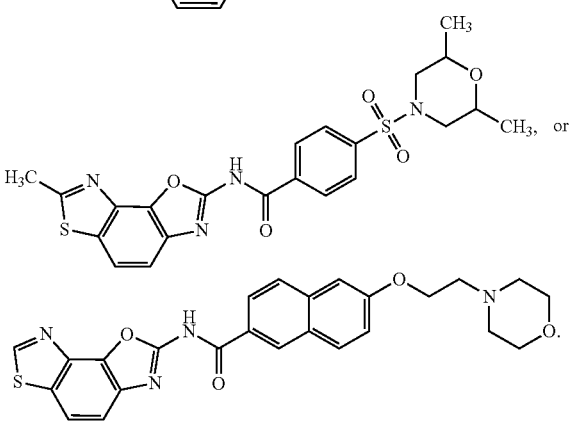

wherein $R^1$ is a phenyl group substituted by at least one halogen, a phenyl group substituted by $NR^2R^3$, a phenyl group substituted by $SO_2R^d$, a napthyl group optionally substituted by $O(CR^2R^3)_n R^d$, or an unsubstituted napthyl group, each $R^a$ is independently H or optionally substituted $C_1$-$C_{10}$ hydrocarbyl;

$R^2$, $R^3$ and each $R^4$ are independently $R^a$, $R^d$ is optionally substituted phenyl or optionally substituted morpholino;

$R^5$ is H or $CH_3$;

$R^6$ is H or $CH_3$, and wherein n is 1, 2, 3, or 4.

16. A compound of embodiment 15, represented by the formula:

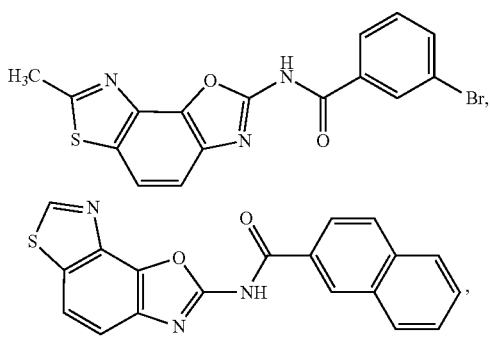

17. A pharmaceutical composition comprising a compound of any one of embodiments 1 to 16.

18. A method of treating a viral infection in a subject comprising administering to the subject a therapeutically effective amount of a pharmaceutical composition of embodiment 17 thereby treating the viral infection in the subject.

19. A method of preventing a viral infection in a subject comprising administering to the subject a therapeutically effective amount of a pharmaceutical composition of embodiment 17.

20. A method of embodiment 18 or embodiment 19 wherein the viral infection is caused by a virus from one or more of the following families: Arenaviridae, Arterivirus, Astroviridae, Birnaviridae, Bromoviridae, Bunyaviridae, Caliciviridae, Closteroviridae, Comoviridae, Coronaviridae, Cystoviridae, Filoviridae, Flaviviridae, Flexiviridae, Hepadnaviridae, Hepevirus, Herpesviridae, Leviviridae, Luteoviridae, Mesoniviridae, Mononegavirales, Mosaic Viruses, Nidovirales, Nodaviridae, Orthomyxoviridae, Papillomaviridae, Paramyxoviridae, Picobirnaviridae, Picobirnavirus, Picornaviridae, Potyviridae, Reoviridae, Retroviridae, Roniviridae, Sequiviridae, Tenuivirus, Togaviridae, Tombusviridae, Totiviridae, and Tymoviridae.

21. A method of embodiment 18 or embodiment 19 wherein the viral infection is caused by Alfuy virus, Banzi virus, bovine diarrhea virus, Chikungunya virus, Dengue virus (DNV), Hepatitis B virus (HBV), Hepatitis C virus (HCV), human cytomegalovirus (hCMV), human immunodeficiency virus (HIV), Ilheus virus, influenza virus (including avian and swine isolates), rhinovirus, norovirus, adenovirus, Japanese encephalitis virus, Kokobera virus, Kunjin virus, Kyasanur forest disease virus, louping-ill virus, measles virus, MERS-coronavirus (MERS), metapneumovirus, any of the Mosaic Viruses, Murray Valley virus, parainfluenza virus, poliovirus, Powassan virus, respiratory syncytial virus (RSV), Rocio virus, SARS-coronavirus (SARS), St. Louis encephalitis virus, tick-borne encephalitis virus, West Nile virus (WNV), Ebola virus, Nipah virus, Lassa virus, Tacaribe virus, Junin virus, or yellow fever virus.

22. A pharmaceutical composition of embodiment 17, for use in therapy.

23. A pharmaceutical composition for use according to embodiment 22, wherein said pharmaceutical composition is administered as an adjuvant for a prophylactic or therapeutic vaccine.

24. A method of modulating the innate immune response in a eukaryotic cell, comprising administering to the cell a compound of any one of embodiments 1 to 16.

25. A method of embodiment 24, wherein the cell is in vivo.

26. A method of embodiment 25, wherein the cell is in vitro.

27. A method of treating a viral infection in a subject comprising administering to the subject a therapeutically effective amount of a pharmaceutical composition having the structure

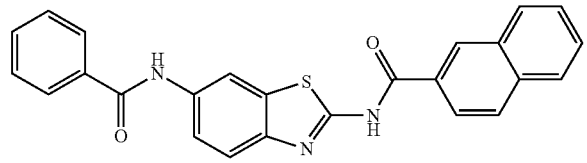 [SMILES: O=C(Nc1ccc2nc(NC(=O)c3ccc4ccccc4c3)sc2c1)c1ccccc1]

and wherein the viral infection is caused by Ebola virus.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of" As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically significant reduction in a disclosed compound's or composition's ability to treat a viral infection in a subject; reduce viral protein in a subject or assay; reduce viral RNA in a subject or assay or reduce virus in a cell culture.

Unless otherwise indicated, all numbers expressing quantities of ingredients, properties such as molecular weight, reaction conditions, and so forth used in the specification and claims are to be understood as being modified in all instances by the term "about," Accordingly, unless indicated to the contrary, the numerical parameters set forth in the specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Numerous references have been made to publications, patents and/or patent applications (collectively "references") throughout this specification. Each of the cited references is individually incorporated herein by reference for their particular cited teachings.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

What is claimed is:

1. A compound represented by the formula

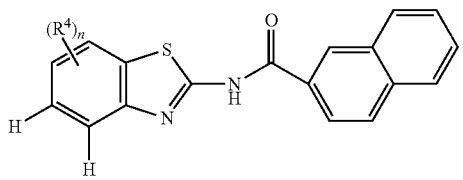

wherein
R$^4$ is selected from C(=O)NR$^2$R$^3$ and NR$^b$(C=O)R$^a$,
  wherein R$^2$ and R$^3$ are each independently selected from
    (i) hydrogen,
    (ii) optionally substituted hydrocarbyl,
    (iii) optionally substituted aryl, and
    (iv) optionally substituted heteroaryl, or
  R$^2$ and R$^3$ taken together form an optionally substituted carbocyclic, heterocarbocyclic, aryl, or heteroaryl ring,
  wherein R$^a$ is selected from
    (i) optionally substituted aryl, and
    (ii) optionally substituted heteroaryl,
  wherein R$^b$ is selected from
    (i) hydrogen, and
    (ii) optionally substituted C$_{1-3}$ hydrocarbyl; and
n is 1 or 2.

2. A compound of claim 1, represented by the formula

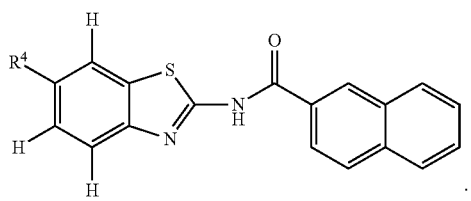

3. A compound of claim 1, represented by the formula

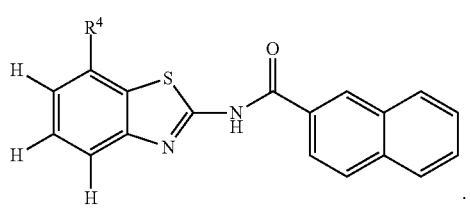

4. A compound of claim 1, wherein R$^4$ is C(=O)NR$^2$R$^3$, wherein R$^2$ and R$^3$ are each independently selected from hydrogen, optionally substituted hydrocarbyl, optionally substituted aryl, and optionally substituted heteroaryl.

5. A compound of claim 1, wherein R$^4$ is C(=O)NR$^2$R$^3$, and wherein R$^2$ and R$^3$ taken together form an optionally substituted carbocyclic, heterocarbocyclic, aryl, or heteroaryl ring.

6. A compound of claim 1 having the formula

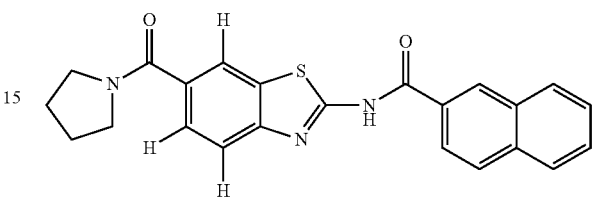

7. A compound of claim 1, wherein R$^4$ is NR$^b$(C=O)R$^a$, wherein R$^a$ is selected from optionally substituted aryl, and optionally substituted heteroaryl, and wherein R$^b$ is hydrogen.

8. A compound of claim 1 selected from

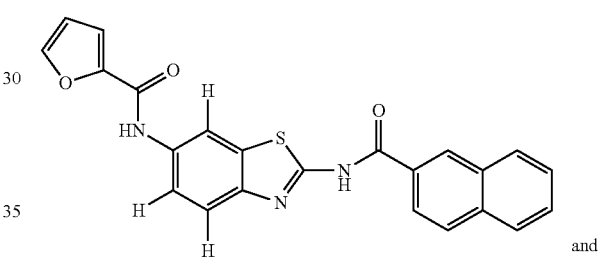

and

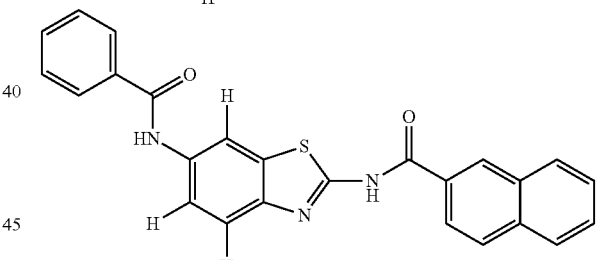

9. A pharmaceutical composition comprising a compound of claim 1.

10. A method of activating the RIG-I pathway in a eukaryotic cell, comprising administering to the cell an amount of a compound of claim 1 effective to activate the RIG-I pathway.

11. A method of claim 10, wherein the cell is in vivo.

12. A method of claim 11, wherein the cell is in vitro.

13. A method of treating a viral infection selected from influenza, Dengue virus, hepatitis B, or respiratory syncytial virus in a subject having said viral infection comprising administering to the subject a therapeutically effective amount of a pharmaceutical composition of claim 9.

14. A method of treating a viral infection caused by Ebola virus in a subject having said viral infection comprising administering to the subject a therapeutically effective amount of a pharmaceutical composition comprising a compound having the structure

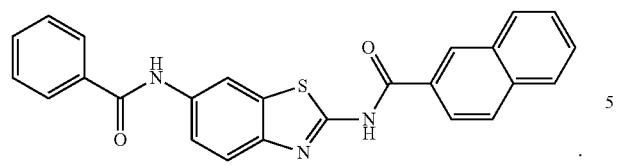
* * * * *

UNITED STATES PATENT AND TRADEMARK OFFICE
CERTIFICATE OF CORRECTION

PATENT NO.        : 9,884,876 B2                               Page 1 of 1
APPLICATION NO.   : 15/308058
DATED             : February 6, 2018
INVENTOR(S)       : S. P. Iadonato et al.

It is certified that error appears in the above-identified patent and that said Letters Patent is hereby corrected as shown below:

In the Claims

| Column | Line | |
|---|---|---|
| 70 | 57 | "claim 11" should read --claim 10-- |
| Claim 12 | | |

Signed and Sealed this
Nineteenth Day of June, 2018

Andrei Iancu
*Director of the United States Patent and Trademark Office*